US012617860B2

(12) United States Patent
Wei et al.

(10) Patent No.: US 12,617,860 B2
(45) Date of Patent: May 5, 2026

(54) ANTI-TNFR2 ANTIBODY AND USES THEREOF

(71) Applicant: HIFIBIO INC., Cambridge, MA (US)

(72) Inventors: Shuo Wei, Bedford, MA (US); Liang Schweizer, Cambridge, MA (US); Francisco Adrian, Cambridge, MA (US); Nicola Arturo Aldo Beltraminelli, Cambridge, MA (US); Pascaline Mary, Cambridge, MA (US); Matthieu Delince, Cambridge, MA (US); Qian Zhang, Cambridge, MA (US); Jennifer Watkins, Cambridge, MA (US)

(73) Assignee: HIFIBIO INC., Cambridge, MA (US)

( * ) Notice: Subject to any disclaimer, the term of this patent is extended or adjusted under 35 U.S.C. 154(b) by 828 days.

(21) Appl. No.: 17/791,056

(22) PCT Filed: Jan. 5, 2021

(86) PCT No.: PCT/US2021/012197
§ 371 (c)(1),
(2) Date: Jul. 6, 2022

(87) PCT Pub. No.: WO2021/141907
PCT Pub. Date: Jul. 15, 2021

(65) Prior Publication Data
US 2023/0045791 A1 Feb. 16, 2023

Related U.S. Application Data

(60) Provisional application No. 63/041,234, filed on Jun. 19, 2020, provisional application No. 62/957,543, filed on Jan. 6, 2020.

(51) Int. Cl.
| | |
|---|---|
| *C07K 16/28* | (2006.01) |
| *A61K 39/395* | (2006.01) |
| *A61P 1/00* | (2006.01) |
| *A61P 35/00* | (2006.01) |
| *A61K 39/00* | (2006.01) |

(52) U.S. Cl.
CPC ...... *C07K 16/2878* (2013.01); *A61K 39/3955* (2013.01); *A61P 1/00* (2018.01); *A61P 35/00* (2018.01); *C07K 16/2818* (2013.01); *A61K 2039/505* (2013.01); *A61K 2039/507* (2013.01); *C07K 2317/24* (2013.01); *C07K 2317/33* (2013.01); *C07K 2317/565* (2013.01); *C07K 2317/74* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2019/0135929 A1 | 5/2019 | Faustman | |
| 2019/0144556 A1* | 5/2019 | Faustman | ...... A61K 39/001117 424/85.7 |
| 2020/0270355 A1 | 8/2020 | Faustman | |
| 2021/0317221 A1* | 10/2021 | Faustman | .......... C07K 16/2878 |

FOREIGN PATENT DOCUMENTS

| | | |
|---|---|---|
| CN | 112480259 A | 3/2021 |
| JP | 2016-509009 A | 3/2016 |
| WO | 2014/124134 A1 | 8/2014 |
| WO | 2016/187068 A1 | 11/2016 |
| WO | 2017/040312 A1 | 3/2017 |
| WO | 2020/061210 A1 | 3/2020 |
| WO | 2020/180712 A1 | 9/2020 |
| WO | 2021/023098 A1 | 2/2021 |
| WO | 2021/055253 A2 | 3/2021 |

OTHER PUBLICATIONS

Case et al., TNFR2 blockade alone or in combination with PD-1 blockade shows therapeutic efficacy in murine cancer models. J Leukoc Biol. Jun. 2020;107(6):981-991.
Yang et al., TNFR2: Role in Cancer Immunology and Immunotherapy. Immunotargets Ther. Apr. 21, 2021;10:103-122.
International Preliminary Report on Patentability for Application No. PCTIB2022/000409, dated Jan. 18, 2024, 4 pages.
International Search Report and Written Opinion for Application No. PCTIB2022/000409, dated Dec. 20, 2022, 11 pages.
Torrey et al., Targeting TNFR2 with antagonistic antibodies inhibits proliferation of ovarian cancer cells and tumor-associated Tregs. Sci Signal. Jan. 17, 2017;10(462):eaaf8608.
International Preliminary Report on Patentability for Application No. PCT/US2021/012197, dated Jul. 12, 2022, 9 pages.
International Search Report and Written Opinion for Application No. PCT/US2021/012197, dated Jun. 14, 2021, 16 pages.

* cited by examiner

*Primary Examiner* — Zachary S Skelding
(74) *Attorney, Agent, or Firm* — McCarter & English, LLP

(57) ABSTRACT

The invention provides monoclonal antibodies and antigen-binding fragments thereof specific for TNFR2, and methods of using the same to treat cancer or autoimmune disorder, including combination therapy with antagonists of the PD-1/PD-L1 immune checkpoint.

17 Claims, 50 Drawing Sheets
Specification includes a Sequence Listing.

FIG. 1

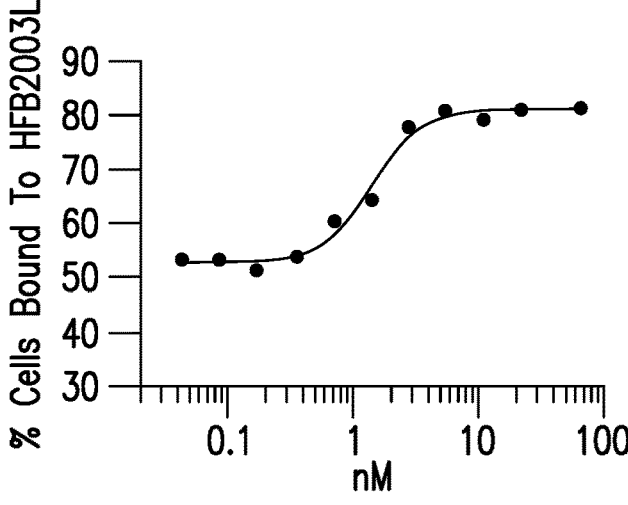
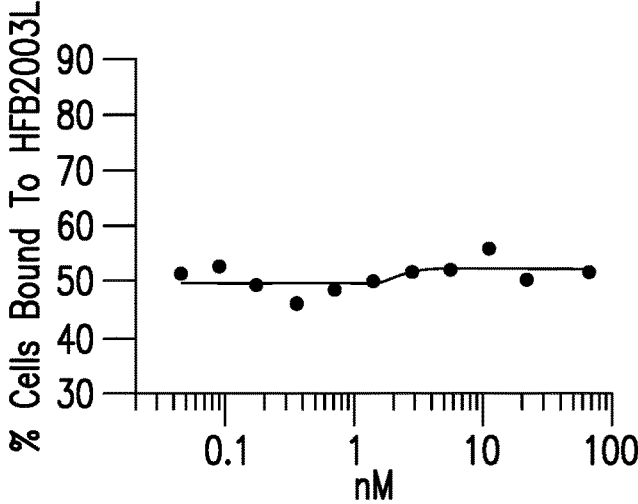
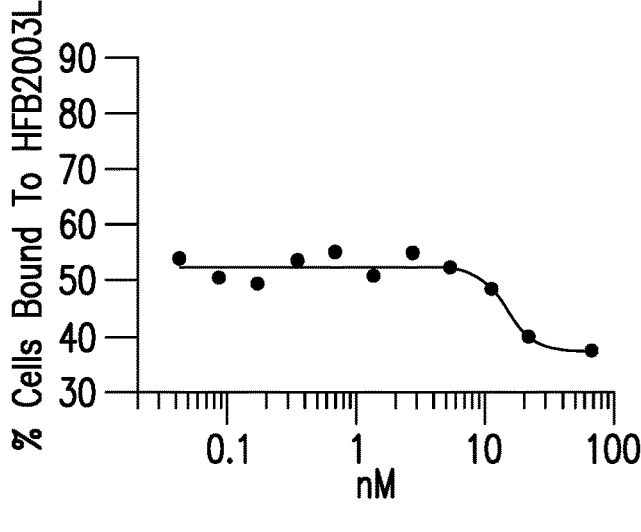
FIG.2B

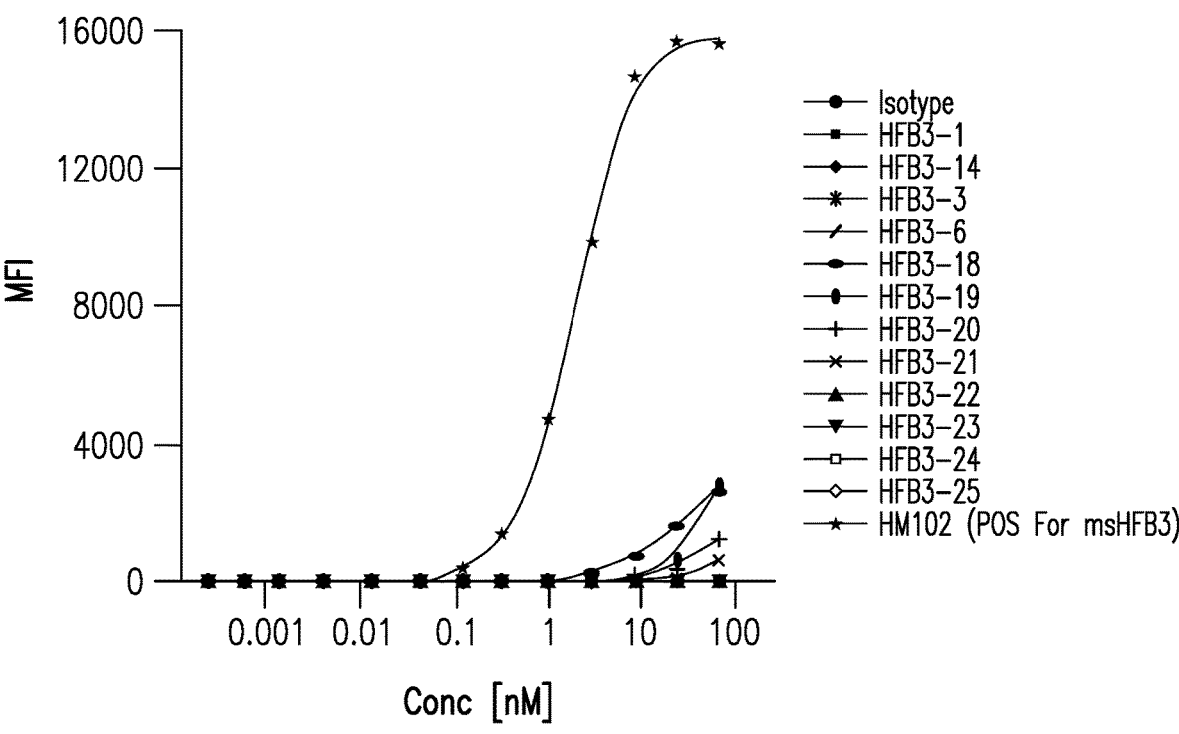
CHO.msHFB3
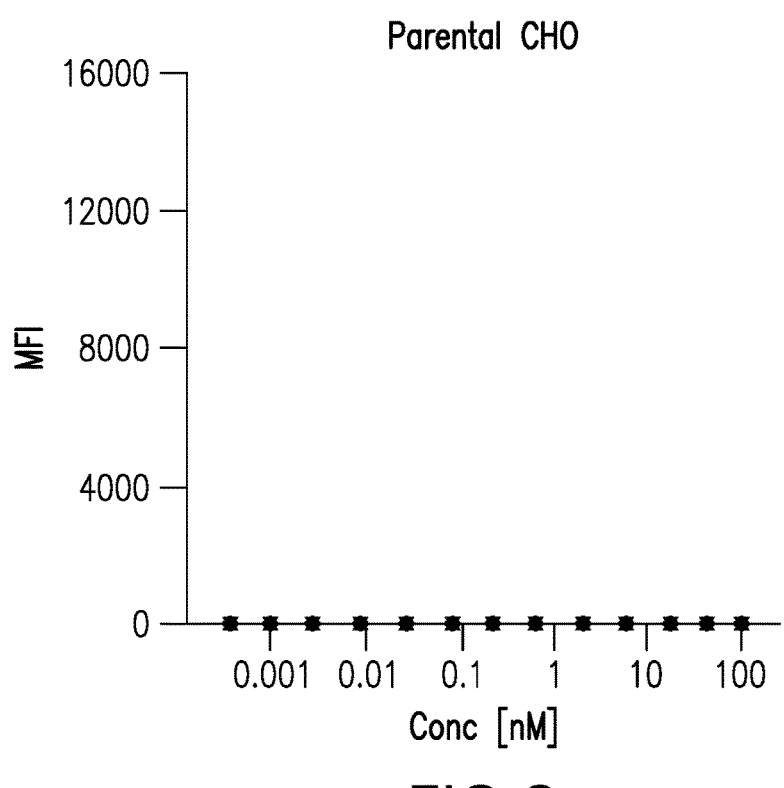
Parental CHO
FIG.3

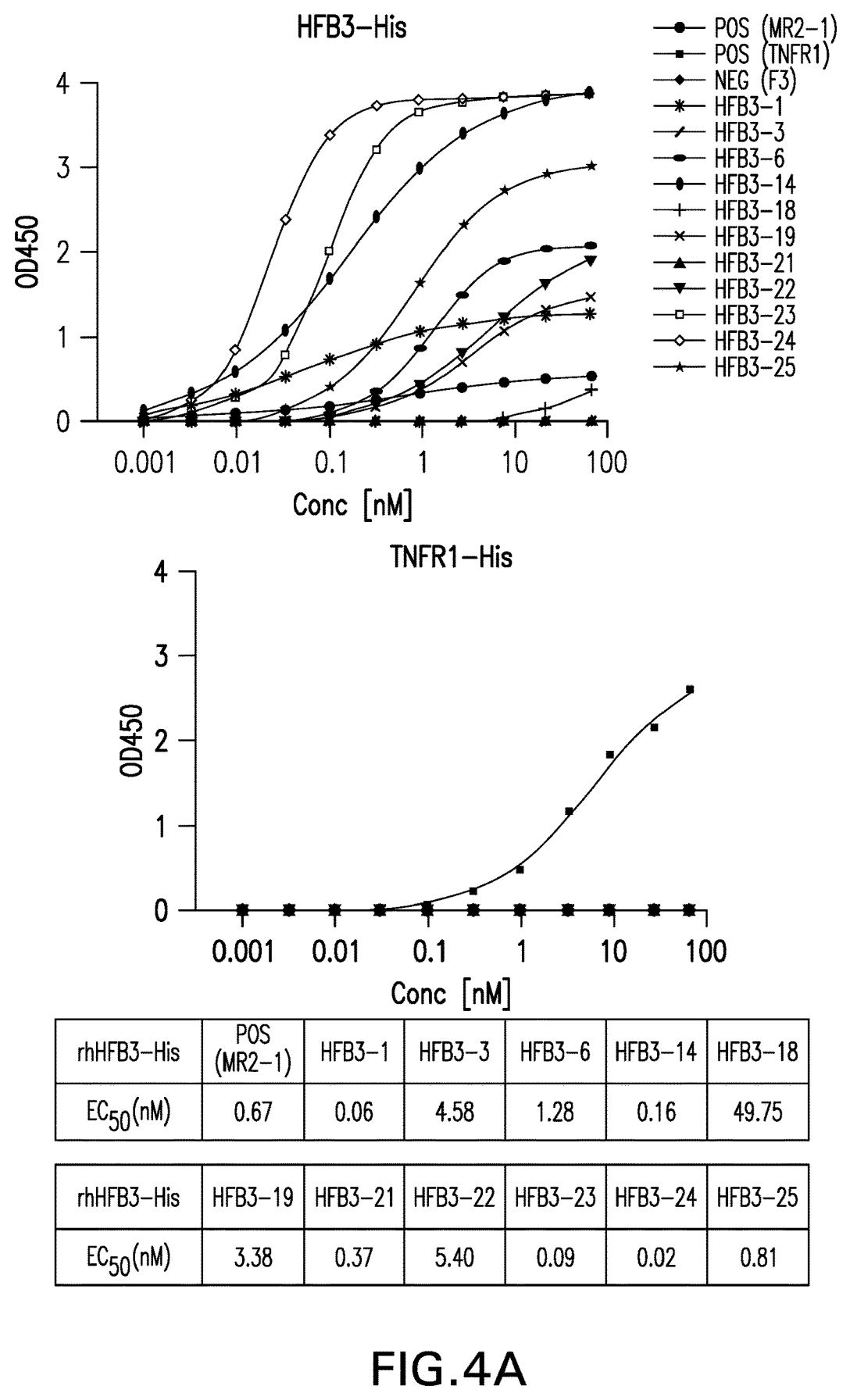

| rhHFB3-His | POS (MR2-1) | HFB3-1 | HFB3-3 | HFB3-6 | HFB3-14 | HFB3-18 |
|---|---|---|---|---|---|---|
| EC$_{50}$(nM) | 0.67 | 0.06 | 4.58 | 1.28 | 0.16 | 49.75 |

| rhHFB3-His | HFB3-19 | HFB3-21 | HFB3-22 | HFB3-23 | HFB3-24 | HFB3-25 |
|---|---|---|---|---|---|---|
| EC$_{50}$(nM) | 3.38 | 0.37 | 5.40 | 0.09 | 0.02 | 0.81 |

FIG.4A

|  | $K_d$ (nM) | $K_{on}$ (1/ms) | $K_{off}$ (1/s) |
|---|---|---|---|
| HFB3−1 | 1.4 | 8.22 E+3 | 1.15 E−5 |
| HFB3−14 | 5.4 | 2.38 E+4 | 1.28 E−4 |
| HFB3−18 | 4.2 | 3.77 E+3 | 1.35 E−5 |

FIG.4B

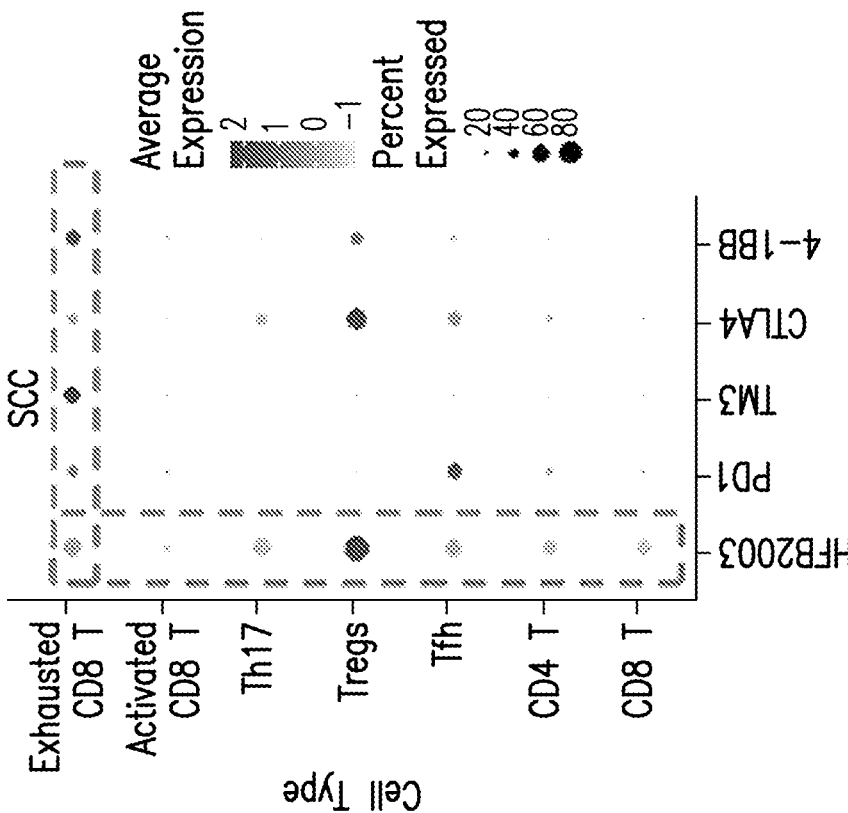
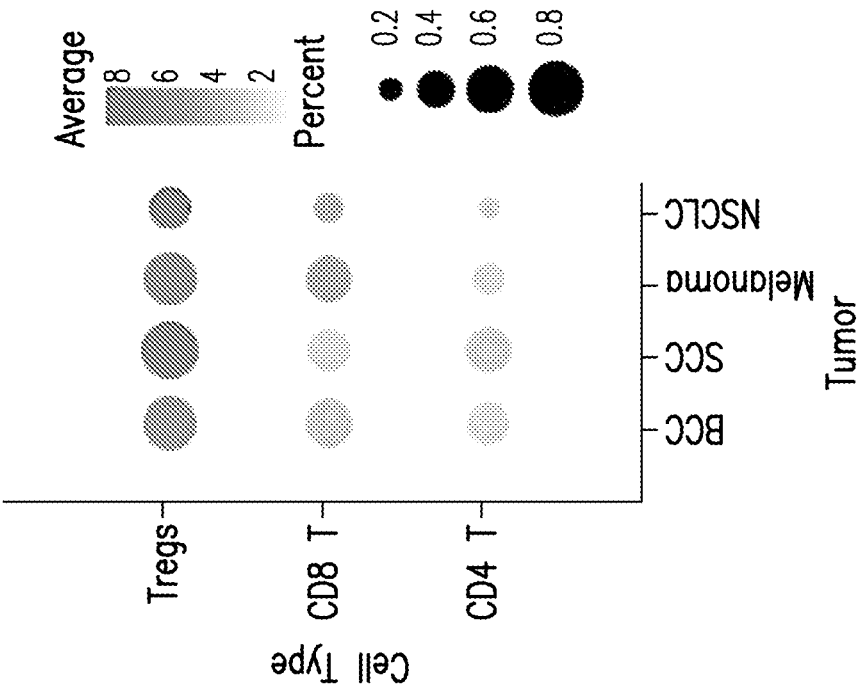
FIG.5

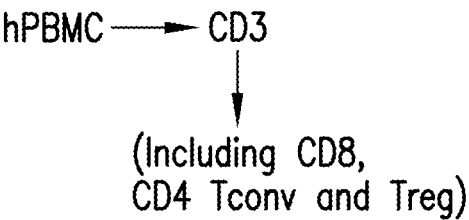
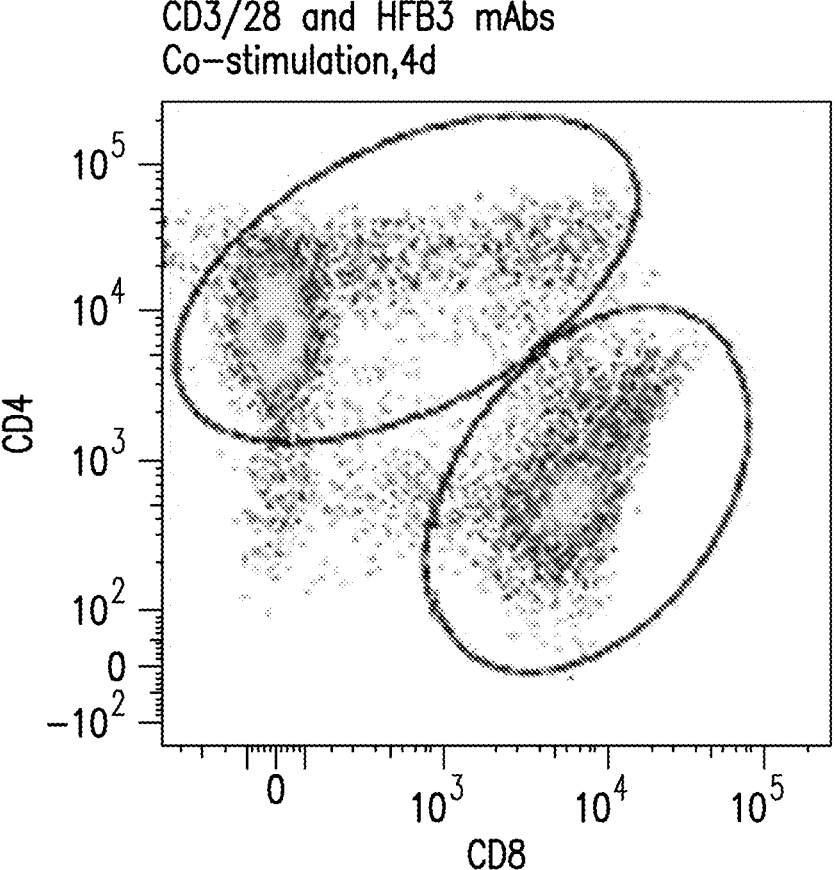
FIG.9

> HFB2003 ECD-His

```
a.a
      1
  1-  LPAQVAFTPY APEPGSTCRL REYYDQTAQM CCSKCSPGQH AKVFCTKTSD  -50
                                              *    *
CRD1
     54
 51-  TVCDSCEDST YTQLWNWVPE CLSCGSRCSS DQVETQACTR EQNRICTCRP  -100
          *    *  *         *    ****  ****  *
CRD2
     96
101-  GWYCALSKQE GCRLCAPLRK CRPGFGVARP GTETSDVVCK PCAPGTFSNT  -150
      *              **  *        *
CRD3
    140
151-  TSSTDICRPH QICNVVAIPG NASMDAVCTS TSPTRSMAPG AVHLPQPVST  -200
           *
CRD4
    200
201-  RSQHTQPTPE PSTAPSTSFL LPMGPSPPAE GSTGD HHHHHH
```

Color code:
☐ HFB3-1-hG1 epitope
⬚ HFB3-14-hG1 epitope
☐ HFB3-6-hG1 epitope
— Benchmark 1 epitope
— Benchmark 2 epitope
* TNFα binding site

FIG.11B

HFB3-1-hG1    HFB3-14-hG1    HFB3-6-hG1    HFB3-18-hG1

▧ TNFα molecule
▨ TNFR2 molecule

FIG.11C

HFB3–14hz Selection

Legend:
- ●—*HFB3–14
- ■—*HFB3–14hz1c
- ◆—HFB3–14hz2c
- *—HFB3–14hz3c
- ↗—*HFB3–14hz4c
- ●—HFB3–14hz5c
- ●—*HFB3–14hz6c
- +—*HFB3–14hz7c
- ×—HFB3–14hz8c
- ▲—HFB3–14hz9c
- ▶—HFB3–14hz10c
- □—HFB3–14hz11c
- ◇—*HFB3–14hz12c
- ★—*HFB3–14hz13c
- ▼—*HFB3–14hz14c
- ↗—*HFB3–14hz15c
- *—*HFB3–14hz16c mAb Format = IgG1AA

| Variant | HFB3–14 | 14hz 1c | 14hz 2c | 14hz 3c | 14hz 4c | 14hz 6c | 14hz 7c |
|---|---|---|---|---|---|---|---|
| EC50 (nM) | 1.925 | 1.770 | 0.7475 | 0.5409 | 1.858 | 3.905 | 2.803 |

| Variant | HFB3–14 | 14hz 1c | 14hz 2c | 14hz 3c | 14hz 12c | 14hz 14c | |
|---|---|---|---|---|---|---|---|
| EC50 (nM) | 1.925 | 1.927 | 1.814 | 2.557 | 2.595 | 5.808 | 3.484 | 3.497 | 4.704 |

HFB3—1hz Selection

| | | | | | | | | | |
|---|---|---|---|---|---|---|---|---|---|
| • | HFB3—1mu | | | | | | | | |
| ■ | HFB3—1hz1 | | | | | | | | |
| ♦ | HFB3—1hz6 | | | | | | | | |
| * | HFB3—1hz8 | | | | | | | | |
| / | HFB3—1hz9 | | | | | | | | |
| ● | HFB3—1hz10 | | | | | | | | |
| ● | HFB3—1hz11 | | | | | | | | |
| + | HFB3—1hz12 | | | | | | | | |
| × | HFB3—1hz13 | | | | | | | | |
| ▲ | HFB3—1hz14 | | | | | | | | | mAb Format = IgG1AA

| Variant | HFB3—1 | 1hz1 | 1hz6 | 1hz8 | 1hz9 | 1hz10 | 1hz11 | 1hz12 | 1hz14 |
|---|---|---|---|---|---|---|---|---|---|
| EC50 (nM) | 5.37 | 11.89 | 19.09 | 4.30 | 41.50 | 74.47 | 25.29 | 6.315 | 36.00 |

FIG.13

HFB3-14hz Selection

| Variant | HFB3-14 | 14hz1c | 14hz2c | 14hz3c | 14hz4c | 14hz6c | 14hz7c | 14hz12c | 14hz14c |
|---|---|---|---|---|---|---|---|---|---|
| EC50 (nM) | 2.15 | 0.70 | 0.16 | 0.08 | 2.93 | 0.95 | 0.60 | 1.47 | 3.14 |

* High MFI Group
+ Low MFI Group mAb Format = IgG1AA

HFB3-14hz Selection

| Lot MF20190507 | Kd (nM) | Kon (1/Ms) | Koff (1/s) |
|---|---|---|---|
| HFB3-14-hG1 | 5.4 | 2.38E+04 | 1.28E-04 |
| HFB3-14hz1chG1AA | 2.8 | 4.23E+04 | 1.17E-04 |
| HFB3-14hz2chG1AA | 3.0 | 3.46E+04 | 1.05E-04 |
| HFB3-14hz3chG1AA | 2.4 | 3.92E+04 | 9.38E-05 |
| HFB3-14hz4chG1AA | 6.4 | 2.62E+04 | 1.67E-04 |
| HFB3-14hz6chG1AA | 5.3 | 2.51E+04 | 1.32E-04 |
| HFB3-14hz7chG1AA | 4.6 | 3.38E+04 | 1.56E-04 |
| HFB3-14hz12chG1AA | 4.5 | 2.56E+04 | 1.15E-04 |
| HFB3-14hz14chG1AA | 6.3 | 2.27E+04 | 1.43E-04 |

*Values Are From The Average of 2 Experiments on Different Days

HFB3-1hz Selection

| Lot MF20190212 | Kd (nM) | Kon (1/Ms) | Koff (1/s) |
|---|---|---|---|
| HFB3-1hG1 | 6.30 | 1.97E4 | 1.24E-04 |
| HFB3-1hz6hG1AA | 15.2 | 8.57E3 | 1.28E-04 |
| HFB3-1hz9hG1AA | 18.7 | 6.52E3 | 1.22E-04 |
| HFB3-1hz10hG1AA | 17.1 | 8.28E3 | 1.41E-04 |
| HFB3-1hz11hG1AA | 16.6 | 8.34E3 | 1.40E-04 |
| HFB3-1hz12hG1AA | 9.1 | 7.47E3 | 6.75E-05 |
| HFB3-1hz14hG1AA | 20.7 | 8.86E3 | 1.83E-04 |

Octet
Biosensor: AHC
Sensor Loading: Antibodies (20µg/mL in Assay Buffer)
Assay Buffer: PBS, pH7.4; 0.1%BSA, 0.1% Tween20
Analyte: rhHFB3-His @ 500, 167 and 55.7 nM
Temperature: 25 Degree

FIG.14B

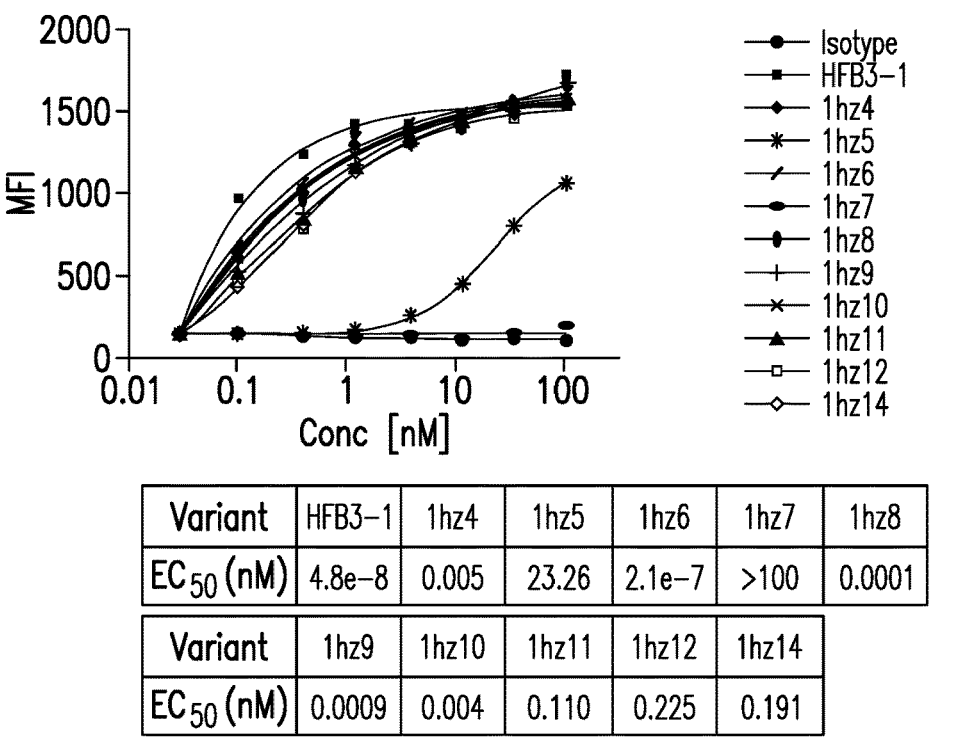
HFB3-1hz Selection
| Variant | HFB3-1 | 1hz4 | 1hz5 | 1hz6 | 1hz7 | 1hz8 |
|---------|--------|------|------|------|------|------|
| EC$_{50}$ (nM) | 4.8e-8 | 0.005 | 23.26 | 2.1e-7 | >100 | 0.0001 |
| Variant | 1hz9 | 1hz10 | 1hz11 | 1hz12 | 1hz14 |
|---------|------|-------|-------|-------|-------|
| EC$_{50}$ (nM) | 0.0009 | 0.004 | 0.110 | 0.225 | 0.191 |
mAb Format = IgG1AA
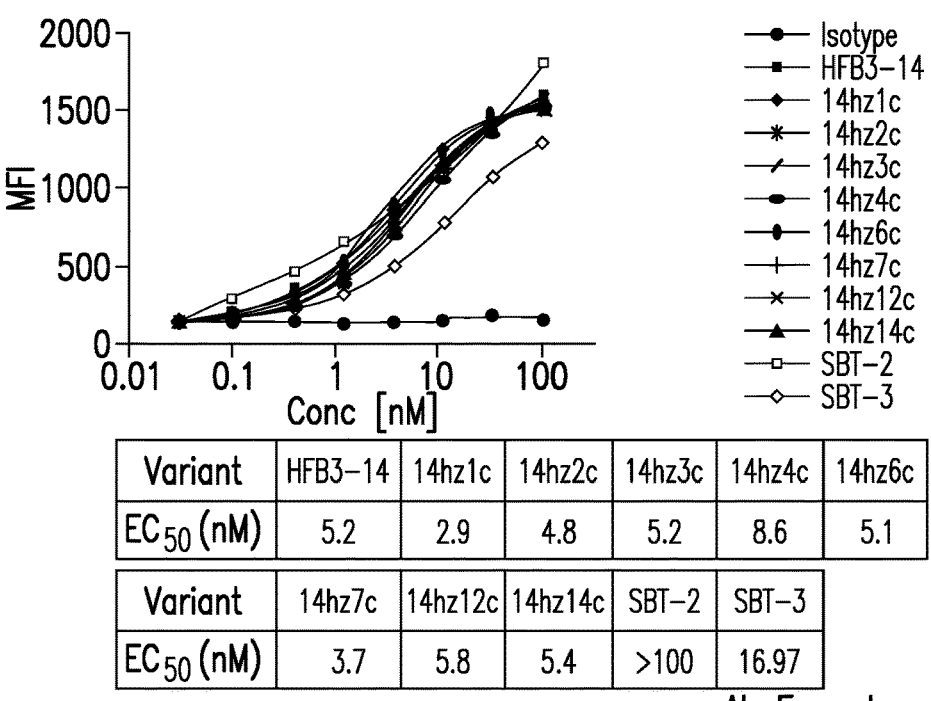
HFB3-14hz Selection
| Variant | HFB3-14 | 14hz1c | 14hz2c | 14hz3c | 14hz4c | 14hz6c |
|---------|---------|--------|--------|--------|--------|--------|
| EC$_{50}$ (nM) | 5.2 | 2.9 | 4.8 | 5.2 | 8.6 | 5.1 |
| Variant | 14hz7c | 14hz12c | 14hz14c | SBT-2 | SBT-3 |
|---------|--------|---------|---------|-------|-------|
| EC$_{50}$ (nM) | 3.7 | 5.8 | 5.4 | >100 | 16.97 |
mAb Format = IgG1AA
FIG.15

HFB3–14hz Selection

| | 7 And 14 d. Stability At 25 and 40 °C (PBS,pH 7.4) | 0, 3 and 6 h. Stability At Low pH (100 mM AcH pH 3.5, 25 °C) | Freeze/Thaw Stability (1, 2 and 3 Cycles) |
|---|---|---|---|
| HFB3–14hz1c–hG1AA | STABLE | STABLE | STABLE |
| HFB3–14hz2c–hG1AA | STABLE | STABLE | STABLE |
| HFB3–14hz3c–hG1AA | STABLE | STABLE | STABLE |
| HFB3–14hz4c–hG1AA | Degradation | Aggregation /Degradation | STABLE |

HFB3–1hz Selection

| | 7 And 14 d. Stability At 25 and 40 °C (PBS,pH 7.4) | 0, 3 and 6 h. Stability At Low pH (100 mM AcH pH 3.5, 25 °C) | Freeze/Thaw Stability (1, 2 and 3 Cycles) |
|---|---|---|---|
| HFB3–1hz4–hG1AA | STABLE | STABLE | STABLE |
| HFB3–1hz6–hG1AA | STABLE | STABLE | Precipitation After 3 Cycles |
| HFB3–1hz9–hG1AA | STABLE | STABLE | STABLE |
| HFB3–1hz10–hG1AA | STABLE | STABLE | Precipitation After 3 Cycles |
| HFB3–1hz11–hG1AA | STABLE | STABLE | STABLE |

FIG.18

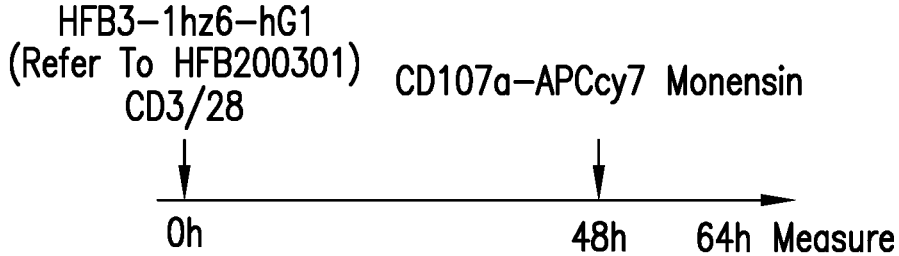
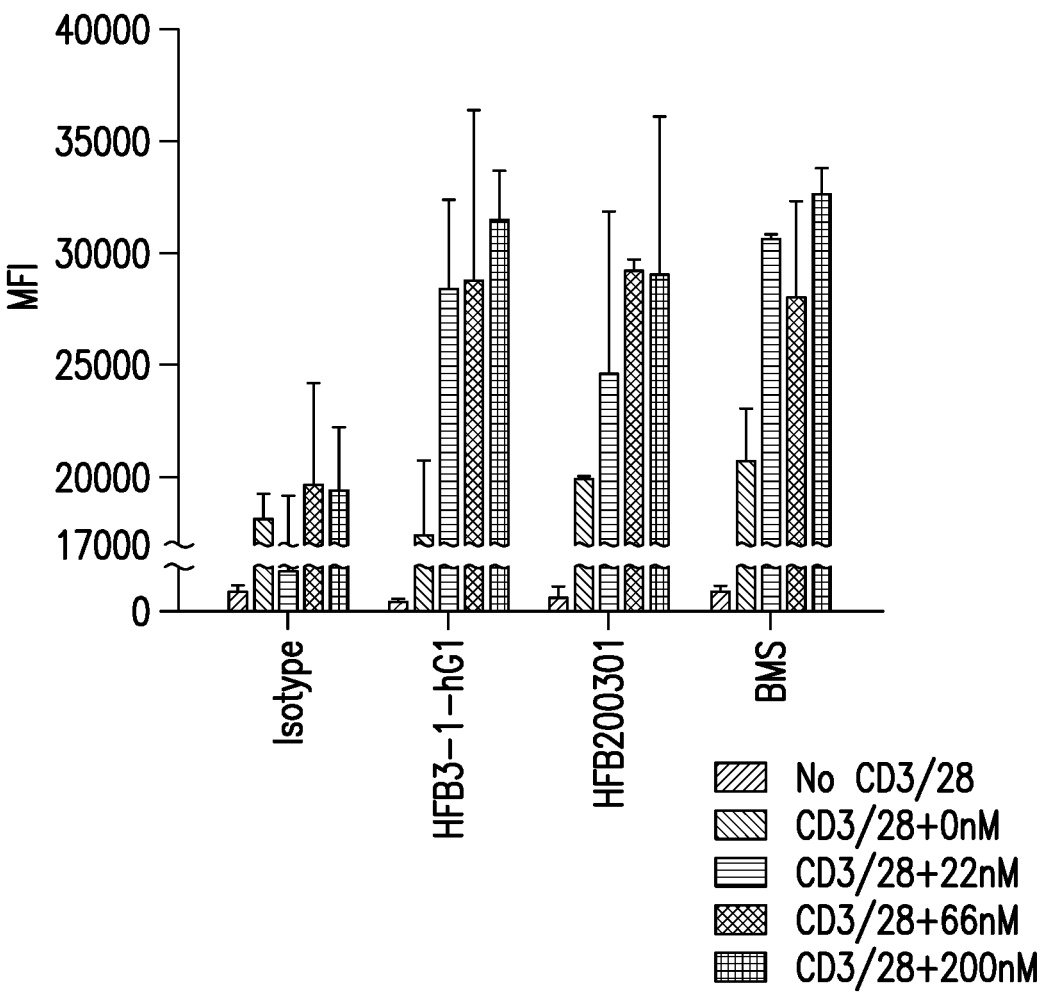
FIG.23

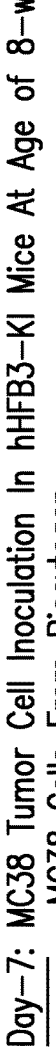
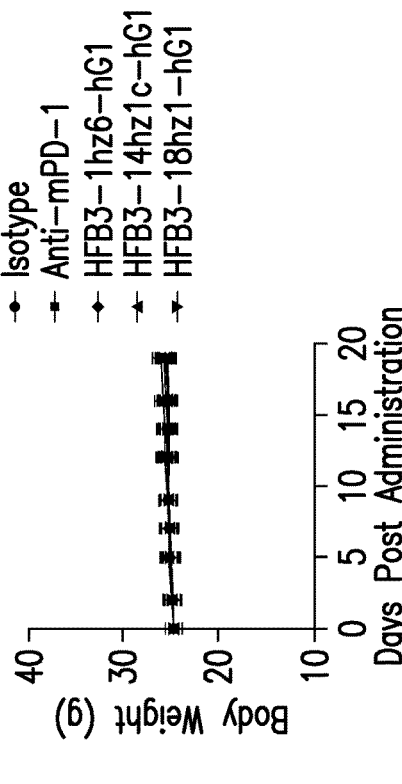
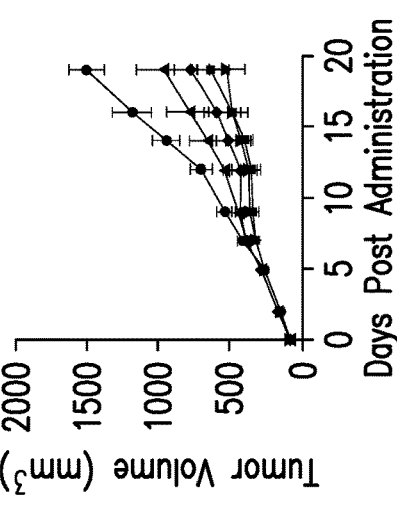

Day-7: MC38 Tumor Cell Inoculation In hHFB3-KI Mice At Age of 8-w
— MC38 Cells From Biocytogen
— Inoculate 5x10^5 Cells Per Mouse Day-0: The Average of Tumor Size Is 89mm³ (74-98mm3)
— 8x Mice Per Group; 5x Groups:
— Isotype (TT-hG1AA)
— Anti-mPD-1 (RMP1-14)
— HFB3-1hz6-hG1
— HFB3-14hz1c-hG1
— HFB3-18hz1-hG1

Day 28: Tumor Size of Isotype Ctrl Group Reached 2000mm³.
The Mice Were Sacrificed
Tissues: Tumor, Blood MC38 Inoculation D-7    D0    D3    D6    D9    D12  D15  D18    Dxx Q3Dx7, I.P. 10mg/kg Termination
Tumor>2000mm³

Isotype
Anti-mPD-1
HFB3-1hz6-hG1
HFB3-14hz1c-hG1
HFB3-18hz1-hG1

Body Weight (g)

Days Post Administration

Tumor Volume (mm³)

Days Post Administration

FIG.27A

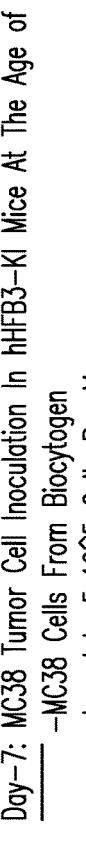
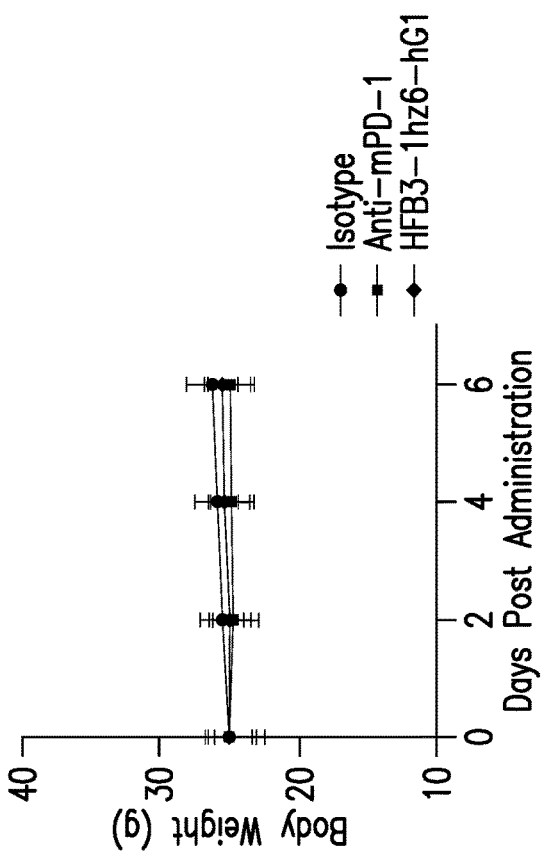
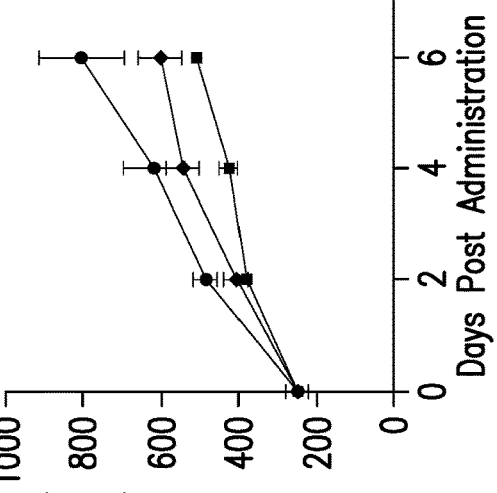
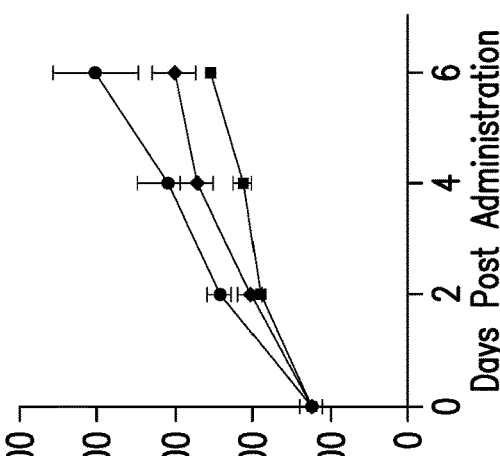
Day-7: MC38 Tumor Cell Inoculation In hHFB3-KI Mice At The Age of 8-W
  -MC38 Cells From Biocytogen
  -Inoculate 5x10^5 Cells Per Mouse
Day 0: The Average of Tumor Size is 89mm$^3$ (74-98mm3)
  -4x Mice Per Group; 3x Groups:
  -Isotype (TT-hG1AA)
  -Anti-mPD-1 (RMP1-14)
  --HFB3-1hz6-hG1
Day 7: The Mice Were Sacrificed And Tissue Harvested For PD Analysis
  Tissues: Tumor, Spleen, Plasma
FIG.28

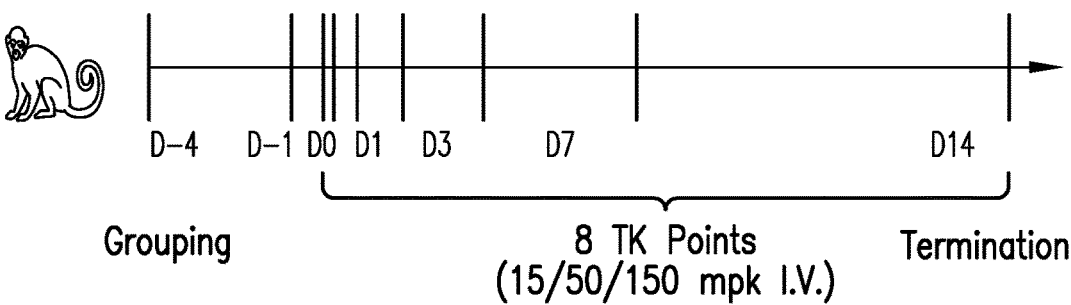
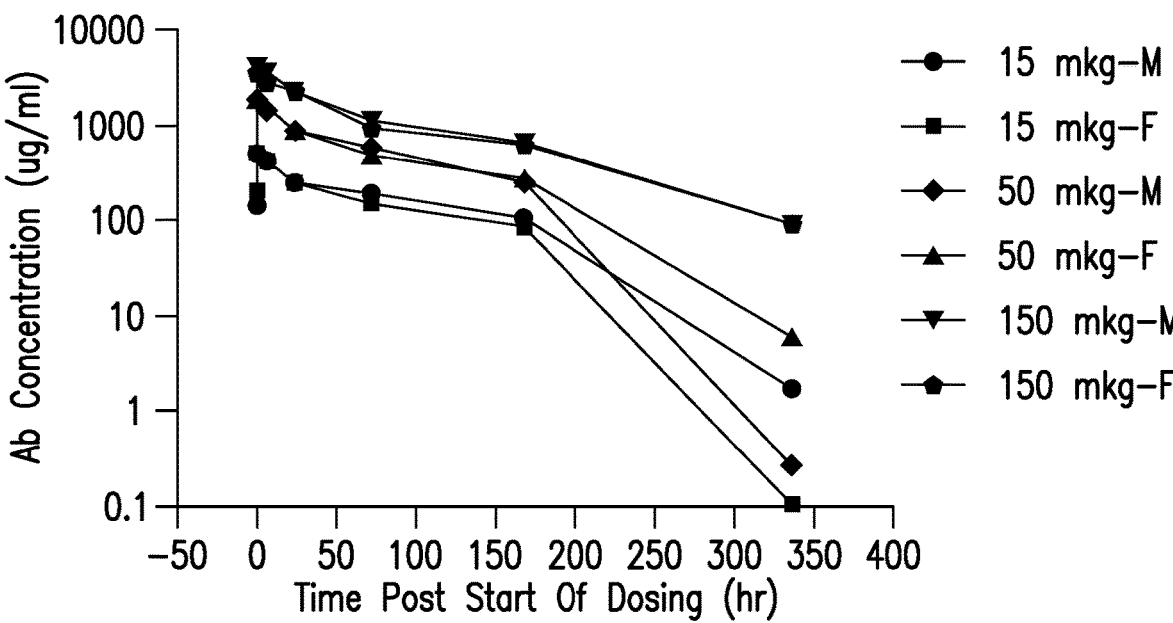
FIG.30

ANTI-TNFR2 ANTIBODY AND USES THEREOF

REFERENCE TO RELATED APPLICATIONS

This application is a U.S. national stage application filed under 35 U.S.C. § 371 (c), of International Patent Application No. PCT/US2021/012197, filed on Jan. 5, 2021, which claims the benefit of the filing dates of U.S. Provisional Patent Application Nos. 62/957,543, filed on Jan. 6, 2020, and 63/041,234, filed on Jun. 19, 2020, the entire contents of each of the above referenced applications including any drawings and sequence listings are incorporated herein by reference.

REFERENCE TO SEQUENCE LISTING

The present application is being filed along with a Sequence Listing in electronic format. The Sequence Listing file, entitled 131206-00103_SL, was created on Jul. 5, 2022, and is 95,567 bytes in size. The information in electronic format of the Sequence Listing is incorporated herein by reference in its entirety.

BACKGROUND OF THE INVENTION

Tumor Necrosis Factor Receptor 2 (TNFR2), also known as Tumor Necrosis Factor Receptor Superfamily Member 1B (TNFRSF1B) and CD120b, is a 75-kDa Type I trans-membrane protein which contains an extracellular domain (ECD, residues 1-257) with 4 cysteine-rich domains (CRD1 to CRD4), a transmembrane domain (TM, residues 258-287), and an intracellular domain (ICD, residues 288-461) with TRAF2-binding domain. TNFR2 share relatively low sequence identity with the other TNFα receptor—Tumor Necrosis Factor Receptor 1 (TNFR1), with the homology between their extracellular domains being only 28%.

TNFR2 binds to the TNFα ligand in a 3:3 trimerization mode. Co-crystal structure of TNFR2 with TNFα has been resolved, and it has been shown that each TNFR2 molecule binds to two TNFα ligands. In addition, TNFα binds TNFR2 with a $K_d$ of 420 pM, about 20 folds weaker than its binding to TNFR1 ($K_d$=19 nM). Naturally, TNFα preferentially binds to TNFR1 everything else being equal.

In normal T cells, TNFα-TNFR2 interaction triggers cell survival signals via the NFkB signaling pathway. In autoimmune T cells, however, TNFα-TNFR2 interaction triggers apoptosis signals via the caspase pathways.

Human TNFR2 shows 62% amino acid sequence homology with mouse TNFR2, but it is 97% identical to the rhesus monkey TNFR2.

While TNFR1 is ubiquitously expressed, TNFR2 expression is mainly restricted to immune cells, and is predominantly and highly expressed by tumor-infiltrating immunosuppressive CD4+FoxP3+ regulatory T cells (Tregs). Recent studies have shown that TNFR2 plays a crucial role in stimulating the activation and proliferation of Tregs, a major checkpoint of antitumor immune responses (Chen and Oppenheim, *Sci Signal* 10: eaal2328, 2017). Activation of TNFR2 via its ligand TNFα results in NFkB signaling activation and expansion of TNFR2+ Tregs. TNFR2 is also expressed in CD8 and CD4 Tconv cells, as well as myeloid cells. IN particular, TNFR2 is expressed in exhausted CD8 T cells, similarly to clinically validated immune-checkpoints.

T-regulatory cells (Tregs) are a small subset of T-lymphocytes with diverse clinical applications. On the one hand, TNFR2+ Tregs are highly immunosuppressive, with a suppressive activity more potent than that of highly suppressive CD103+ Tregs (*J Immunol* 179:154-161, 2007; *J Immunol* 180:6467-6471, 2008). Thus TNFR2+ Tregs can be used in therapy that depends on the immunosuppressive activity of Tregs, such as in transplantation, allergy, asthma, infectious diseases, graft versus host disease (GVHD), and autoimmunity. For example, in experimental GVHD mouse models, CD4+CD25$^{high}$Foxp3+ thymus-derived Treg depletion could intensify GVHD (Cohen et al., JEM 2002).

TNFR2 is also expressed in certain cancers, such as breast cancer, cervical cancer, colon cancer, and renal cancer (*Front. Immunol.* 9:1170, 2018), and may be involved in immunotolerance in these cancers. The survival and growth of these cancer cells are promoted by ligands of TNFR2 (TNFα). It has been shown that TNFR2 participates in various processes of tumor development by employing different signal pathways in tumor cells. For example, Nuclear Factor-κB (NFκB) is involved in TNFR2-related malignant transformation of epithelial cells. AKT signaling has been shown to be another mediator of TNFR2 in carcinogenesis, tumor growth, and angiogenesis. Meanwhile, Myosin Light-Chain Kinase (MLCK) and Extracellular signal-Regulated Kinase (ERK) are also important for the above-mentioned TNFR2 functions. Thus inhibiting TNFR2 function can inhibit Treg function and increase anti-tumor T cell response in immuno-oncology.

Thus, there is a need to develop therapeutic reagents that allow one to either enhance the immunosuppressive function of Tregs to treat autoimmune disorders through stimulating TNFR2 function on TNFR2+ Tregs, or to inhibit TNFR2 activation for treating diseases such as cancer.

SUMMARY OF THE INVENTION

In one aspect, the invention provides an isolated monoclonal antibody, or an antigen-binding fragment thereof, wherein said monoclonal antibody or antigen-binding fragment thereof is specific for human TNFR2, and wherein said monoclonal antibody comprises: (1a) a heavy chain variable region (HCVR), comprising a HCVR CDR1 sequence of SEQ ID NO: 1, a HCVR CDR2 sequence of SEQ ID NO: 2, and a HCVR CDR3 sequence of SEQ ID NO: 3; and, (1b) a light chain variable region (LCVR), comprising a LCVR CDR1 sequence of SEQ ID NO: 4, a LCVR CDR2 sequence of SEQ ID NO: 5, and a LCVR CDR3 sequence of SEQ ID NO: 6; or (2a) a heavy chain variable region (HCVR), comprising a HCVR CDR1 sequence of SEQ ID NO: 14, a HCVR CDR2 sequence of SEQ ID NO: 15, and a HCVR CDR3 sequence of SEQ ID NO: 16; and, (2b) a light chain variable region (LCVR), comprising a LCVR CDR1 sequence of SEQ ID NO: 17, a LCVR CDR2 sequence of SEQ ID NO: 18, and a LCVR CDR3 sequence of SEQ ID NO: 19; or (3a) a heavy chain variable region (HCVR), comprising a HCVR CDR1 sequence of SEQ ID NO: 26, a HCVR CDR2 sequence of SEQ ID NO: 27, and a HCVR CDR3 sequence of SEQ ID NO: 28; and, (3b) a light chain variable region (LCVR), comprising a LCVR CDR1 sequence of SEQ ID NO: 29, a LCVR CDR2 sequence of SEQ ID NO: 30, and a LCVR CDR3 sequence of SEQ ID NO: 31; or (4a) a heavy chain variable region (HCVR), comprising a HCVR CDR1 sequence of SEQ ID NO: 39, a HCVR CDR2 sequence of SEQ ID NO: 40, and a HCVR CDR3 sequence of SEQ ID NO: 41; and, (4b) a light chain variable region (LCVR), comprising a LCVR CDR1 sequence of SEQ ID NO: 42, a LCVR CDR2 sequence of SEQ ID NO: 43, and a LCVR CDR3 sequence of SEQ ID NO: 44; or (5a) a heavy chain variable region (HCVR), comprising a HCVR CDR1 sequence of SEQ ID NO: 51, a HCVR CDR2 sequence of SEQ ID NO: 52, and a HCVR CDR3 sequence of SEQ ID NO: 53; and, (5b) a light chain variable region (LCVR), comprising a LCVR CDR1 sequence of SEQ ID NO: 54, a LCVR CDR2 sequence of SEQ ID NO: 55, and a LCVR CDR3 sequence of SEQ ID NO: 56; or (6a) a heavy chain variable region (HCVR), comprising a HCVR CDR1 sequence of SEQ ID NO: 63, a HCVR CDR2 sequence of SEQ ID NO: 64, and a HCVR CDR3 sequence of SEQ ID NO: 65; and, (6b) a light chain variable region (LCVR), comprising a LCVR CDR1 sequence of SEQ ID NO: 66, a LCVR CDR2 sequence of SEQ ID NO: 67, and a LCVR CDR3 sequence of SEQ ID NO: 68.

In certain embodiments, in the isolated monoclonal antibody or antigen-binding fragment thereof, (1A) the HCVR sequence is SEQ ID NO: 7; and/or, (1B) the LCVR sequence is SEQ ID NO: 8, or, (2A) the HCVR sequence is SEQ ID NO: 20; and/or, (2B) the LCVR sequence is SEQ ID NO: 21, or, (3A) the HCVR sequence is SEQ ID NO: 32; and/or, (3B) the LCVR sequence is SEQ ID NO: 33, or, (4A) the HCVR sequence is SEQ ID NO: 45; and/or, (4B) the LCVR sequence is SEQ ID NO: 46, or, (5A) the HCVR sequence is SEQ ID NO: 57; and/or, (5B) the LCVR sequence is SEQ ID NO: 58, or, (6A) the HCVR sequence is SEQ ID NO: 69; and/or, (6B) the LCVR sequence is SEQ ID NO: 70.

In certain embodiments, the monoclonal antibody has: (1a) a heavy chain sequence of SEQ ID NO: 9; and/or, (1b) a light chain sequence of SEQ ID NO: 10, or, (2a) a heavy chain sequence of SEQ ID NO: 22; and/or, (2b) a light chain sequence of SEQ ID NO: 23, or, (3a) a heavy chain sequence of SEQ ID NO: 34; and/or, (3b) a light chain sequence of SEQ ID NO: 35, or, (4a) a heavy chain sequence of SEQ ID NO: 47; and/or, (4b) a light chain sequence of SEQ ID NO: 48, or, (5a) a heavy chain sequence of SEQ ID NO: 59; and/or, (5b) a light chain sequence of SEQ ID NO: 60, or, (6a) a heavy chain sequence of SEQ ID NO: 71; and/or, (6b) a light chain sequence of SEQ ID NO: 72.

In certain embodiments, the isolated monoclonal antibody or antigen-binding fragment thereof is a human-mouse chimeric antibody, a humanized antibody, a human antibody, a CDR-grafted antibody, or a resurfaced antibody.

In certain embodiments, the antigen-binding fragment thereof is an Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

In certain embodiments, the monoclonal antibody or antigen-binding fragment thereof cross-reacts with rhesus monkey TNFR2, but does not substantially cross-react with mouse TNFR2.

In certain embodiments, the monoclonal antibody or antigen-binding fragment thereof of the invention includes one or more point mutations of its amino acid sequence that are designed to improve developability of the antibody. For example, in certain embodiments, the one or more point mutations make the antibody more stable during its expression in a host cell, its purification during the manufacturing, and/or the formulation processes, and/or its administration to a subject patient. In certain embodiments, the one or more point mutations make the antibody less likely to aggregate during the manufacturing and/or formulation processes.

In certain embodiments, the invention provides a therapeutic antibody with minimized or reduced developability issues, such as removed or reduced hydrophobicity and/or optimized charges by replacing one or more amino acids in its sequence (e.g., in one or more of its CDRs).

In certain embodiments, the monoclonal antibody or antigen-binding fragment thereof does not substantially cross-react with TNFR1.

In certain embodiments, the monoclonal antibody or antigen-binding fragment thereof binds TNFα with a Kd of less than about 25 nM, 20 nM, 15 nM, 10 nM, 5 nM, 2 nM, or 1 nM.

In certain embodiments, the isolated monoclonal antibody or antigen-binding fragment thereof enhances binding between TNFα and TNFR2; enhances TNFα-mediated or -co-stimulated NFκB signaling (e.g., in TCR-activated CD8 and/or CD4 Tconv T cells); and/or promotes TCR-activated effector T cell (e.g., CD8 and/or CD4 Tconv T cell) proliferation in the presence of Treg.

In certain embodiments, the isolated monoclonal antibody or antigen-binding fragment thereof enhances TNFα-mediated CD25 expression on Tregs.

In certain embodiments, the isolated monoclonal antibody or antigen-binding fragment thereof binds to an epitope of SEQ ID NO: 13.

In certain embodiments, the isolated monoclonal antibody or antigen-binding fragment thereof promotes TNFα binding to TNFR2; inhibits TNFα binding to TNFR2; or has no apparent effect on TNFα binding to TNFR2.

In certain embodiments, the isolated monoclonal antibody or antigen-binding fragment thereof does not block, inhibit, or otherwise substantially antagonize TNFα binding to TNFR2.

In certain embodiments, the isolated monoclonal antibody or antigen-binding fragment thereof is an agonist of TNFR2, or stimulates TNFR2 signaling (such as in the presence of TNFα), wherein the agonist function is preferably Fc-independent.

In certain embodiments, the isolated monoclonal antibody or antigen-binding fragment thereof activates CD4$^+$ effector T cells, CD8$^+$ effector T cells, other effector T cells, and/or NK cells in vitro.

Another aspect of the invention provides an isolated monoclonal antibody or an antigen-binding fragment thereof, which competes with the isolated monoclonal antibody or antigen-binding fragment thereof of any one of the subject antibodies for binding to the epitope of SEQ ID NO: 13.

Another aspect of the invention provides an isolated monoclonal antibody or an antigen-binding fragment thereof, which specifically binds to the epitope of SEQ ID NO: 13.

In certain embodiments, the isolated monoclonal antibody or antigen-binding fragment thereof enhances binding between TNFα and TNFR2; enhances TNFα-mediated or -co-stimulated NFκB signaling (e.g., in TCR-activated CD8 and/or CD4 Tconv T cells); and/or promotes TCR-activated effector T cell (e.g., CD8 and/or CD4 Tconv T cell) proliferation in the presence of Treg.

In certain embodiments, the isolated monoclonal antibody or antigen-binding fragment thereof inhibits binding between TNFα and TNFR2; inhibits TNFα-mediated or -co-stimulated NFκB signaling (e.g., in TCR-activated CD8 and/or CD4 Tconv T cells); and/or inhibits TCR-activated effector T cell (e.g., CD8 and/or CD4 Tconv T cell) proliferation in the presence of Treg.

In certain embodiments, the isolated monoclonal antibody or antigen-binding fragment thereof promotes Treg expansion.

Another aspect of the invention provides an isolated monoclonal antibody or an antigen-binding fragment thereof, which competes with the isolated monoclonal antibody or antigen-binding fragment thereof of the invention for binding to the same epitope.

Another aspect of the invention provides a method of treating cancer, or autoimmune disorder (AID, such as GVHD (graft-vs-host disease) and Rheumatoid Arthritis) in a patient in need thereof, the method comprising administering to the patient an effective amount of the isolated monoclonal antibody or antigen-binding fragment thereof of the invention.

In certain embodiments, the method is for treating AID, wherein the method further comprises administering a second agent, such as low dose anti-IL2 agent in treating chronic GVHD, or an anti-TNFα agent (such as adalimumab, infliximab, etenercept, golimumab, etc) in treating rheumatoid arthritis, chronic plaque psoriasis, Crohn's disease, ankylosing spondylitis, psoriatic arthritis, polyarticular juvenile idiopathic arthritis, IBS, EAE, and non-infectious uveitis.

In certain embodiments, the method is for treating cancer, wherein the method further comprises administering an antagonist of an immune checkpoint.

In certain embodiments, the immune checkpoint is PD-1/PD-L1 immune checkpoint.

In certain embodiments, the antagonist of the immune checkpoint is an antibody or antigen-binding fragment thereof specific for PD-1 or PD-L1.

In certain embodiments, the antibody is an anti-PD-1 antibody, such as cemiplimab, nivolumab, or pembrolizumab.

In certain embodiments, the antibody is an anti-PD-L1 antibody, such as avelumab, durvalumab, atezolizumab, KN035, or CK-301.

In certain embodiments, the antagonist of the immune checkpoint is a (non-antibody) peptide inhibitor of PD-1/PD-L1, such as AUNP12; a small molecule inhibitor of PD-L1 such as CA-170, or a macrocyclic peptide such as BMS-986189.

In certain embodiments, the cancer is breast cancer, colon cancer, cervical cancer, renal cancer, liver cancer (e.g., heptocellular carcinoma), lung cancer (e.g., NSCLC), ovarian cancer, melanoma, skin cancer (e.g., squamous cell carcinoma or basal cell carcinoma), lymphoma, or leukemia. In certain embodiments, the cancer is melanoma.

In certain embodiments, the method further comprises administering to the patient a chemotherapeutic agent, an anti-angiogenesis agent, a growth inhibitory agent, an immune-oncology agent, and/or an anti-neoplastic composition.

Another aspect of the invention provides a polynucleotide encoding the heavy chain or the light chain or the antigen-binding portion thereof of the invention.

In certain embodiments, the polynucleotide is codon optimized for expression in a human cell.

Another aspect of the invention provides a vector comprising the polynucleotide of the invention.

In certain embodiments, the vector is an expression vector (e.g., a mammalian expression vector, a yeast expression vector, an insect expression vector, or a bacterial expression vector).

BRIEF DESCRIPTION OF THE DRAWINGS

FIG. 1 shows sequence alignments for the VH and VL regions of human-mouse chimeric monoclonal antibodies HFB3-1, -3, -6, -14, -18, -19, -20, -21, -22, -23, -24, and HFB3-25, as well as the consensus sequences thereof.

FIG. 2B shows that different anti-TNFR2 monoclonal antibodies may promote (HFB3-1) or inhibit (HFB3-18) TNFα binding to TNFR2, or have no effect (HFB3-6) on the binding.

FIG. 3 shows no binding of the human-mouse chimeric monoclonal antibodies to the parental CHO cell line, and no binding to CHO cells expressing mouse TNFR2 (except for marginal binding by HFB3-18 and HFB3-19 antibodies).

FIG. 4A shows binding specificity of the human-mouse chimeric antibodies specifically towards TNFR2 but not TNFR1.

FIG. 4B shows $K_d$, $k_{on}$ and $k_{off}$ values of human-mouse chimeric antibodies, HFB3-1, -14 and -18, to His-tagged recombinant human TNFR2.

FIG. 5 shows expression of TNFR2 on T cell subtypes in tumor infiltrating lymphocytess, particularly exhausted CD8 T cells.

FIG. 11A and FIG. 11B show various features of the His-tagged extracellular domain (ECD) of TNFR2 (referred to as HFB2003), including TNFα binding sites, and results of epitope mapping for the monoclonal antibodies HFB3-1 and HFB3-14, as well as either HFB3-18 (FIG. 11A) or HFB3-6 (FIG. 11B). These are mouse chimeric antibodies with human IgG1 Fc region, and are thus also referred to as HFB3-1-hG1, HFB3-14-hG1, HFB3-18-hG1, or HFB3-6-hG1, respectively. FIG. 11B also includes epitope mapping data for benchmark antibodies SBT-1 and SBT-4 (benchmark 1 and 2). The HFB3-1 antibody binds to the CRD2 region of the ECD, HFB3-14 and HFB3-6 bind to the CRD3 region of the ECD, while HFB3-18 binds to the CRD1 region of the ECD.

FIG. 11C provides 3-D models showing binding sites of HFB3-1, HFB3-14, HFB3-6, as well as HFB-3-18 on TNFR2-TNFα complex.

FIG. 14B shows results of binding affinity towards recombinant human TNFR2 by humanized variants and the parental chimeric monoclonal antibodies HFB3-1 and -14, based on AHC (Anti-Human IgG Fc Capture) biosensor measurements. Values were averages of two experiments obtained from two different days.

FIG. 15 shows cellular binding of humanized anti-TNFR2 monoclonal antibodies to TCR-activated CD8 T cells.

FIG. 18 shows that the subject humanized variant anti-TNFR2 antibodies are stable in storage.

FIG. 23 shows ex vivo activation of natural killer (NK) cells in whole peripheral blood mononuclear cell fraction by HFB3-1hz6-hG1 and parental mouse HFB3-1-hG1 after stimulation with plate-bound anti-CD3 (1 μg/mL) and soluble anti-CD28 (1 μg/mL). Timeline of the experiment is shown in the top panel. Among $CD3^-/CD56^+$ cells, CD107a expression was up-regulated by HFB3-1hz6-hG1 and HFB3-1-hG1 in a dose dependent manner, but control anti-OX40 antibody (MBS) is unable to trigger short-term NK activation.

FIG. 27A and FIG. 27B show that the humanized monoclonal antibodies such as HFB3-1hz6 and HFB3-18hz1 have similar therapeutic efficacy as compared to that of the rat anti-mPD-1 monoclonal antibody.

FIG. 28 shows that the humanized HFB3-1hz6 monoclonal antibody has therapeutic efficacy, as does the mouse anti-mPD-1 monoclonal antibody.

DETAILED DESCRIPTION OF THE INVENTION

1. Overview

Figure 2A:
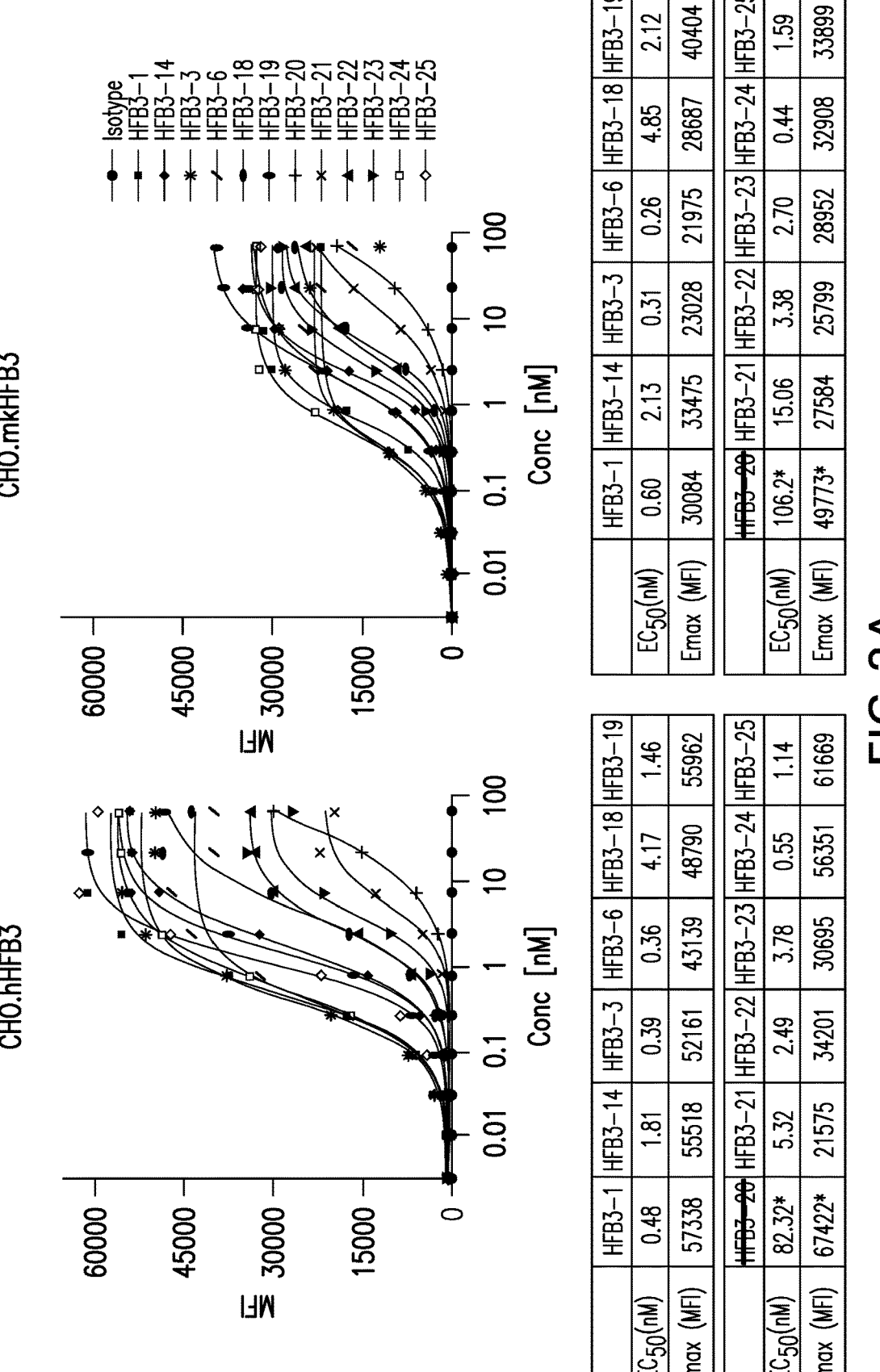
FIG. 2A shows binding affinity of selected human-mouse chimeric monoclonal antibodies raised against the extracellular domain of recombinant human TNFR2. $EC_{50}$ and $E_{max}$ values for the test antibodies and isotype matched negative control antibody were measured against CHO cells expressing human TNFR2 (CHO.bHFB3) or rhesus monkey TNFR2 (CHO.mkHFB3).

TNFR2 has recently emerged as a promising therapeutic target for Immuno-Oncology. TNFR2 expression on regulatory and effector T cells in the tumor microenvironment (TME) has been associated with T cell exhaustion and resistance to immune-checkpoint blockade. The invention described herein provides antibodies against human TNFR2 that can be used as anti-cancer agents. While not wishing to be bound by any particular theory, it is believed that co-stimulation of effector T cells with the subject anti-TNFR2 antibodies enhances the anti-tumor activity of the effector T cells.

According to the invention described herein, mice were immunized with the recombinant extracellular domain (ECD) of human TNFR2 (rhTNFR2) to produce a series of diverse antibodies that were characterized for binding, cross-reactivity, selectivity and functional activity. The antibodies were selected for their ability to induce CD8$^+$ and CD4$^+$ effector T cell proliferation in the presence of Treg cells, and for increased NFkB signaling. The selected antibodies also desirably showed cross-reactivity against the monkey ortholog of rhTNFR2, which would be a beneficial feature for toxicity study of a human therapeutic agent in animal. Further desired features include the ability of the subject antibodies to enhance the binding of human recombinant TNFα to TNFR2.

Two mouse antibodies, HFB3-1 and HFB3-14, with sub- or single-digit-nanomolar binding affinities for human TNFR2, were initially selected for further characterization and humanization. Epitope mapping experiments showed that these two antibodies recognize different domains of TNFR2, with HFB3-1 binding to a region within the CRD2 domain, and HFB3-14 binding within the CRD3 region. Despite their different binding sites, however, both antibodies are selective for TNFR2, cross-react with cynomolgus and rhesus monkey orthologs, and enhance the binding of human recombinant TNFα to TNFR2, as well as stimulate CD8 and conventional CD4 T cells (Tconv).

Several humanized variants of these mouse antibodies, including HFB3-1hz6 and HFB3-14hz1c, retained the binding and cross-reactivity profiles of their respective parental antibodies. The humanized antibodies preferentially bind to TCR-activated primary CD8 and CD4 T cells as compared to unstimulated T cells, and enhance CD3/CD28-induced activation and proliferation of T cells. This co-stimulatory mechanism of action is cross-linking independent, and is consistent with the antibodies' ability to enhance NFκB signaling and induce upregulation of NFκB downstream target genes.

Further, both humanized antibodies (HFB3-1hz6 and HFB3-14hz1c) demonstrated good developability profile and are stable under high temperature, low pH conditions and following several freeze/thaw cycles. Good plasma exposures for lead antibodies were also observed in mice models. The in vivo efficacy evaluation of these antibodies in mouse tumor models as well as initial toxicity analysis are being conducted.

A third mouse monoclonal antibody, HFB3-18, with slightly lower (double-digit nM) binding affinity but same if not better ability than the anti-mPD-1 monoclonal antibody to inhibit tumor growth in vivo, was also identified and its humanized versions generated.

The functional profile of these antibodies along with their favorable developability and pharmacokinetic profiles support their development as a potential novel immune-therapeutic option for cancer patients.

Detailed aspects of the invention are described further and separately in the various sections below. However, it should be understood that any one embodiment of the invention, including embodiments described only in the examples or drawings, and embodiments described only under one section below, can be combined with any other embodiment(s) of the invention.

2. Definitions

The term "antibody," in the broadest sense, encompasses various antibody structures, including but not limited to monoclonal antibodies, polyclonal antibodies, and multispecific antibodies (e.g., bispecific antibodies). The term "antibody" may also broadly refers to a molecule comprising complementarity determining region (CDR) 1, CDR2, and CDR3 of a heavy chain and CDR1, CDR2, and CDR3 of a light chain, wherein the molecule is capable of binding to an antigen. The term "antibody" also includes, but is not limited to, chimeric antibodies, humanized antibodies, human antibodies, and antibodies of various species such as mouse, human, cynomolgus monkey, etc.

In a narrower sense, however, "antibody" refers to the various monoclonal antibodies, including chimeric monoclonal antibodies, humanized monoclonal antibodies, and human monoclonal antibodies, particularly humanized monoclonal antibodies of the invention.

In some embodiments, an antibody comprises a heavy chain variable region (HCVR) and a light chain variable region (LCVR). In some embodiments, an antibody comprises at least one heavy chain (HC) comprising a heavy chain variable region and at least a portion of a heavy chain constant region, and at least one light chain (LC) comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region.

As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

The term "heavy chain variable region (HCVR)" as used herein refers to, at a minimum, a region comprising heavy chain CDR1 (CDR-H1), framework 2 (HFR2), CDR2 (CDR-H2), FR3 (HFR3), and CDR3 (CDR-H3). In some embodiments, a heavy chain variable region also comprises at least a portion (e.g., the whole) of an FR1 (HFR1), which is N-terminal to CDR-H1, and/or at least a portion (e.g., the whole) of an FR4 (HFR4), which is C-terminal to CDR-H3.

The term "heavy chain constant region" as used herein refers to a region comprising at least three heavy chain constant domains, CH1, CH2, and CH3. Non-limiting exemplary heavy chain constant regions include γ, δ, and α. Non-limiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, an antibody comprising an α constant region is an IgA antibody, an antibody comprising an ε constant region is an IgE antibody, and an antibody comprising an μ constant region is an IgM antibody.

Certain isotypes can be further subdivided into subclasses. For example, IgG antibodies include, but are not limited to, IgG1 (comprising a γ1 constant region), IgG2 (comprising a γ2 constant region), IgG3 (comprising a γ3 constant region), and IgG4 (comprising a γ4 constant region) antibodies; IgA antibodies include, but are not limited to, IgA1 (comprising an a1 constant region) and IgA2 (comprising an α2 constant region) antibodies; and IgM antibodies include, but are not limited to, IgM1 (comprising an µ1 constant region) and IgM2 (comprising an µ2 constant region).

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence, and with or without a C-terminal lysine.

The term "light chain variable region (LCVR)" as used herein refers to a region comprising light chain CDR1 (CDR-L1), framework (FR) 2 (LFR2), CDR2 (CDR-L2), FR3 (LFR3), and CDR3 (CDR-L3). In some embodiments, a light chain variable region also comprises at least a portion (e.g., the whole) of an FR1 (LFR1) and/or at least a portion (e.g., the whole) of an FR4 (LFR4).

The term "light chain constant region" as used herein refers to a region comprising a light chain constant domain, $C_L$. Non-limiting exemplary light chain constant regions include λ and κ.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

The term "antibody fragment" or "antigen binding portion" (of antibody) includes, but is not limited to, fragments that are capable of binding antigen, such as Fv, single-chain Fv (scFv), Fab, Fab', and (Fab')₂. In certain embodiments, an antibody fragment includes Fab, Fab', F(ab')₂, $F_d$, single chain Fv or scFv, disulfide linked Fv, V-NAR domain, IgNar, intrabody, IgGΔCH₂, minibody, F(ab')₃, tetrabody, triabody, diabody, single-domain antibody, DVD-Ig, Fcab, mAb₂, (scFv)₂, or scFv-Fc.

The term "Fab" refers to an antibody fragment with a molecular mass of approximately 50,000 Daltons, and has an activity of binding to the antigen. It comprises approximately half of the N-terminal side of the heavy chain and the whole of the light chain connected by a disulfide bridge. The Fab can be obtained in particular by treatment of immunoglobulin by a protease, papain.

The term "F(ab')₂" designates a fragment of approximately 100,000 Daltons and an activity of binding to the antigen. This fragment is slightly larger than two Fab fragments connected via a disulfide bridge in the hinge region. These fragments are obtained by treating an immunoglobulin with a protease, pepsin. The Fab fragment can be obtained from the F(ab')₂ fragment by cleaving of the disulfide bridge of the hinge region.

A single Fv chain "scFv" corresponds to a VH:VL polypeptide synthesized using the genes coding for the VL and VH domains and a sequence coding for a peptide intended to bind these domains. An scFv according to the invention includes the CDRs maintained in an appropriate conformation, for example using genetic recombination techniques.

The dimers of "scFv" correspond to two scFv molecules connected together by a peptide bond. This Fv chain is frequently the result of the expression of a fusion gene including the genes coding for VH and VL connected by a linker sequence coding a peptide. The human scFv fragment may include CDR regions that are maintained in an appropriate conformation, preferably by means of the use of genetic recombination techniques.

The "dsFv" fragment is a VH-VL heterodimer stabilized by a disulfide bridge; it may be divalent (dsFV₂). Fragments of divalent Sc(Fv)₂ or multivalent antibodies may form spontaneously by the association of monovalent scFvs or be produced by connecting scFvs fragments by peptide binding sequences.

The Fc fragment is the support for the biological properties of the antibody, in particular its ability to be recognized by immunity effectors or to activate the complement. It consists of constant fragments of the heavy chains beyond the hinge region.

The term "diabodies" signifies small antibody fragments having two antigen fixing sites. These fragments comprise, in the same VH-VL polypeptide chain, a variable heavy chain domain VH connected to a variable light chain domain VL. Using a binding sequence that is too short to allow the matching of two domains of the same chain, the matching with two complementary domains of another chain necessarily occurs and thus two antigen fixing sites are created.

An "antibody that binds to the same epitope" as a reference antibody can be determined by an antibody competition assay. It refers to an antibody that blocks binding of the reference antibody to its antigen in a competition assay by 50% or more, and conversely, the reference antibody blocks binding of the antibody to its antigen in a competition assay by 50% or more. The term "compete" when used in the context of an antibody that compete for the same epitope means competition between antibodies is determined by an assay in which an antibody being tested prevents or inhibits specific binding of a reference antibody to a common antigen.

Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619); solid phase direct labeled assay; solid phase direct labeled sandwich assay (see, e.g., Harlow and Lane, 1988, Antibodies, A Laboratory Manual, Cold Spring Harbor Press); solid phase direct label RIA using $I^{125}$ label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol.).

Typically, such an assay involves the use of purified antigen bound to a solid surface or cells bearing either of these, an unlabeled test antigen binding protein and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibodies and antibodies binding to an adjacent epitope sufficiently proximal to the epitope bound by the reference antibody for steric hindrance to occur. In some embodiments, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antibody or immunologically functional fragment thereof, and additionally capable of being used in a mammal to produce antibodies capable of binding to that antigen. An antigen may possess one or more epitopes that are capable of interacting with antibodies.

The term "epitope" is the portion of an antigen molecule that is bound by a selective binding agent, such as an antibody or a fragment thereof. The term includes any determinant capable of specifically binding to an antibody. An epitope can be contiguous or non-contiguous (e.g., in a polypeptide, amino acid residues that are not contiguous to one another in the polypeptide sequence but that within in context of the molecule are bound by the antigen binding protein). In some embodiments, epitopes may be mimetic in that they comprise a three dimensional structure that is similar to an epitope used to generate the antibody, yet comprise none or only some of the amino acid residues found in that epitope used to generate the antibody. Epitope determinants may include chemically active surface groupings of molecules such as amino acids, sugar side chains, phosphoryl or sulfonyl groups, and may have specific three dimensional structural characteristics, and/or specific charge characteristics.

In some embodiments, an "epitope" is defined by the method used to determine it. For example, in some embodiments, an antibody binds to the same epitope as a reference antibody, if they bind to the same region of the antigen, as determined by hydrogen-deuterium exchange (HDX).

In certain embodiments, an antibody binds to the same epitope as a reference antibody if they bind to the same region of the antigen, as determined by X-ray crystallography.

A "chimeric antibody" as used herein refers to an antibody comprising at least one variable region from a first species (such as mouse, rat, cynomolgus monkey, etc.) and at least one constant region from a second species (such as human, cynomolgus monkey, chicken, etc.). In some embodiments, a chimeric antibody comprises at least one mouse variable region and at least one human constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region (such as mouse, rat, cynomolgus monkey, chicken, etc.) has been replaced with the corresponding amino acid from a human variable region. In some embodiments, a humanized antibody comprises at least one human constant region or fragment thereof. In some embodiments, a humanized antibody fragment is an Fab, an scFv, a (Fab')$_2$, etc.

A "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XENOMOUSE®, and antibodies selected using in vitro methods, such as phage display, wherein the antibody repertoire is based on a human immunoglobulin sequences.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Non-limiting exemplary mammalian cells include, but are not limited to, NSO cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature or has been separated from at least some of the components with which it is typically produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to a mammal such as human. In some embodiments, methods of treating other non-human mammals, including, but not limited to, rodents, simians, felines, canines, equines, bovines, porcines, ovines, caprines, mammalian laboratory animals, mammalian farm animals, mammalian sport animals, and mammalian pets, are also provided. In some instances, a "subject" or "patient" refers to a (human) subject or patient in need of treatment for a disease or disorder.

The term "sample" or "patient sample" as used herein, refers to material that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as sputum, cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample," "reference cell," or "reference tissue," as used herein, refers to a sample, cell or tissue obtained from a source known, or believed, not to be afflicted with the disease or condition for which a method or composition of the invention is being used to identify. In one embodiment, a reference sample, reference cell or reference tissue is obtained from a healthy part of the body of the same subject or patient in whom a disease or condition is being identified using a composition or method of the invention. In one embodiment, a reference sample, reference cell or reference tissue is obtained from a healthy part of the body of at least one individual who is not the subject or patient in whom a disease or condition is being identified using a composition or method of the invention. In some embodiments, a reference sample, reference cell or reference tissue was previously obtained from a patient prior to developing a disease or condition or at an earlier stage of the disease or condition.

A "disorder" or "disease" is any condition that would benefit from treatment with one or more Gal-9 antagonists of the invention. This includes chronic and acute disorders or diseases including those pathological conditions that predispose the mammal to the disorder in question. Non-limiting examples of disorders to be treated herein include cancers.

An "illness associated with the suppressor activity of regulatory T lymphocytes" means any illness (not autoimmune) in which the suppressor activity of regulatory T lymphocytes plays a role, in particular by promoting the development or persistence of the illness. In particular, it has been demonstrated that the suppressor activity of regulatory T lymphocytes promotes the development of tumors. The invention therefore aims more particularly at cancers in which the suppressor activity of T lymphocytes plays a role.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells (i.e., forming solid tumors) or leukemic cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

In certain embodiments, cancer as used herein includes a hematological cancer (such as AML and DLBCL), or a solid tumor (such as breast cancer, head and neck cancer, lung cancer, melanoma (including uveal melanoma), colon cancer, renal carcinoma, ovarian cancer, liver cancer, and prostate cancer).

A "chemotherapeutic agent" is a chemical compound that can be useful in the treatment of cancer. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma11 and calicheamicin omega11 (see, e.g., Agnew, Chem Intl. Ed. Engl, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophorfree, albumin-engineered nanoparticle formulation of paclitaxel (American Pharmaceutical Partners, Schaumberg, Illinois), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further non-limiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxy tamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (AVASTIN)) or to the VEGF-A receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENT®/SU1 1248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) Annu. Rev. Physiol. 53:217-39; Streit and Detmar (2003) Oncogene 22:3172-3179 (e.g., Table 3 listing anti-angiogenic therapy in malignant melanoma); Ferrara & Alitalo (1999) Nature Medicine 5(12): 1359-1364; Tonini et al. (2003) Oncogene 22:6549-6556 (e.g., Table 2 listing known anti-angiogenic factors); and, Sato (2003) Int. J. Clin. Oncol. 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "anti-neoplastic composition" refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, cancer immunotherapeutic agents (also referred to as immuno-oncology agents), apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), VISTA inhibitors (e.g., anti-VISTA antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, VISTA, or VEGF receptor(s), TRAIL/Apo2, and other bioactive and organic chemical agents, etc. Combinations thereof are also included in the invention.

"Treatment" refers to therapeutic treatment, for example, wherein the object is to slow down (lessen) the targeted pathologic condition or disorder as well as, for example, wherein the object is to inhibit recurrence of the condition or disorder. "Treatment" covers any administration or application of a therapeutic for a disease (also referred to herein as a "disorder" or a "condition") in a mammal, including a human, and includes inhibiting the disease or progression of the disease, inhibiting or slowing the disease or its progression, arresting its development, partially or fully relieving the disease, partially or fully relieving one or more symptoms of a disease, or restoring or repairing a lost, missing, or defective function; or stimulating an inefficient process. The term "treatment" also includes reducing the severity of any phenotypic characteristic and/or reducing the incidence, degree, or likelihood of that characteristic. Those in need of treatment include those already with the disorder as well as those at risk of recurrence of the disorder or those in whom a recurrence of the disorder is to be prevented or slowed down.

The term "effective amount" or "therapeutically effective amount" refers to an amount of a drug effective to treat a disease or disorder in a subject. In some embodiments, an effective amount refers to an amount effective, at dosages and for periods of time necessary, to achieve the desired therapeutic or prophylactic result. A therapeutically effective amount of the antibodies of the invention may vary according to factors such as the disease state, age, sex, and weight of the individual, and the ability of the antagonist to elicit a desired response in the individual. A therapeutically effective amount encompasses an amount in which any toxic or detrimental effects of the subject antibodies are outweighed by the therapeutically beneficial effects.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

An "article of manufacture" is any manufacture (e.g., a package or container) or kit comprising at least one reagent, e.g., a medicament for treatment of a disease or disorder, or a probe for specifically detecting a biomarker described herein. In some embodiments, the manufacture or kit is promoted, distributed, or sold as a unit for performing the methods described herein.

3. Methods of Treating Cancer

The invention described herein provides anti-TNFR2 antibodies for use in methods of treating humans and other non-human mammals.

In a pathological situation, Tregs may cause an inappropriate immune suppression, which could, for example, promotes tumor growth. Tregs have been associated with reducing the anti-tumoral immune responses, in particular by inappropriately inhibiting the activity of the effector T lymphocytes, thus promoting the development of numerous cancer types.

In some embodiments, methods for treating or preventing a cancer are provided, comprising administering an effective amount of any of the subject anti-TNFR2 antibodies or antigen-binding fragments thereof to a subject in need of such treatment.

In some embodiments, methods of treating cancer are provided, wherein the methods comprise administering any of the subject anti-TNFR2 antibodies or antigen-binding fragments thereof to a subject with cancer.

The cancers treatable by the method/use of the invention include those in which the regulatory T lymphocytes exert their suppressor activity, such as those cancers in which relatively large amount of the regulatory T lymphocytes are present in the tumoral tissue or in the circulation. Expansion of the regulatory T lymphocytes (which can be measured by frequency of Tregs) is generally correlated with an increase of Tregs activation. The frequency of the regulatory T lymphocytes can be assessed by any method known in the art, for example by a flow cytometry (FACS) analysis of the intra-tumoral lymphocytes or circulating lymphocytes, or by an immuno-histological staining of the tumoral tissue.

Non-limiting exemplary cancers that may be treated with any of the subject anti-TNFR2 antibodies or antigen-binding fragments thereof are provided herein, including carcinoma, lymphoma, blastoma, sarcoma, and leukemia. More particular non-limiting examples of such cancers include melanoma, cervical cancer, squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

In certain embodiment, the cancer is melanoma, breast cancer, colon cancer, cervical cancer, renal cancer, liver cancer (e.g., heptocellular carcinoma), lung cancer (NSCLC), ovarian cancer, skin cancer (e.g., squamous cell carcinoma or basal cell carcinoma), lymphoma, or leukemia.

In certain embodiment, the cancer has a high TNFR2 index, defined as the ratio between (a) the total CD8 T cell number in a tumor sample×TNFR2 expression on CD8 T cells; and (b) the total Treg cell number in a tumor sample× TNFR2 expression on Tregs.

In certain embodiment, the cancer has a TNFR2 index of over 1, such as over 1.5, over 2, over 3, over 4, or over 5. For example, representative TNFR2 indices for certain cancers include: 4.57 for melanima, 1.67 for breast cancer, 1.05 for NSCLC, 1.03 for SCC, 0.78 for BCC, and 0.46 for HCC.

In certain embodiment, the cancer has a TNFR2 index of about 0.5-about 1.

In certain embodiment, the cancer has a high proportion of CD8 TILs (tumor infiltrating lymphocytes), such as more than 20%, 25%, 30%, 35%, 40%, 45%, 50%, 55%, 60% or more of the T cells in a tumor are CD8 T cells.

In certain embodiment, the cancer has a low level of TNFR2 expression on tumor cells.

In certain embodiment, the cancer is known to be susceptible to immune therapy (e.g., inflammed), such as melanoma, NSCLC, renal cell carcinoma, gastric cancer, colorectal cancer, urothelial cancer, HCC, head and neck cancer, and Hodgkin's Lymphoma.

In certain embodiment, the cancer has high level of TNFR2 expression on intra-tumoral exhausted T cells, such as exhausted CD8 T cells. Such cancer may be treated with a combination therapy with, for example, an antagonist of the PD-1/PD-L1 pathway, such as any of the anti-PD-1 or anti-PD-L1 antibodies (e.g., either described herein specifically or known in the art).

In certain embodiment, the method/use of the invention can be used to treat cancers in which there are known high levels of regulatory T lymphocytes, and/or which cancers/tumors are clearly associated with poor prognosis, including: chronic myeloid leukemia (CIVIL), colon cancer, melanoma, cancer of the uterus, breast cancer, pancreatic cancer, gastric cancers, ovarian cancer, primary lymphoma of the central nervous system, multiple myelomas, prostate cancer, Hodgkin's lymphoma, or hepatocellular carcinoma.

In some embodiments, the cancer is a hematological cancer (such as AML and DLBCL), or a solid tumor (such as breast cancer, head and neck cancer, lung cancer, melanoma (including uveal melanoma), colon cancer, renal carcinoma, ovarian cancer, liver cancer, and prostate cancer).

In some embodiments, the cancer is BCC, SCC, melanoma, colorectal cancer, or NSCLC.

In certain embodiment, the method/use of the invention can be used to treat recurrence of fibrosis resulting from hepatitis C, since it has also been demonstrated that increasing the frequency of the regulatory T lymphocytes is a factor predicting recurrence of such fibrosis.

In some embodiments, the anti-TNFR2 antibodies of the invention can be used alone, or alternatively used in combination with any other suitable compound known to be able to treat the disease or indication.

Thus according to a particular embodiment of the invention, an antibody directed against TNFR2 and inhibiting the suppressor activity of regulatory T lymphocytes as previously defined is used in combination with a second therapeutic agent for treating a disease associated with the suppressor activity of regulatory T lymphocytes, for example an anticancer agent.

That is, when the use is the treatment of a cancer, the antibody can be used in combination with known therapies against cancer such as for example surgery, radiotherapy, chemotherapy or combinations thereof. For example, the antibody can be used in combination with an adoptive immunotherapy, consisting one or more injections of effector lymphocytes against tumoral antigens, in particular EBV antigens. According to some aspects, other anticancer agents used in combination with the antibody directed against TNFR2 according to the invention for cancer therapy comprise anti-angiogenics. According to certain aspects, the antibody can be co-administered with a cytokine, for example a cytokine that stimulates an anti-tumoral immune response.

In such combination therapy, the antibody of the invention can be used before, after, or concurrently with the second therapeutic agent. See further section below concerning combination therapy.

4. Routes of Administration and Carriers

In various embodiments, the subject anti-TNFR2 monoclonal antibodies may be administered subcutaneously or intravenously. For simplicity, "the subject anti-TNFR2 monoclonal antibodies" refer to mouse-human chimeric anti-TNFR2 antibody of the invention, as well as the humanized variants thereof.

In some embodiments, the subject anti-TNFR2 monoclonal antibodies may be administered in vivo by various routes, including, but not limited to, oral, intra-arterial, parenteral, intranasal, intramuscular, intracardiac, intraventricular, intratracheal, buccal, rectal, intraperitoneal, by inhalation, intradermal, topical, transdermal, and intrathecal, or otherwise, e.g., by implantation.

In some embodiments, the subject anti-TNFR2 monoclonal antibodies may be administered via i.v. or s.c.

The subject antibody compositions may be formulated into preparations in solid, semi-solid, liquid, or gaseous forms; including, but not limited to, tablets, capsules, powders, granules, ointments, solutions, suppositories, enemas, injections, inhalants, and aerosols.

In various embodiments, compositions comprising the subject anti-TNFR2 monoclonal antibodies are provided in formulations with a wide variety of pharmaceutically acceptable carriers (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Nonlimiting exemplary carriers include saline, buffered saline, dextrose, water, glycerol, ethanol, and combinations thereof.

In various embodiments, compositions comprising the subject anti-TNFR2 monoclonal antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives.

In various embodiments, the compositions may be formulated for inhalation, for example, using pressurized acceptable propellants such as dichlorodifluoromethane, propane, nitrogen, and the like.

The compositions may also be formulated, in various embodiments, into sustained release microcapsules, such as with biodegradable or non-biodegradable polymers. A non-limiting exemplary biodegradable formulation includes poly lactic acid-glycolic acid (PLGA) polymer. A non-limiting exemplary non-biodegradable formulation includes a polyglycerin fatty acid ester. Certain methods of making such formulations are described, for example, in EP 1125584 A1.

Pharmaceutical dosage packs comprising one or more containers, each containing one or more doses of the subject anti-TNFR2 monoclonal antibodies, are also provided. In some embodiments, a unit dosage is provided wherein the unit dosage contains a predetermined amount of a composition comprising the subject anti-TNFR2 monoclonal antibodies, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated.

In some embodiments, the subject anti-TNFR2 monoclonal antibodies may be administered in an amount in the range of about 50 µg/kg body weight to about 50 mg/kg body weight per dose. In some embodiments, the subject anti-TNFR2 monoclonal antibodies may be administered in an amount in the range of about 100 µg/kg body weight to about 50 mg/kg body weight per dose. In some embodiments, the subject anti-TNFR2 monoclonal antibodies may be administered in an amount in the range of about 100 µg/kg body weight to about 20 mg/kg body weight per dose. In some embodiments, the subject anti-TNFR2 monoclonal antibodies may be administered in an amount in the range of about 0.5 mg/kg body weight to about 20 mg/kg body weight per dose.

In some embodiments, the subject anti-TNFR2 monoclonal antibodies may be administered in an amount in the range of about 10 mg to about 1,000 mg per dose. In some embodiments, the subject anti-TNFR2 monoclonal antibodies may be administered in an amount in the range of about 20 mg to about 500 mg per dose. In some embodiments, the subject anti-TNFR2 monoclonal antibodies may be administered in an amount in the range of about 20 mg to about 300 mg per dose. In some embodiments, the subject anti-TNFR2 monoclonal antibodies may be administered in an amount in the range of about 20 mg to about 200 mg per dose.

The subject anti-TNFR2 monoclonal antibody compositions may be administered as needed to subjects. In some embodiments, an effective dose of the subject anti-TNFR2 monoclonal antibodies is administered to a subject one or more times. In various embodiments, an effective dose of the subject anti-TNFR2 monoclonal antibodies is administered to the subject once a month, less than once a month, such as, for example, every two months, every three months, or every six months. In other embodiments, an effective dose of the subject anti-TNFR2 monoclonal antibodies is administered more than once a month, such as, for example, every two weeks, every week, twice per week, three times per week, daily, or multiple times per day. An effective dose of the subject anti-TNFR2 monoclonal antibodies is administered to the subject at least once. In some embodiments, the effective dose of the subject anti-TNFR2 monoclonal antibodies may be administered multiple times, including for periods of at least a month, at least six months, or at least a year. In some embodiments, the subject anti-TNFR2 monoclonal antibodies is administered to a subject as-needed to alleviate one or more symptoms of a condition.

5. Combination Therapy

The subject anti-TNFR2 monoclonal antibodies of the invention, including functional fragments thereof, may be administered to a subject in need thereof in combination with other biologically active substances or other treatment procedures for the treatment of diseases. For example, the subject anti-TNFR2 monoclonal antibodies may be administered alone or with other modes of treatment. They may be provided before, substantially contemporaneous with, or after other modes of treatment, such as radiation therapy.

For treatment of cancer, the subject anti-TNFR2 monoclonal antibodies may be administered in conjunction with one or more of anti-cancer agents, such as the immune checkpoint inhibitor, chemotherapeutic agent, growth inhibitory agent, anti-angiogenesis agent or anti-neoplastic composition.

In certain embodiments, the subject anti-TNFR2 monoclonal antibodies specifically binds to TNFR2 (a "TNFR2-binding antagonist"), e.g., TNFR2 antagonist antibody or antigen-binding fragment thereof, is administered with a second antagonist such as an immune checkpoint inhibitor (e.g., an inhibitor of the PD-1 or PD-L1 pathway), to a subject having a disease in which the stimulation of the immune system would be beneficial, e.g., cancer or infectious diseases. The two antagonists may be administered simultaneously or consecutively, e.g., as described below for the combination of the subject anti-TNFR2 monoclonal antibodies with an immuno-oncology agent. One or more additional therapeutics, e.g., checkpoint modulators may be added to a treatment with the subject anti-TNFR2 monoclonal antibodies for treating cancer or autoimmune diseases.

In certain embodiments, the subject anti-TNFR2 monoclonal antibodies is administered with another treatment, either simultaneously, or consecutively, to a subject, e.g., a subject having cancer. For example, the subject anti-TNFR2 monoclonal antibodies may be administered with one of more of: radiotherapy, surgery, or chemotherapy, e.g., targeted chemotherapy or immunotherapy.

In certain embodiments, a method of treatment of a subject having cancer comprises administering to the subject an anti-TNFR2 monoclonal antibody of the invention, and one or more immuno-oncology agents, such as immune checkpoint inhibitor.

Immunotherapy, e.g., therapy with an immuno-oncology agent, is effective to enhance, stimulate, and/or upregulate immune responses in a subject. In one aspect, the administration of the subject anti-TNFR2 monoclonal antibodies with an immuno-oncology agent (such as a PD-1 inhibitor) has a synergic effect in the treatment of cancer, e.g., in inhibiting tumor growth.

In one aspect, a subject anti-TNFR2 monoclonal antibody is sequentially administered prior to administration of the immuno-oncology agent. In one aspect, a subject anti-TNFR2 monoclonal antibody is administered concurrently with the immunology-oncology agent (such as PD-1 inhibitor). In yet one aspect, a subject anti-TNFR2 monoclonal antibody is sequentially administered after administration of the immuno-oncology agent (such as PD-1 inhibitor). The administration of the two agents may start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent may start, e.g., 30 \ minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In certain aspects, the subject anti-TNFR2 monoclonal antibodies and an immuno-oncology agent (e.g., PD-1 inhibitor) are administered simultaneously, e.g., are infused simultaneously, e.g., over a period of 30 or 60 minutes, to a patient. The subject anti-TNFR2 monoclonal antibodies may be co-formulated with an immuno-oncology agent (such as PD-1 inhibitor).

Immuno-oncology agents include, for example, a small molecule drug, antibody or fragment thereof, or other biologic or small molecule. Examples of biologic immuno-oncology agents include, but are not limited to, antibodies, antibody fragments, vaccines and cytokines. In one aspect, the antibody is a monoclonal antibody. In certain aspects, the monoclonal antibody is humanized or human antibody.

In one aspect, the immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on immune cells, e.g., T cells, both of which result in amplifying antigen-specific T cell responses. In certain aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells involved in innate immunity, e.g., NK cells, and wherein the immuno-oncology agent enhances innate immunity. Such immuno-oncology agents are often referred to as immune checkpoint regulators, e.g., immune checkpoint inhibitor or immune checkpoint stimulator.

In certain embodiments, the immuno-oncology agent may be an agent that targets (or binds specifically to) a member of the B7 family of membrane-bound ligands, which includes B7-1, B7-2, B7-H1 (PD-L1), B7-DC (PD-L2), B7-H2 (ICOS-L), B7-H3, B7-H4, B7-H5, and B7-H6, or a co-stimulatory or co-inhibitory receptor binding specifically to a B7 family member. An immuno-oncology agent may be an agent that targets a member of the TNF family of membrane bound ligands or a co-stimulatory or co-inhibitory receptor binding specifically thereto, e.g., a TNF receptor family member. Exemplary TNF and TNFR family members that may be targeted by immuno-oncology agents include CD40 and CD40L, OX-40, OX-40L, GITR, GITRL, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTßR, LIGHT, DcR3, HVEM, VEGI/TL1A, TRAMP/DR3, EDAR, EDA1, XEDAR, EDA2, TNFR1, Lymphotoxin α/TNPβ, TNFR2, TNFα, LTßR, Lymphotoxin a 1β2, FAS, FASL, RELT, DR6, TROY and NGFR. An immuno-oncology agent that may be used in combination with the subject anti-TNFR2 monoclonal antibodies for treating cancer may be an agent, e.g., an antibody, targeting a B7 family member, a B7 receptor family member, a TNF family member or a TNFR family member, such as those described above.

In one aspect, a subject anti-TNFR2 monoclonal antibody is administered with one or more of (i) an antagonist of a protein that inhibits T cell activation (e.g., immune checkpoint inhibitor) such as CTLA-4, PD-1, PD-L1, PD-L2, LAG-3, TIM3, CEACAM-1, BTLA, CD69, Galectin-1, TIGIT, CD113, GPR56, VISTA, B7-H3, B7-H4, 2B4, CD48, GARP, PDIH, LAIR1, TIM-1, TIM-4, and PSGL-1 and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, CD40L, DR3 and CD28H.

In one aspect, an immuno-oncology agent is an agent that inhibits (i.e., an antagonist of) a cytokine that inhibits T cell activation (e.g., IL-6, IL-10, TGF-β, VEGF, and other immunosuppressive cytokines) or is an agonist of a cytokine, such as IL-2, IL-7, IL-12, IL-15, IL-21 and IFNα (e.g., the cytokine itself) that stimulates T cell activation, and stimulates an immune response.

Other agents that can be combined with the subject anti-TNFR2 monoclonal antibodies for stimulating the immune system, e.g., for the treatment of cancer and infectious diseases, include antagonists of inhibitory receptors on NK cells or agonists of activating receptors on NK cells. For example, the subject anti-TNFR2 monoclonal antibodies can be combined with an antagonist of MR.

Yet other agents for combination therapies include agents that inhibit or deplete macrophages or monocytes, including but not limited to CSF-IR antagonists such as CSF-IR antagonist antibodies including RG7155 (WO1 1/70024, WO1 1/107553, WO11/131407, WO13/87699, WO13/119716, WO13/132044) or FPA008 (WO1 1/140249; WO13169264; WO14/036357).

Immuno-oncology agents also include agents that inhibit TGF-β signaling.

Additional agents that may be combined with the subject anti-TNFR2 monoclonal antibodies include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies that may be combined with the subject anti-TNFR2 monoclonal antibodies include therapies that deplete or block Treg cells, e.g., an agent that specifically binds to CD25.

Another therapy that may be combined with the subject anti-TNFR2 monoclonal antibodies is a therapy that inhibits a metabolic enzyme such as indoleamine dioxigenase (IDO), dioxigenase, arginase, or nitric oxide synthetase.

Another class of agents that may be used includes agents that inhibit the formation of adenosine or inhibit the adenosine A2A receptor.

Other therapies that may be combined with the subject anti-TNFR2 monoclonal antibodies for treating cancer include therapies that reverse/prevent T cell anergy or exhaustion and therapies that trigger an innate immune activation and/or inflammation at a tumor site.

The subject anti-TNFR2 monoclonal antibodies may be combined with more than one immuno-oncology agent (such as immune checkpoint inhibitor), and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Treg or other immune suppressing cells; a therapy that stimulates positive immune regulation, e.g., with agonists that stimulate the CD-137, OX-40 and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase or nitric oxide synthetase; a therapy that reverses/prevents T cell anergy or exhaustion; a therapy that triggers an innate immune activation and/or inflammation at a tumor site; administration of immune stimulatory cytokines or blocking of immuno repressive cytokines.

For example, the subject anti-TNFR2 monoclonal antibodies can be used with one or more agonistic agents that ligate positive costimulatory receptors; one or more antagonists (blocking agents) that attenuate signaling through inhibitory receptors, such as antagonists that overcome distinct immune suppressive pathways within the tumor microenvironment (e.g., block PD-L1/PD-1/PD-L2 interactions); one or more agents that increase systemically the frequency of anti-tumor immune cells, such as T cells, deplete or inhibit Tregs (e.g., by inhibiting CD25); one or more agents that inhibit metabolic enzymes such as IDO; one or more agents that reverse/prevent T cell anergy or exhaustion; and one or more agents that trigger innate immune activation and/or inflammation at tumor sites.

In one embodiment, a subject having a disease that may benefit from stimulation of the immune system, e.g., cancer or an infectious disease, is treated by administration to the subject of the subject anti-TNFR2 monoclonal antibodies and an immuno-oncology agent, wherein the immuno-oncology agent is a CTLA-4 antagonist, such as an antagonistic CTLA-4 antibody. Suitable CTLA-4 antibodies include, for example, YERVOY (ipilimumab) or tremelimumab.

In one embodiment, a subject having a disease that may benefit from stimulation of the immune system, e.g., cancer or an infectious disease, is treated by administration to the subject of the subject anti-TNFR2 monoclonal antibodies and an immuno-oncology agent, wherein the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011). Another approach to target the PD-1 receptor is the recombinant protein composed of the extracellular domain of PD-L2 (B7-DC) fused to the Fc portion of IgG1, called AMP-224.

In one embodiment, a subject having a disease that may benefit from stimulation of the immune system, e.g., cancer or an infectious disease, is treated by administration to the subject of an anti-TNFR2 monoclonal antibody of the invention and an immuno-oncology agent, wherein the immuno-oncology agent is a PD-L1 antagonist, such as an antagonistic PD-L1 antibody. Suitable PD-L1 antibodies include, for example, MEDL3280A (RG7446; WO2010/077634), durvalumab (MEDI4736), BMS-936559 (WO2007/005874), MSB0010718C (WO2013/79174) or rHigM12B7.

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is a CD137 (4-1BB) agonist, such as an agonistic CD137 antibody. Suitable CD137 antibodies include, for example, urelumab or PF-05082566 (WO12/32433).

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is a GITR agonist, such as an agonistic GITR antibody. Suitable GITR antibodies include, for example, TRX-518 (WO06/105021, WO09/009116), MK-4166 (WO 11/028683) or a GITR antibody disclosed in WO2015/031667.

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is an OX40 agonist, such as an agonistic OX40 antibody. Suitable OX40 antibodies include, for example, MEDI-6383, MEDI-6469 or MOXR0916 (RG7888; WO06/029879).

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is a CD40 agonist, such as an agonistic CD40 antibody. In certain embodiments, the immuno-oncology agent is a CD40 antagonist, such as an antagonistic CD40 antibody. Suitable CD40 antibodies include, for example, lucatumumab (HCD122), dacetuzumab (SGN-40), CP-870,893 or Chi Lob 7/4.

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is a CD27 agonist, such as an agonistic CD27 antibody. Suitable CD27 antibodies include, for example, varlilumab (CDX-1127).

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is MGA271 (to B7H3) (WO11/109400).

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is a KIR antagonist, such as lirilumab.

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is an IDO antagonist. Suitable IDO antagonists include, for example, INCB-024360 (WO2006/122150, WO07/75598, WO08/36653, WO08/36642), indoximod, NLG-919 (WO09/73620, WO09/1156652, WO1 1/56652, WO 12/142237) or F001287.

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein the immuno-oncology agent is a Toll-like receptor agonist, e.g., a TLR2/4 agonist (e.g., Bacillus Calmette-Guerin); a TLR7 agonist (e.g., Hiltonol or Imiquimod); a TLR7/8 agonist (e.g., Resiquimod); or a TLR9 agonist (e.g., CpG7909).

In one embodiment, a subject having a disease that may benefit from stimulation of the immune system, e.g., cancer or an infectious disease, is treated by administration to the subject an anti-TNFR2 monoclonal antibody of the invention and an immuno-oncology agent, wherein, the immuno-oncology agent is a TGF-β inhibitor, e.g., GC1008, LY2157299, TEW7197 or IMC-TR1.

6. Exemplary Anti-TNFR2 Monoclonal Antibody

The invention described herein provides monoclonal antibodies specific for TNFR2, or antigen-binding fragments thereof.

Thus one aspect of the invention provides an isolated monoclonal antibody, or an antigen-binding fragment thereof, which competes with any of the isolated monoclonal antibody or antigen-binding fragment thereof described herein for binding to the epitope of SEQ ID NO: 13 or 38, or for binding to the epitope bound by HFB3-18.

A related aspect of the invention provides an isolated monoclonal antibody, or an antigen-binding fragment thereof, which specifically binds to the epitope of SEQ ID NO: 13 or 38, or the epitope bound by HFB3-18.

Another related aspect of the invention provides an isolated monoclonal antibody, or an antigen-binding fragment thereof, wherein said monoclonal antibody or antigen-binding fragment thereof is specific for human TNFR2, and wherein said monoclonal antibody comprises: (1a) a heavy chain variable region (HCVR), comprising a HCVR CDR1 sequence of SEQ ID NO: 1, a HCVR CDR2 sequence of SEQ ID NO: 2, and a HCVR CDR3 sequence of SEQ ID NO: 3; and, (1b) a light chain variable region (LCVR), comprising a LCVR CDR1 sequence of SEQ ID NO: 4, a LCVR CDR2 sequence of SEQ ID NO: 5, and a LCVR CDR3 sequence of SEQ ID NO: 6; or (2a) a heavy chain variable region (HCVR), comprising a HCVR CDR1 sequence of SEQ ID NO: 14, a HCVR CDR2 sequence of SEQ ID NO: 15, and a HCVR CDR3 sequence of SEQ ID NO: 16; and, (2b) a light chain variable region (LCVR), comprising a LCVR CDR1 sequence of SEQ ID NO: 17, a LCVR CDR2 sequence of SEQ ID NO: 18, and a LCVR CDR3 sequence of SEQ ID NO: 19; or (3a) a heavy chain variable region (HCVR), comprising a HCVR CDR1 sequence of SEQ ID NO: 26, a HCVR CDR2 sequence of SEQ ID NO: 27, and a HCVR CDR3 sequence of SEQ ID NO: 28; and, (3b) a light chain variable region (LCVR), comprising a LCVR CDR1 sequence of SEQ ID NO: 29, a LCVR CDR2 sequence of SEQ ID NO: 30, and a LCVR CDR3 sequence of SEQ ID NO: 31; or (4a) a heavy chain variable region (HCVR), comprising a HCVR CDR1 sequence of SEQ ID NO: 39, a HCVR CDR2 sequence of SEQ ID NO: 40, and a HCVR CDR3 sequence of SEQ ID NO: 41; and, (4b) a light chain variable region (LCVR), comprising a LCVR CDR1 sequence of SEQ ID NO: 42, a LCVR CDR2 sequence of SEQ ID NO: 43, and a LCVR CDR3 sequence of SEQ ID NO: 44; or (5a) a heavy chain variable region (HCVR), comprising a HCVR CDR1 sequence of SEQ ID NO: 51, a HCVR CDR2 sequence of SEQ ID NO: 52, and a HCVR CDR3 sequence of SEQ ID NO: 53; and, (5b) a light chain variable region (LCVR), comprising a LCVR CDR1 sequence of SEQ ID NO: 54, a LCVR CDR2 sequence of SEQ ID NO: 55, and a LCVR CDR3 sequence of SEQ ID NO: 56; or (6a) a heavy chain variable region (HCVR), comprising a HCVR CDR1 sequence of SEQ ID NO: 63, a HCVR CDR2 sequence of SEQ ID NO: 64, and a HCVR CDR3 sequence of SEQ ID NO: 65; and, (6b) a light chain variable region (LCVR), comprising a LCVR CDR1 sequence of SEQ ID NO: 66, a LCVR CDR2 sequence of SEQ ID NO: 67, and a LCVR CDR3 sequence of SEQ ID NO: 68.

For any of the aspects of the invention described above, in some embodiments, in the isolated monoclonal antibody or antigen-binding fragment thereof: (1A) the HCVR sequence is SEQ ID NO: 7; and/or, (1B) the LCVR sequence is SEQ ID NO: 8, or, (2A) the HCVR sequence is SEQ ID NO: 20; and/or, (2B) the LCVR sequence is SEQ ID NO: 21, or, (3A) the HCVR sequence is SEQ ID NO: 32; and/or, (3B) the LCVR sequence is SEQ ID NO: 33, or, (4A) the HCVR sequence is SEQ ID NO: 45; and/or, (4B) the LCVR sequence is SEQ ID NO: 46, or, (5A) the HCVR sequence is SEQ ID NO: 57; and/or, (5B) the LCVR sequence is SEQ ID NO: 58, or, (6A) the HCVR sequence is SEQ ID NO: 69; and/or, (6B) the LCVR sequence is SEQ ID NO: 70.

In some embodiments, the isolated monoclonal antibody or antigen-binding fragment thereof has: (1a) a heavy chain sequence of SEQ ID NO: 9; and/or, (1b) a light chain sequence of SEQ ID NO: 10, or, (2a) a heavy chain sequence of SEQ ID NO: 22; and/or, (2b) a light chain sequence of SEQ ID NO: 23, or, (3a) a heavy chain sequence of SEQ ID NO: 34; and/or, (3b) a light chain sequence of SEQ ID NO: 35, or, (4a) a heavy chain sequence of SEQ ID NO: 47; and/or, (4b) a light chain sequence of SEQ ID NO: 48, or, (5a) a heavy chain sequence of SEQ ID NO: 59; and/or, (5b) a light chain sequence of SEQ ID NO: 60, or, (6a) a heavy chain sequence of SEQ ID NO: 71; and/or, (6b) a light chain sequence of SEQ ID NO: 72.

Some of the sequences of the antibodies of the invention are provided below.

```
HFB3-1-hG1 (mouse monoclonal antibody)
CDR-H1:
                                            (SEQ ID NO: 1)
SYSFTDYN CDR-H2:
                                            (SEQ ID NO: 2)
IFPKYGTTSYNQKFKG

CDR-H3:
                                            (SEQ ID NO: 3)
ATDGGTWYFDV

CDR-L1:
                                            (SEQ ID NO: 4)
SSVTY
```

-continued

CDR-L2:

(SEQ ID NO: 5)

LTSNLASGVPA

CDR-L3:

(SEQ ID NO: 6)

QQWSSNPPT

HCVR IS SEQ ID NO: 7, AND LCVR IS SEQ ID NO: 8.

HC:

(SEQ ID NO: 9)

EFQLQQSGPELVKPGASVKISCKASSYSFTDYNMNWVKQSNGKSLEWIGIIFPKYGTTSYNQKF

KGKATLTVDQSSSTAYMQLNSLTSEDSAVYYCATDGGTWYFDVWGTGTTVTVSSASTKGPSVFP

LAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKSLSLSPGK

LC:

(SEQ ID NO: 10)

QIVLTQSPALMSASPGEKVTMTCSASSSVTYMYWYQQKPRSSPKPWIYLTSNLASGVPARFSGS

GSGTSYSLTISSMEAEDAATYYCQQWSSNPPTFGSGTKLEIKRTVAAPSVFIFPPSDEQLKSGT

ASVVCLLNNFYPREAKVQWKVDNALQSGNSQESVTEQDSKDSTYSLSSTLTLSKADYEKHKVYA

CEVTHQGLSSPVTKSFNRGEC (SEQ ID NO: 11)

GAATTTCAGCTGCAGCAGTCTGGCCCCGAGCTGGTTAAGCCTGGCGCCTCTGTGAAGATCAGCT

GCAAGGCCAGCAGCTACAGCTTCACCGACTACAACATGAACTGGGTCAAGCAGAGCAACGGCAA

GAGCCTGGAATGGATCGGCATCATCTTCCCTAAGTACGGCACCACCAGCTACAACCAGAAGTTC

AAGGGCAAAGCCACACTGACCGTGGACCAGAGCAGCAGCACAGCCTACATGCAGCTCAACAGCC

TGACCAGCGAGGACAGCGCCGTGTACTACTGTGCTACAGATGGCGGCACCTGGTACTTCGATGT

GTGGGGCACTGGCACCACCGTGACAGTTAGTTCTGCGTCGACCAAGGGCCCATCGGTCTTCCCC

CTGGCACCCTCCTCCAAGAGCACCTCTGGGGGCACAGCGGCCCTGGGCTGCCTGGTCAAGGACT

ACTTCCCCGAACCGGTGACGGTGTCGTGGAACTCAGGCGCCCTGACCAGCGGCGTGCACACCTT

CCCGGCTGTCCTACAGTCCTCAGGACTCTACTCCCTCAGCAGCGTGGTGACCGTGCCCTCCAGC

AGCTTGGGCACCCAGACCTACATCTGCAACGTGAATCACAAGCCCAGCAACACCAAGGTGGACA

AGAAAGTTGAGCCCAAATCTTGTGACAAAACTCACACATGCCCACCGTGCCCAGCACCTGAACT

CCTGGGGGGACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACT

GGTACGTGGACGGCGTGGAGGTGCATAATGCCAAGACAAAGCCGCGGGAGGAGCAGTACAACAG

CACGTACCGTGTGGTCAGCGTCCTCACCGTCCTGCACCAGGACTGGCTGAATGGCAAGGAGTAC

AAGTGCAAGGTCTCCAACAAAGCCCTCCCAGCCCCCATCGAGAAAACCATCTCCAAAGCCAAAG

GGCAGCCCCGAGAACCACAGGTGTACACCCTGCCCCCATCCCGGGAGGAGATGACCAAGAACCA

GGTCAGCCTGACCTGCCTGGTCAAAGGCTTCTATCCCAGCGACATCGCCGTGGAGTGGGAGAGC

AATGGGCAGCCGGAGAACAACTACAAGACCACGCCTCCCGTGCTGGACTCCGACGGCTCCTTCT

TCCTCTATAGCAAGCTCACCGTGGACAAGAGCAGGTGGCAGCAGGGGAACGTCTTCTCATGCTC

CGTGATGCATGAGGCTCTGCACAACCACTACACGCAGAAGAGCCTCTCCCTGTCCCCGGGTAAA

TGA

-continued (SEQ ID NO: 12)
CAGATTGTGCTGACACAGTCTCCCGCTCTGATGAGCGCTAGCCCTGGCGAGAAAGTGACCATGA

CATGTAGCGCCAGCAGCAGCGTGACCTACATGTACTGGTATCAGCAGAAGCCCAGAAGCAGCCC

CAAGCCTTGGATCTACCTGACCAGCAATCTGGCCAGCGGAGTGCCTGCCAGATTTTCTGGCTCT

GGCAGCGGCACAAGCTACAGCCTGACAATCAGCAGCATGGAAGCCGAGGATGCCGCCACCTACT

ACTGCCAGCAGTGGTCCAGCAATCCTCCTACATTTGGCTCCGGCACCAAGCTGGAAATCAAGCG

TACGGTGGCTGCACCATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCC

TGCGAAGTCACCCATCAGGGCCTGAGCTCGCCCGTCACAAAGAGCTTCAACAGGGGAGAGTGTT

AG (SEQ ID NO: 13)
SCEDSTYTQLWNWVPECLS

HFB3-1hz6-hG1 (humanized monoclonal antibody)
CDR-H1:
(SEQ ID NO: 14)
SYSFTDYN

CDR-H2:
(SEQ ID NO: 15)
IFPKYGTTSYAQKLQG

CDR-H3:
(SEQ ID NO: 16)
ATDGGTWYEDV

CDR-L1:
(SEQ ID NO: 17)
SSVTY

CDR-L2:
(SEQ ID NO: 18)
LTSNLASGVPS

CDR-L3:
(SEQ ID NO: 19)
QQWSSNPPT

HCVR IS SEQ ID NO: 20, AND LCVR IS SEQ ID NO: 21.

HC:
(SEQ ID NO: 22)
QVQLVQSGAELKKPGASVKVSCKASSYSFTDYNMNWVRQAPGQSLEWMGIIFPKYGTTSYAQKL

QGRVTLTTDTSTSTAYMELRSLRSDDTAVYYCATDGGTWYFDVWGTGTTVTVSSASTKGPSVFP

LAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKSLSLSPGK

LC:
(SEQ ID NO: 23)
DIQLTQSPSFLSASVGDRVTITCRASSSVTYMYWYQQKPGKAPKPWIYLTSNLASGVPSRFSGS

GSGTEYTLTISSLQPEDAATYYCQQWSSNPPTFGSGTKLEIKRTVAAPSVFIFPPSDEQLKSGT

ASVVCLLNNFYPREAKVQWKVDNALQSGNSQESVTEQDSKDSTYSLSSTLTLSKADYEKHKVYA

CEVTHQGLSSPVTKSFNRGEC

-continued (SEQ ID NO: 24)

CAGGTTCAGCTGGTTCAGTCTGGCGCCGAGCTGAAAAAACCTGGCGCCTCTGTGAAGGTGTCCT

GCAAGGCCAGCAGCTACAGCTTCACCGACTACAACATGAACTGGGTCCGACAGGCCCCTGGCCA

GTCTCTTGAGTGGATGGGCATCATCTTCCCTAAGTACGGCACCACCAGCTACGCCCAGAAACTG

CAGGGAAGAGTGACCCTGACCACCGACACCAGCACAAGCACCGCCTACATGGAACTGCGGAGCC

TGAGATCCGATGACACCGCCGTGTACTACTGTGCCACAGATGGCGGCACCTGGTACTTCGATGT

GTGGGGCACTGGCACCACCGTGACAGTCTCTTCTGCGTCGACCAAGGGCCCATCGGTCTTCCCC

CTGGCACCCTCCTCCAAGAGCACCTCTGGGGGCACAGCGGCCCTGGGCTGCCTGGTCAAGGACT

ACTTCCCCGAACCGGTGACGGTGTCGTGGAACTCAGGCGCCCTGACCAGCGGCGTGCACACCTT

CCCGGCTGTCCTACAGTCCTCAGGACTCTACTCCCTCAGCAGCGTGGTGACCGTGCCCTCCAGC

AGCTTGGGCACCCAGACCTACATCTGCAACGTGAATCACAAGCCCAGCAACACCAAGGTGGACA

AGAAAGTTGAGCCCAAATCTTGTGACAAAACTCACACATGCCCACCGTGCCCAGCACCTGAACT

CCTGGGGGGACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACT

GGTACGTGGACGGCGTGGAGGTGCATAATGCCAAGACAAAGCCGCGGGAGGAGCAGTACAACAG

CACGTACCGTGTGGTCAGCGTCCTCACCGTCCTGCACCAGGACTGGCTGAATGGCAAGGAGTAC

AAGTGCAAGGTCTCCAACAAAGCCCTCCCAGCCCCCATCGAGAAAACCATCTCCAAAGCCAAAG

GGCAGCCCCGAGAACCACAGGTGTACACCCTGCCCCCATCCCGGGAGGAGATGACCAAGAACCA

GGTCAGCCTGACCTGCCTGGTCAAAGGCTTCTATCCCAGCGACATCGCCGTGGAGTGGGAGAGC

AATGGGCAGCCGGAGAACAACTACAAGACCACGCCTCCCGTGCTGGACTCCGACGGCTCCTTCT

TCCTCTATAGCAAGCTCACCGTGGACAAGAGCAGGTGGCAGCAGGGGAACGTCTTCTCATGCTC

CGTGATGCATGAGGCTCTGCACAACCACTACACGCAGAAGAGCCTCTCCCTGTCCCCGGGTAAA

TGA (SEQ ID NO: 25)

GACATCCAGCTGACCCAGTCTCCAAGCTTTCTGAGCGCCAGCGTGGGCGACAGAGTGACCATTA

CATGTAGAGCCAGCAGCAGCGTGACCTATATGTACTGGTATCAGCAGAAGCCCGGCAAGGCCCC

TAAGCCTTGGATCTACCTGACCAGCAATCTGGCCAGCGGCGTGCCAAGCAGATTTTCTGGCTCT

GGCAGCGGCACCGAGTACACCCTGACCATATCTAGCCTGCAGCCTGAGGATGCCGCCACCTACT

ATTGCCAGCAGTGGTCCAGCAATCCTCCTACCTTTGGCTCCGGCACCAAGCTGGAAATCAAGCG

TACGGTGGCTGCACCATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGTACAGTGGAAGGTGG

ATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCC

TGCGAAGTCACCCATCAGGGCCTGAGCTCGCCCGTCACAAAGAGCTTCAACAGGGGAGAGTGTT

AG

HFB3-14-hG1 (mouse monoclonal antibody)
CDR-H1:

(SEQ ID NO: 26)

GYTFTDYY

CDR-H2:

(SEQ ID NO: 27)

INPNDGGTTYSQKFKG

CDR-H3:

(SEQ ID NO: 28)

AREGNYYAYDVRVWYFDV

-continued

CDR-L1:
(SEQ ID NO: 29)
QDIITY

CDR-L2:
(SEQ ID NO: 30)
STSSLNSGVPS

CDR-L3:
(SEQ ID NO: 31)
QQYSELPYT

HCVR IS SEQ ID NO: 32, AND LCVR IS SEQ ID NO: 33.

HC:
(SEQ ID NO: 34)
EVQLQQSGPELVKPGASVRISCKASGYTFTDYYMNWVKQSHGKSLEWIGDINPNDGGTTYSQKF

KGKATLTVDKSSSTAYMELRSLTSEDSAVYFCAREGNYYAYDVRVWYFDVWGTGTTVTVSSAST

KGPSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCSVMHEALHNHYTQKS

LSLSPGK

LC:
(SEQ ID NO: 35)
DIQMTQSPASLSVSVGETVTITCRSSENIYSNLAWYQQKQGKSPQLLVYAATNLADGVPSRFSG

SGSGTQYSLKINSLQSEDFGSYYCQHFWGTPWTFGGGTKLEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC (SEQ ID NO: 36)
GAAGTTCAGCTGCAGCAGTCTGGACCCGAGCTGGTTAAGCCTGGCGCCTCTGTCAGAATCAGCT

GCAAGGCCAGCGGCTACACCTTCACCGACTACTACATGAACTGGGTCAAGCAGAGCCACGGCAA

GAGCCTGGAATGGATCGGCGACATCAACCCCAATGATGGCGGCACCACCTACAGCCAGAAGTTC

AAGGGCAAAGCCACACTGACCGTGGACAAGAGCAGCAGCACCGCCTACATGGAACTGAGAAGCC

TGACCAGCGAGGACAGCGCCGTGTACTTTTGTGCCAGAGAGGGCAACTACTACGCCTACGACGT

CCGCGTGTGGTACTTCGATGTGTGGGGCACAGGCACCACCGTGACAGTTAGTTCTGCGTCGACC

AAGGGCCCATCGGTCTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGGAACTCAGGCGCCCT

GACCAGCGGCGTGCACACCTTCCCGGCTGTCCTACAGTCCTCAGGACTCTACTCCCTCAGCAGC

GTGGTGACCGTGCCCTCCAGCAGCTTGGGCACCCAGACCTACATCTGCAACGTGAATCACAAGC

CCAGCAACACCAAGGTGGACAAGAAAGTTGAGCCCAAATCTTGTGACAAAACTCACACATGCCC

ACCGTGCCCAGCACCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGACGTGAGCCACGAAG

ACCCTGAGGTCAAGTTCAACTGGTACGTGGACGGCGTGGAGGTGCATAATGCCAAGACAAAGCC

GCGGGAGGAGCAGTACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCTGCCCCCATCCCG

GGAGGAGATGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGC

-continued

TGGACTCCGACGGCTCCTTCTTCCTCTATAGCAAGCTCACCGTGGACAAGAGCAGGTGGCAGCA

GGGGAACGTCTTCTCATGCTCCGTGATGCATGAGGCTCTGCACAACCACTACACGCAGAAGAGC

CTCTCCCTGTCCCCGGGTAAATGA (SEQ ID NO: 37)
GACATCCAGATGACACAGTCTCCAGCCAGCCTGTCCGTGTCTGTGGGAGAGACAGTGACCATCA

CCTGTCGGAGCAGCGAGAACATCTACAGCAACCTGGCCTGGTATCAGCAGAAGCAGGGCAAGTC

TCCTCAGCTGCTGGTGTACGCCGCCACCAATCTTGCTGATGGCGTGCCCAGCAGATTTTCCGGC

TCTGGCTCTGGCACACAGTACAGCCTGAAGATCAACAGCCTGCAGAGCGAGGACTTCGGCAGCT

ACTACTGCCAGCACTTTTGGGGCACCCCTTGGACATTTGGCGGAGGCACCAAGCTGGAAATCAA

GCGTACGGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGT

GTTAG (SEQ ID NO: 38)
CAPLRKCRPGFGVARPGTETSD

HFB3-14hz1c-hG1 (humanized monoclonal antibody)
CDR-H1:
                                                                (SEQ ID NO: 39)
GYTFTDYY CDR-H2:
                                                                (SEQ ID NO: 40)
INPNDGGTTYAQKFQG CDR-H3:
                                                                (SEQ ID NO: 41)
AREGNYYAYDVRVWYFDV CDR-L1:
                                                                (SEQ ID NO: 42)
QDIITY CDR-L2:
                                                                (SEQ ID NO: 43)
STSSLNSGVPS CDR-L3:
                                                                (SEQ ID NO: 44)
QQYSELPYT

HCVR IS SEQ ID NO: 45, AND LCVR IS SEQ ID NO: 46.

HC:
                                                                (SEQ ID NO: 47)
QVQLVQSGAEVKKPGSSVKVSCKASGYTFTDYYMNWVRQAPGQGLEWMGDINPNDGGTTYAQKF

QGRVTITADESTSTAYMELSSLRSEDTAVYFCAREGNYYAYDVRVWYFDVWGQGTTVTVSSAST

KGPSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCSVMHEALHNHYTQKS

LSLSPGK

-continued

LC:

(SEQ ID NO: 48)
DIQMTQSPSSLSASVGDRVTITCGASQDIITYLNWYQQKPGKAVKLLIYSTSSLNSGVPSRFSG

SGSGTDFTLTISSLQPEDFATYYCQQYSELPYTFGGGTKVELKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC (SEQ ID NO: 49)
CAGGTTCAGCTGGTTCAGTCTGGCGCCGAAGTGAAGAAACCTGGCAGCAGCGTGAAGGTGTCCT

GCAAGGCCAGCGGCTACACCTTTACCGACTACTACATGAACTGGGTCCGACAGGCCCCTGGACA

GGGACTTGAATGGATGGGCGACATCAACCCCAACGACGGCGGCACAACATACGCCCAGAAATTC

CAGGGCAGAGTGACCATCACCGCCGACGAGTCTACAAGCACCGCCTACATGGAACTGAGCAGCC

TGAGAAGCGAGGATACCGCCGTGTACTTCTGTGCCAGAGAGGGCAACTACTACGCCTACGACGT

CCGCGTGTGGTACTTCGATGTTTGGGGCCAGGGCACCACCGTGACAGTCTCTTCTGCGTCGACC

AAGGGCCCATCGGTCTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGGAACTCAGGCGCCCT

GACCAGCGGCGTGCACACCTTCCCGGCTGTCCTACAGTCCTCAGGACTCTACTCCCTCAGCAGC

GTGGTGACCGTGCCCTCCAGCAGCTTGGGCACCCAGACCTACATCTGCAACGTGAATCACAAGC

CCAGCAACACCAAGGTGGACAAGAAAGTTGAGCCCAAATCTTGTGACAAAACTCACACATGCCC

ACCGTGCCCAGCACCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGACGTGAGCCACGAAG

ACCCTGAGGTCAAGTTCAACTGGTACGTGGACGGCGTGGAGGTGCATAATGCCAAGACAAAGCC

GCGGGAGGAGCAGTACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCTGCCCCCATCCCG

GGAGGAGATGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAGGTGGCAGCA

GGGGAACGTCTTCTCATGCTCCGTGATGCATGAGGCTCTGCACAACCACTACACGCAGAAGAGC

CTCTCCCTGTCCCCGGGTAAATGA (SEQ ID NO: 50)
GACATCCAGATGACACAGAGCCCTAGCAGCCTGTCTGCCAGCGTGGGAGACAGAGTGACCATTA

CATGTGGCGCCAGCCAGGACATCATCACCTACCTGAACTGGTATCAGCAGAAACCCGGCAAGGC

CGTGAAGCTGCTGATCTACAGCACCAGCAGCCTGAATAGCGGCGTGCCCAGCAGATTTTCTGGC

AGCGGCTCTGGCACCGACTTCACCCTGACCATATCTAGCCTGCAGCCTGAGGACTTCGCCACCT

ACTACTGCCAGCAGTACAGCGAGCTGCCCTACACATTTGGCGGAGGCACCAAGGTGGAACTGAA

GCGTACGGTTGCTGCCCCTTCCGTGTTCATCTTCCCACCTTCCGACGAGCAGCTGAAGTCTGGC

ACAGCCTCTGTCGTGTGCCTGCTGAACAACTTCTACCCTCGGGAAGCCAAGGTGCAGTGGAAGG

TGGACAATGCCCTGCAGTCCGGCAACTCCCAAGAGTCTGTGACCGAGCAGGACTCCAAGGACAG

CACCTACAGCCTGTCCTCCACACTGACCCTGTCCAAGGCCGACTACGAGAAGCACAAGGTGTAC

GCCTGCGAAGTGACCCATCAGGGCCTGTCTAGCCCTGTGACCAAGTCTTTCAACCGGGGCGAGT

GTTAG

-continued

HFB3-18-hG1 (mouse monoclonal antibody)
CDR-H1:

(SEQ ID NO: 51)
GETESDAW

CDR-H2:

(SEQ ID NO: 52)
VRNKANNHATYYAESVKG

CDR-H3:

(SEQ ID NO: 53)
TRSVGGYGTTYWYFDV

CDR-L1:

(SEQ ID NO: 54)
QNLLNSGNQKNY

CDR-L2:

(SEQ ID NO: 55)
GASTRESGVPD

CDR-L3:

(SEQ ID NO: 56)
QSEHSYPYT

HCVR IS SEQ ID NO: 57, AND LCVR IS SEQ ID NO: 58.

HC:

(SEQ ID NO: 59)
EVKLEESGGGLVQPGGSMKLSCAASGFTFSDAWMDWVRQSPEKGLEWVAEVRNKANNHATYYAE

SVKGRFTISRDDSKSSVYLQMNSLRAEDTGIYYCTRSVGGYGTTYWYFDVWGTGTTVTVSSAST

KGPSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYPSD lAVEWESNGQPENNYKTTPPVLDSDGSFFLYSKLTVDKSRWQQGNVFSCSVMHEALHNHYTQKS

LSLSPGK

LC:

(SEQ ID NO: 60)
DIVMTQSPSSLSVSAGEKVTMSCKSSQNLLNSGNQKNYLAWYQQKPGQPPKLLIFGASTRESGV

PDRFTGSGSGTDFTLTISSVQAEDLAVYYCQSEHSYPYTFGGGTKLEIKRTVAAPSVFIFPPSD

EQLKSGTASVVCLLNNFYPREAKVQWKVDNALQSGNSQESVTEQDSKDSTYSLSSTLTLSKADY

EKHKVYACEVTHQGLSSPVTKSFNRGEC (SEQ ID NO: 61)
GAAGTGAAGCTGGAAGAATCTGGCGGCGGACTGGTTCAGCCTGGCGGATCTATGAAGCTGAGCT

GTGCCGCCAGCGGCTTCACCTTTTCTGACGCCTGGATGGACTGGGTCCGACAGTCTCCTGAGAA

AGGCCTGGAATGGGTTGCCGAAGTGCGGAACAAGGCCAACAACCACGCCACCTACTACGCCGAG

TCTGTGAAGGGCAGATTCACCATCAGCCGGGACGACAGCAAGAGCAGCGTGTACCTGCAGATGA

ACAGCCTGAGAGCCGAGGACACCGGCATCTACTACTGCACAAGAAGCGTTGGCGGCTACGGCAC

CACCTACTGGTACTTTGATGTGTGGGGCACCGGCACCACAGTGACCGTTAGTTCTGCGTCGACC

AAGGGCCCATCGGTCTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGGAACTCAGGCGCCCT

GACCAGCGGCGTGCACACCTTCCCGGCTGTCCTACAGTCCTCAGGACTCTACTCCCTCAGCAGC

GTGGTGACCGTGCCCTCCAGCAGCTTGGGCACCCAGACCTACATCTGCAACGTGAATCACAAGC

CCAGCAACACCAAGGTGGACAAGAAAGTTGAGCCCAAATCTTGTGACAAAACTCACACATGCCC

ACCGTGCCCAGCACCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGACGTGAGCCACGAAG

ACCCTGAGGTCAAGTTCAACTGGTACGTGGACGGCGTGGAGGTGCATAATGCCAAGACAAAGCC

GCGGGAGGAGCAGTACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCTGCCCCCATCCCG

GGAGGAGATGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAGGTGGCAGCA

GGGGAACGTCTTCTCATGCTCCGTGATGCATGAGGCTCTGCACAACCACTACACGCAGAAGAGC

CTCTCCCTGTCCCCGGGTAAATGA (SEQ ID NO: 62)

GACATCGTGATGACACAGAGCCCTAGCAGCCTGTCTGTGTCTGCCGGCGAGAAAGTGACCATGA

GCTGCAAGAGCAGCCAGAACCTGCTGAACAGCGGCAACCAGAAGAACTACCTGGCCTGGTATCA

GCAGAAGCCCGGCCAGCCTCCTAAGCTGCTGATCTTTGGAGCCAGCACCAGAGAAAGCGGCGTG

CCCGATAGATTTACAGGCTCTGGCAGCGGCACCGACTTCACCCTGACAATCAGTTCTGTGCAGG

CCGAGGACCTGGCCGTGTACTACTGTCAGAGCGAGCACAGCTACCCCTACACCTTTGGCGGCGG

AACAAAGCTGGAAATCAAGCGTACGGTGGCTGCACCATCTGTCTTCATCTTCCCGCCATCTGAT

GAGCAGTTGAAATCTGGAACTGCCTCTGTTGTGTGCCTGCTGAATAACTTCTATCCCAGAGAGG

CCAAAGTACAGTGGAAGGTGGATAACGCCCTCCAATCGGGTAACTCCCAGGAGAGTGTCACAGA

GCAGGACAGCAAGGACAGCACCTACAGCCTCAGCAGCACCCTGACGCTGAGCAAAGCAGACTAC

GAGAAACACAAAGTCTACGCCTGCGAAGTCACCCATCAGGGCCTGAGCTCGCCCGTCACAAAGA

GCTTCAACAGGGGAGAGTGTTAG

HFB3-18hz1-hG1 (humanized monoclonal antibody)
CDR-H1:

(SEQ ID NO: 63)

GETESDAW

CDR-H2:

(SEQ ID NO: 64)

VRNKANNHATYYAASVKG

CDR-H3:

(SEQ ID NO: 65)

TRSVGGYGTTYWYFDV

CDR-L1:

(SEQ ID NO: 66)

QNLLNSGNQKNY

CDR-L2:

(SEQ ID NO: 67)

GASTRESGVPD

CDR-L3:

(SEQ ID NO: 68)

QSEHSYPYT

HCVR IS SEQ ID NO: 69, AND LCVR IS SEQ ID NO: 70.

HC:

(SEQ ID NO: 71)

EVQLVESGGGLVQPGGSLKLSCAASGETFSDAWMDWVRQASGKGLEWVGEVRNKANNHATYYAA

SVKGRFTISRDDSKNTAYLQMNSLKTEDTAVYYCTRSVGGYGTTYWYFDVWGQGTTVTVSSAST

KGPSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNSTYRVVSVLTVLHQD

-continued

WLNGKEYKCKVSNKALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCSVMHEALHNHYTQKS

LSLSPGK

LC:
                                                        (SEQ ID NO: 72)
DIVMTQSPDSLAVSLGERATINCKSSQNLLNSGNQKNYLAWYQQKPGQPPKLLIFGASTRESGV

PDRFSGSGSGTDFTLTISSLQAEDVAVYYCQSEHSYPYTFGQGTKLEIKRTVAAPSVFIFPPSD

EQLKSGTASVVCLLNNFYPREAKVQWKVDNALQSGNSQESVTEQDSKDSTYSLSSTLTLSKADY

EKHKVYACEVTHQGLSSPVTKSFNRGEC (SEQ ID NO: 73)
GAGGTGCAGCTGGTTGAATCTGGCGGAGGACTGGTTCAGCCTGGCGGATCTCTGAAGCTGTCTT

GTGCCGCCAGCGGCTTCACCTTTTCCGACGCTTGGATGGACTGGGTCCGACAGGCCTCTGGCAA

AGGCCTTGAGTGGGTTGGAGAAGTGCGGAACAAGGCCAACAACCACGCCACCTACTATGCCGCC

TCTGTGAAGGGCAGATTCACCATCAGCCGGGACGACAGCAAGAACACCGCCTACCTGCAGATGA

ACAGCCTGAAAACCGAGGACACCGCCGTGTACTACTGCACCAGATCTGTTGGCGGCTACGGCAC

CACCTACTGGTACTTTGATGTGTGGGGCCAGGGCACCACCGTGACAGTTTCTTCTGCGTCGACC

AAGGGCCCATCGGTCTTCCCCCTGGCACCCTCCTCCAAGAGCACCTCTGGGGGCACAGCGGCCC

TGGGCTGCCTGGTCAAGGACTACTTCCCCGAACCGGTGACGGTGTCGTGGAACTCAGGCGCCCT

GACCAGCGGCGTGCACACCTTCCCGGCTGTCCTACAGTCCTCAGGACTCTACTCCCTCAGCAGC

GTGGTGACCGTGCCCTCCAGCAGCTTGGGCACCCAGACCTACATCTGCAACGTGAATCACAAGC

CCAGCAACACCAAGGTGGACAAGAAAGTTGAGCCCAAATCTTGTGACAAAACTCACACATGCCC

ACCGTGCCCAGCACCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGACGTGAGCCACGAAG

ACCCTGAGGTCAAGTTCAACTGGTACGTGGACGGCGTGGAGGTGCATAATGCCAAGACAAAGCC

GCGGGAGGAGCAGTACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCTGCCCCCATCCCG

GGAGGAGATGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAGGTGGCAGCA

GGGGAACGTCTTCTCATGCTCCGTGATGCATGAGGCTCTGCACAACCACTACACGCAGAAGAGC

CTCTCCCTGTCCCCGGGTAAATGA (SEQ ID NO: 74)
GACATCGTGATGACACAGAGCCCTGATAGCCTGGCCGTGTCTCTGGGAGAGAGAGCCACCATCA

ACTGCAAGAGCAGCCAGAACCTGCTGAACAGCGGCAACCAGAAGAACTACCTGGCCTGGTATCA

GCAGAAGCCCGGCCAGCCTCCTAAGCTGCTGATCTTTGGAGCCAGCACCAGAGAAAGCGGCGTG

CCCGATAGATTTTCTGGCAGCGGCTCTGGCACCGACTTCACCCTGACAATTAGCTCCCTGCAGG

CCGAGGATGTGGCCGTGTACTACTGTCAGAGCGAGCACAGCTACCCCTACACCTTTGGCCAGGG

CACCAAGCTGGAAATCAAGCGTACGGTGGCTGCACCATCTGTCTTCATCTTCCCGCCATCTGAT

GAGCAGTTGAAATCTGGAACTGCCTCTGTTGTGTGCCTGCTGAATAACTTCTATCCCAGAGAGG

CCAAAGTACAGTGGAAGGTGGATAACGCCCTCCAATCGGGTAACTCCCAGGAGAGTGTCACAGA

GCAGGACAGCAAGGACAGCACCTACAGCCTCAGCAGCACCCTGACGCTGAGCAAAGCAGACTAC

-continued

GAGAAACACAAAGTCTACGCCTGCGAAGTCACCCATCAGGGCCTGAGCTCGCCCGTCACAAAGA

GCTTCAACAGGGGAGAGTGTTAG (SEQ ID NO: 75)

RPGWYCALSKQEGCRLCAPLRKCRPGFGVARPGTETSD

In some embodiment, the monoclonal antibodies of the invention or antigen-binding fragments thereof are human-mouse chimeric antibodies, humanized antibodies, human antibodies, CDR-grafted antibodies, or resurfaced antibodies.

In some embodiments, the antigen-binding fragment thereof is an Fab, Fab', F(ab')$_2$, F$_d$, single chain Fv or scFv, disulfide linked Fv, V-NAR domain, IgNar, intrabody, IgG$\Delta$CH$_2$, minibody, F(ab')$_3$, tetrabody, triabody, diabody, single-domain antibody, DVD-Ig, Fcab, mAb$_2$, (scFv)$_2$, or scFv-Fc.

In some embodiment, the monoclonal antibodies of the invention or antigen-binding fragments thereof has an engineered Fc region that abolishes immune effector function. For example, the engineered Fc region of the subject antibody may have a "LALA" double mutation (Leu234Ala together with Leu235Ala) and thus have diminished effector function. Such antibodies may have the designation of G1AA for having the LALA double mutation on IgG1.

Other recombinant human IgG antibodies (hIgGs) partially or completely devoid of binding to Fcγ receptors (FcγRs) and complement protein C1q, and thus with abolished immune effector functions, are known in the art, and are of use for various therapeutic applications in order to reduce FcγR activation and Fc-mediated toxicity. Certain such Fc-engineered antibodies/fragments partially achieve this goal, while others completely abolishes FcγR activation and Fc-mediated toxicity. In certain embodiments, the antibody/fragment of the invention has an engineered hIgG Fc domain comprising hIgG1-P329G LALA or hIgG4-P329G SPLE (the human IgG4 S228P/L235E variant of IgG4) mutations, with completely abolish FcγR and C1q interactions, and with unaffected FcRn interactions and Fc stability. The P329G Fc mutation disrupts the formation of a proline sandwich motif with the FcγRs. As this motif is present in the interface of all IgG Fc/FcγR complexes, its disruption can be applied to all human and most of the other mammalian IgG subclasses to create effector silent IgG molecules. Thus in certain embodiments, the subject antibody/fragment has any one IgG subclass with such effector silent Fc mutation.

In certain embodiments, the monoclonal antibodies of the invention or antigen-binding fragments thereof are specific for human TNFR2, e.g., substantially do not cross-react with TNFR1, and/or substantially do not cross-react with mouse TNFR2. In certain embodiments, the monoclonal antibodies of the invention or antigen-binding fragments thereof cross-react with a monkey TNFR2, such as a cynomolgus monkey or rhesus monkey TNFR2.

In some embodiments, the monoclonal antibody of the invention or antigen-binding fragment thereof has a dissociation constant (K$_d$) of ≤1 μM, ≤100 nM, ≤50 nM, ≤25 nM, ≤20 nM, ≤15 nM, ≤10 nM, ≤5 nM, ≤2 nM, ≤1 nM, ≤0.1 nM, ≤0.01 nM, or ≤0.001 nM (e.g. 10$^{-8}$ M or less, e.g. from 10$^{-8}$M to 10$^{-13}$ M, e.g., from 10$^{-9}$M to 10$^{-13}$ M) for rhTNFR2.

In some embodiments, the monoclonal antibodies of the invention or antigen-binding fragments thereof bind to a region within the CRD2 domain of the TNFR2. In certain embodiment, the monoclonal antibodies of the invention or antigen-binding fragments thereof bind to the epitope bound by HFB3-1.

In some embodiments, the monoclonal antibodies of the invention or antigen-binding fragments thereof bind to a region within the CRD3 domain of the TNFR2. In certain embodiment, the monoclonal antibodies of the invention or antigen-binding fragments thereof bind to the epitope bound by HFB3-14.

In certain embodiment, the monoclonal antibodies of the invention or antigen-binding fragments thereof bind to the epitope bound by HFB3-18.

In certain embodiment, the monoclonal antibodies of the invention or antigen-binding fragments thereof bind to the epitope of SEQ ID NO: 13 or 38.

In some embodiments, the monoclonal antibodies of the invention or antigen-binding fragments thereof enhance the binding of human recombinant TNFα to TNFR2.

In some embodiments, the monoclonal antibodies of the invention or antigen-binding fragments thereof block the binding of human recombinant TNFα to TNFR2.

In some embodiments, the monoclonal antibodies of the invention or antigen-binding fragments thereof substantially do not affect binding of human recombinant TNFα to TNFR2.

In some embodiments, the monoclonal antibodies of the invention or antigen-binding fragments thereof inhibit TNFα-mediated signaling, such as NFκB signaling, and/or induce down-regulation of NFκB downstream target genes. In other embodiments, however, the monoclonal antibodies of the invention or antigen-binding fragments thereof promote TNFα-mediated signaling, such as NFκB signaling, and/or induce up-regulation of NFκB downstream target genes.

In some embodiments, NFκB signaling is stimulated in effector T cells, such as CD8 and/or CD4 Tconv T cells. In some other embodiments, NFκB signaling is inhibited in effector T cells, such as CD8 and/or CD4 Tconv T cells.

In some embodiments, NFκB signaling is stimulated in Tregs. In some other embodiments, NFκB signaling is inhibited in Tregs.

In some embodiments, the monoclonal antibodies of the invention or antigen-binding fragments thereof stimulate CD8 and/or conventional CD4 T cell proliferation, optionally with or without co-stimulation by CD3/CD28, and/or optionally with or without TNFα co-stimulation.

In some embodiments, the monoclonal antibodies of the invention or antigen-binding fragments thereof, particularly humanized monoclonal antibodies or antigen-binding fragments thereof, preferentially bind to (CD3/CD28) TCR-activated primary CD8 and/or CD4 T cells as compared to unstimulated primary CD8 and/or CD4 T cells.

In some embodiments, the monoclonal antibodies of the invention or antigen-binding fragments thereof, particularly humanized monoclonal antibodies or antigen-binding fragments thereof, enhance CD3/CD28-induced activation and/or proliferation, such as CD3/CD28-induced activation and/or proliferation of primary CD8 and/or CD4 T cells, including activation and/or proliferation of primary CD8 and/or CD4 T cells in the presence of Tregs.

In some embodiments, the monoclonal antibodies of the invention or antigen-binding fragments thereof, particularly humanized monoclonal antibodies or antigen-binding fragments thereof, co-stimulate activation and/or proliferation of primary CD8 and/or CD4 T cells in a cross-linking independent manner.

In some embodiments, the monoclonal antibodies of the invention or antigen-binding fragments thereof, particularly humanized monoclonal antibodies or antigen-binding fragments thereof, co-stimulate activation and/or proliferation of primary CD8 and/or CD4 T cells in a cross-linking dependent manner.

In some embodiments, the monoclonal antibody or antigen-binding fragment thereof of the invention enhances binding between TNF$\alpha$ and TNFR2; enhances TNF$\alpha$-mediated or -co-stimulated NF$\kappa$B signaling (e.g., in TCR-activated CD8 and/or CD4 Tconv T cells); and/or promotes TCR-activated effector T cell (e.g., CD8 and/or CD4 Tconv T cell) proliferation in the presence of Treg.

In some embodiments, the monoclonal antibody or antigen-binding fragment thereof of the invention enhances TNF$\alpha$-mediated CD25 expression on Tregs.

In some embodiments, the monoclonal antibodies of the invention or antigen-binding fragments thereof, including humanized monoclonal antibodies or antigen-binding fragments thereof, have good developability profile, including being stable under high temperature (e.g., 25° C. or 40° C.), low pH conditions (e.g., pH3.5 around room temperature), and/or following several rounds of freeze/thaw cycles.

In certain embodiments, the monoclonal antibodies of the invention or antigen-binding fragments thereof, including humanized monoclonal antibodies or antigen-binding fragments thereof, include one or more point mutations of in amino acid sequences that are designed to improve developability of the antibody. For example, Raybould et al. (Five computational developability guidelines for therapeutic antibody profiling, PNAS 116(10): 4025-4030, 2019) described Therapeutic Antibody Profiler (TAP), a computational tool that builds downloadable homology models of variable domain sequences, tests them against five developability guidelines, and reports potential sequence liabilities and canonical forms. The authors further provide TAP as freely available at opig.stats.ox.ac.uk/webapps/sabdab-sabpred/TAP.php.

There are many barriers to therapeutic mAb development, besides achieving the desired affinity to the antigen. These include intrinsic immunogenicity, chemical and conformational instability, self-association, high viscosity, polyspecificity, and poor expression. For example, high levels of hydrophobicity, particularly in the highly variable complementarity-determining regions (CDRs), have repeatedly been implicated in aggregation, viscosity, and polyspecificity. Asymmetry in the net charge of the heavy- and light-chain variable domains is also correlated with self-association and viscosity at high concentrations. Patches of positive and negative charge in the CDRs are linked to high rates of clearance and poor expression levels. Product heterogeneity (e.g., through oxidation, isomerization, or glycosylation) often results from specific sequence motifs liable to post- or co-translational modification. Computational tools are available to facilitate the identification of sequence liabilities. Warszawski et al. (Optimizing antibody affinity and stability by the automated design of the variable light-heavy chain interfaces. *PLoS Comput Biol* 15(8): e1007207. https://doi.org/10.1371/journal.pcbi.1007207) also described methods of optimizing antibody affinity and stability by an automated design of the variable light-heave chain interfaces. Additional methods are available to identify potential developability issues of a candidate antibody, and in preferred embodiments of this invention, one or more point mutations can be introduced, via conventional methods, to the candidate antibody to address such issues to lead to an optimized therapeutic antibody of the invention.

7. Humanized Antibodies

In some embodiments, the antibody of the invention is a humanized antibody. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

An antibody may be humanized by any standard method. Non-limiting exemplary methods of humanization include methods described, e.g., in U.S. Pat. Nos. 5,530,101; 5,585,089; 5,693,761; 5,693,762; 6,180,370; Jones et al., Nature 321:522-525 (1986); Riechmann et al, Nature 332: 323-27 (1988); Verhoeyen et al, Science 239: 1534-36 (1988); and U.S. Publication No. US 2009/0136500. All incorporated by reference.

A humanized antibody is an antibody in which at least one amino acid in a framework region of a non-human variable region has been replaced with the amino acid from the corresponding location in a human framework region. In some embodiments, at least two, at least three, at least four, at least five, at least six, at least seven, at least eight, at least nine, at least 10, at least 11, at least 12, at least 15, or at least 20 amino acids in the framework regions of a non-human variable region are replaced with an amino acid from one or more corresponding locations in one or more human framework regions.

In some embodiments, some of the corresponding human amino acids used for substitution are from the framework regions of different human immunoglobulin genes. That is, in some such embodiments, one or more of the non-human amino acids may be replaced with corresponding amino acids from a human framework region of a first human antibody or encoded by a first human immunoglobulin gene, one or more of the non-human amino acids may be replaced with corresponding amino acids from a human framework region of a second human antibody or encoded by a second human immunoglobulin gene, one or more of the non-human amino acids may be replaced with corresponding amino acids from a human framework region of a third human antibody or encoded by a third human immunoglobulin gene, etc. Further, in some embodiments, all of the corresponding human amino acids being used for substitution in a single framework region, for example, FR2, need not be from the same human framework. In some embodiments, however, all of the corresponding human amino acids being used for substitution are from the same human antibody or encoded by the same human immunoglobulin gene.

In some embodiments, an antibody is humanized by replacing one or more entire framework regions with corresponding human framework regions. In some embodiments, a human framework region is selected that has the highest level of homology to the non-human framework region being replaced. In some embodiments, such a humanized antibody is a CDR-grafted antibody.

In some embodiments, following CDR-grafting, one or more framework amino acids are changed back to the corresponding amino acid in a mouse framework region. Such "back mutations" are made, in some embodiments, to retain one or more mouse framework amino acids that appear to contribute to the structure of one or more of the CDRs and/or that may be involved in antigen contacts and/or appear to be involved in the overall structural integrity of the antibody. In some embodiments, ten or fewer, nine or fewer, eight or fewer, seven or fewer, six or fewer, five or fewer, four or fewer, three or fewer, two or fewer, one, or zero back mutations are made to the framework regions of an antibody following CDR grafting.

In some embodiments, a humanized antibody also comprises a human heavy chain constant region and/or a human light chain constant region.

8. Human Antibodies

In some embodiments, the antibody of the invention is a human antibody. Human antibodies can be made by any suitable method. Non-limiting exemplary methods include making human antibodies in transgenic mice that comprise human immunoglobulin loci. See, e.g., Jakobovits et al., Proc. Natl. Acad. Sci. USA 90: 2551-55 (1993); Jakobovits et al, Nature 362: 255-8 (1993); onberg et al, Nature 368: 856-9 (1994); and U.S. Pat. Nos. 5,545,807; 6,713,610; 6,673,986; 6,162,963; 5,545,807; 6,300,129; 6,255,458; 5,877,397; 5,874,299; and 5,545,806.

Non-limiting exemplary methods also include making human antibodies using phage display libraries. See, e.g., Hoogenboom et al., J. Mol. Biol. 227: 381-8 (1992); Marks et al, J. Mol. Biol. 222: 581-97 (1991); and PCT Publication No. WO 99/10494.

Antibody Constant Regions

In some embodiments, a humanized, chimeric, or human antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region, for example, human IgG1, IgG2, IgG3, or IgG4. In some embodiments, an antibody or Fc fusion partner comprises a C237S mutation, for example, in an IgG1 constant region. In some embodiments, an antibody described herein comprises a human IgG2 heavy chain constant region. In some such embodiments, the IgG2 constant region comprises a P331S mutation, as described in U.S. Pat. No. 6,900,292. In some embodiments, an antibody described herein comprises a human IgG4 heavy chain constant region. In some such embodiments, an antibody described herein comprises an S241P mutation in the human IgG4 constant region. See, e.g., Angal et al. Mol. Immunol. 30(1):105-108 (1993). In some embodiments, an antibody described herein comprises a human IgG4 constant region and a human κ light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound. Typically, antibodies comprising human IgG1 or IgG3 heavy chains have effector function.

In some embodiments, effector function is not desirable. For example, in some embodiments, effector function may not be desirable in treatments of inflammatory conditions and/or autoimmune disorders. In some such embodiments, a human IgG4 or IgG2 heavy chain constant region is selected or engineered. In some embodiments, an IgG4 constant region comprises an S241P mutation.

Any of the antibodies described herein may be purified by any suitable method. Such methods include, but are not limited to, the use of affinity matrices or hydrophobic interaction chromatography. Suitable affinity ligands include the antigen and/or epitope to which the antibody binds, and ligands that bind antibody constant regions. For example, a Protein A, Protein G, Protein A/G, or an antibody affinity column may be used to bind the constant region and to purify an antibody.

In some embodiments, hydrophobic interactive chromatography (HIC), for example, a butyl or phenyl column, is also used for purifying some polypeptides. Many methods of purifying polypeptides are known in the art.

Alternatively, in some embodiments, an antibody described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al, Biotechnol. Adv. 21: 695-713 (2003).

9. Nucleic Acid Molecules Encoding Antibodies of the Invention

The invention also provides nucleic acid molecules comprising polynucleotides that encode one or more chains of an antibody described herein. In some embodiments, a nucleic acid molecule comprises a polynucleotide that encodes a heavy chain or a light chain of an antibody described herein. In some embodiments, a nucleic acid molecule comprises both a polynucleotide that encodes a heavy chain and a polynucleotide that encodes a light chain, of an antibody described herein. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody described herein comprises a nucleotide sequence that encodes a leader sequence, which, when translated, is located at the N-terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell, such as a mammalian cell.

10. Vectors

Vectors comprising polynucleotides that encode heavy chains and/or light chains of the antibodies described herein are provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., Biotechnol. Prog. 20:880-889 (2004). In some embodiments, a vector is chosen for in vivo expression of the subject antibodies in animals, including humans. In some such embodiments, expression of the polypeptide or polypeptides is under the control of a promoter or promoters that function in a tissue-specific manner. For example, liver-specific promoters are described, e.g., in PCT Publication No. WO 2006/076288.

11. Host Cells

In various embodiments, heavy chains and/or light chains of the antibodies described herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, heavy chains and/or light chains of the antibodies described herein may be expressed in yeast. See, e.g., U.S. Publication No. US 2006/0270045 A1. In some embodiments, a particular eukaryotic host cell is selected based on its ability to make desired post-translational modifications to the heavy chains and/or light chains of TNFR2 antibody. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc., Nonlimiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

EXAMPLES

Example 1 Monoclonal Antibodies Specific for Human and Monkey TNFR2

To raise monoclonal antibodies specific for human TNFR2 with cross-reactivity to the monkey ortholog TNFR2, mice was immunized with the recombinant extracellular domain (ECD) of human TNFR2 (rhTNFR2) using standard procedure to generate a series of diverse human-mouse chimeric monoclonal antibodies.

Figure 1:
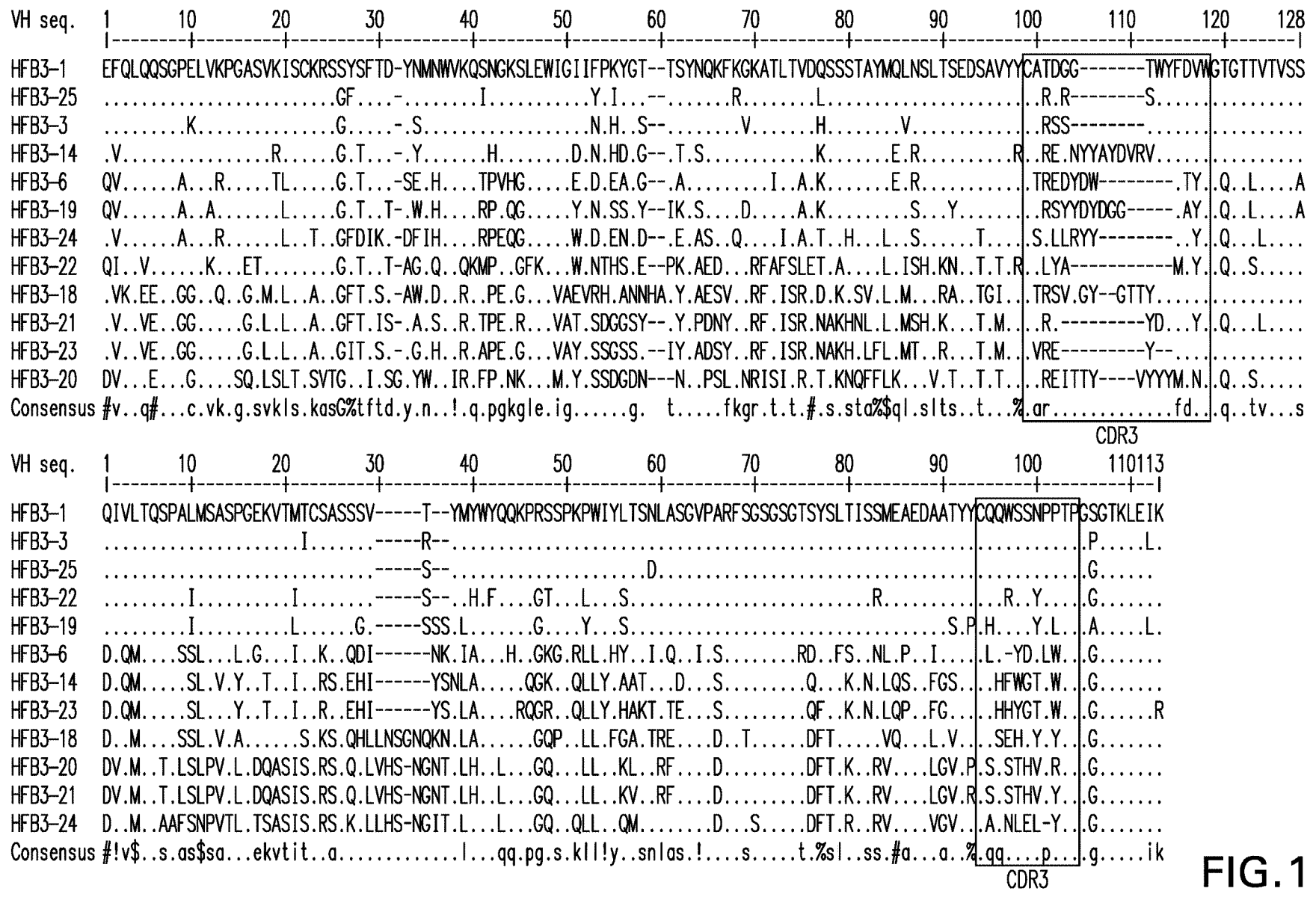

At least 25 such monoclonal antibodies were generated, the VH and VL sequences of selected antibodies were aligned, and the consensus sequences were obtained, as shown in FIG. 1. The H-CDR3 and L-CDR3 regions are marked by boxed sequences.

These monoclonal antibodies were then tested for their abilities to bind human and monkey TNFR2 expressed by CHO cells (CHO.hHFB3 and CHO.mkHFB3 cells respectively). Briefly, about 40,000 CHO.hHFB3 or CHO.mkHFB3 cells were seeded in tissue culture wells, and serial 1:3 dilutions of each test antibodies, with starting (highest) concentration of about 66 nM antibody, were added to each cell type and incubated for about an hour. Antibodies bound to the cells were detected by using 17 nM of anti-human Fc antibody labeled by AF647 (ALEXSA FLUOR® 647 fluorescent dye). An isotype matched negative control antibody was also used in this assay. The data, including $EC_{50}$ values and $E_{max}$ for each antibody, were compiled in FIG. 2A.

Eleven (11) of the test antibodies showed sub- or single digit-nM level of affinity ($EC_{50}$) against hTNFR2 expressed on CHO cells. These antibodies also showed cross-reactivity against rhesus monkey ortholog of TNFR2 expressed on CHO cells, with substantially the same trend for binding affinity as compared to hTNFR2 binding. See FIG. 2A.

Interestingly, some of the antibodies (such as HFB3-1 and -14) promoted TNFα binding to TNFR2, others (such as HFB3-18) inhibited TNFα binding to TNFR2, and yet others (such as HFB3-6) had apparently no effect on TNFα binding to TNFR2. See FIG. 2B. Specifically, binding of 25 ng/mL TNFα to CHO.hHFB3 cells were measured after pre-incubating the CHO cells with the respective antibodies for about an hour. The percentage of cells bound to TNFα (labeled as HFB2003L) was then plotted against increasing concentrations of the antibodies.

The same experiments were also set up to test the ability of the test antibodies to bind CHO cells expressing mouse TNFR2 and the parental CHO cell lines (which may or may not express hamster TNFR2). Two monoclonal antibodies (HFB3-18 and HFB3-19) exhibited marginal levels of binding to the mouse ortholog, while no other antibodies had detectable level of binding to the mouse TNFR2. As a positive control, the HM102 monoclonal antibody specific for mouse TNFR2 was used to show positive binding to the CHO cells expressing mouse TNFR2, while the isotype matched control antibody did not bind (FIG. 3).

No binding was observed for the parental CHO cell line (FIG. 3).

Binding specificity towards human TNFR2 (vs. the related TNFR1 receptor) was also verified using recombinant human TNFR2 and TNFR1 proteins.

Briefly, tissue culture plates were coated with either 0.1 μg/mL of His-tagged recombinant human TNFR2 or TNFR1 overnight at 4° C. The coated plates were then incubated for about 1 hour on ice with 1:3 serial dilutions of each test antibodies, with starting (highest) concentration of about 66 nM antibody. Antibodies bound to the cells were detected by using 1:5000 dilution of HRP-labeled anti-human Fc antibody and TMB substrate. Isotype matched negative control antibody F3, as well as the MR2-1 positive control antibody specific for rhTNFR2 and a positive control antibody specific for rhTNFR1 were also used in this assay. The data, including $EC_{50}$ values for each antibody, were compiled in FIG. 4A.

Six of the 11 tested antibodies, namely HFB3-1, -14, -21, -23, -24, and -25 showed sub-nM affinity ($EC_{50}$) towards the His-tagged monomeric rhTNFR2, while 4 additional ones (HFB-3, -6, -19, and -22) showed single digit-nM affinity towards the same antigen. HFB3-18 showed relatively the weakest binding to the monomeric rhTNFR2 with double digit nM affinity. However, none of the 11 antibodies showed any detectable level of binding towards the His-tagged TNFR1 receptor, demonstrating binding specificity for TNFR2.

Binding affinity of human-mouse chimeric antibodies HFB3-1, 14 and 18 to recombinant human TNFR2 protein was verified using Anti-human IgG Fc Capture (AHC) biosensor. AHC biosensors enable kinetic characterization of macromolecular interactions between human Fc-containing proteins (e.g., the subject antibodies) and target analytes (e.g., recombinant human TNFR2). Immobilization of human Fc-containing proteins is achieved through a factory immobilized anti-human Fc-specific antibody whose high-affinity for the human Fc domain provides the stable baseline required for demanding kinetics applications. In this specific experiment, the test antibodies (humanized \ were loaded at a concentration of 20 μg/mL in assay buffer (PBS, pH 7.4, 0.1% BSA, 0.1% Tween20). The analyte was His-tagged recombinant human TNFR2 at 500, 167, or 55.7 nM. The capture assay was run at 25° C. $K_d$ of tested antibodies are in the nM range (see FIG. 4B).

Figure 11A:
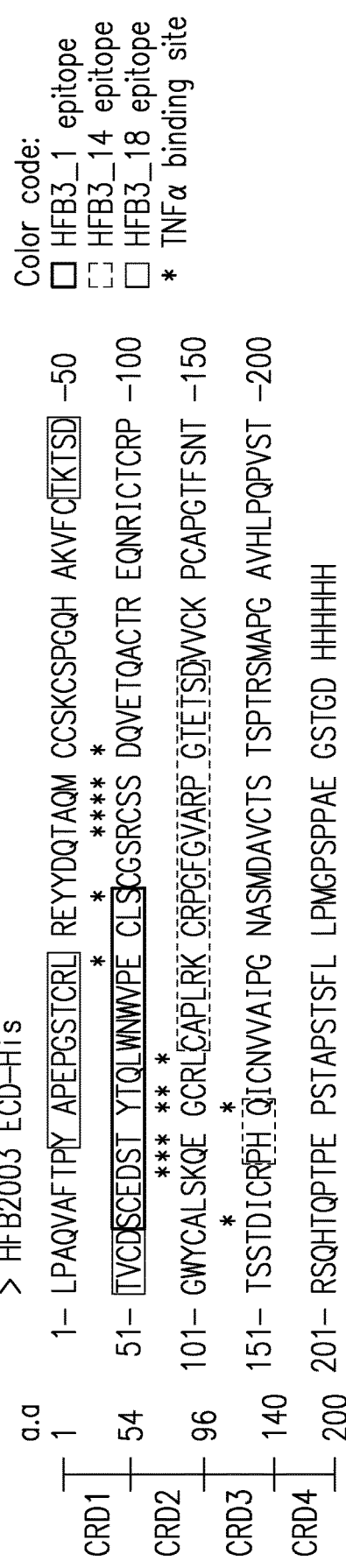

Epitope mapping experiments of HFB3-1-hG1, HFB3-14-hG1, HFB3-6-hG1, and HFB3-18-hG1 antibodies showed that these antibodies recognize different domains of TNFR2. HFB3-1-hG1 binds to a region within the CRD2 domain, while HFB3-18-hG1 binds to a conformational epitope within CDR1. HFB3-6-hG1 binds to a region within CRD3, and HFB3-14-hG1 also binds to an epitope within CRD3 region that is smaller than HFB3-6-hG1's epitope (see FIG. 11B). Locations of their epitopes on 3D-model of the TNFR2-TNFα complex can be visualized in FIG. 11C.

Example 2 Expression of TNFR2 in T Cell Subtypes

This experiment demonstrates that TNFR2 is predominantly expressed on Tregs as well as on CD4$^+$ and CD8$^+$ T cells in various cancer types.

T cell subtypes, including Tregs and CD4$^+$ and CD8$^+$ T cells, were isolated from the various tumor samples, and the relative percentage of the T cell subtypes in the tumor samples, as well as the average relative expression levels of TNRF2 (scale of 2-8) in the T cell subtypes, were determined using RNA sequence analysis. The results were compiled in FIG. 5.

In each tumor samples analyzed, including BCC or basal cell carcinoma, SCC or squamous cell carcinoma, melanoma, or NSCLC or non-small cell lung cancer, TNFR2 was predominantly and most frequently found in Tregs, as well as CD4$^+$ and CD8$^+$ T cells. In addition, the highest relative expression levels were also found in the Tregs. See FIG. 5, left panel. The data suggests that TNFR2 is an attractive target for cancer therapy.

Additional expression analysis of TNFR2 in SCC cancer samples was also conducted in conjunction with the expression of several immune-checkpoint genes, such as PD-1, TIM3, CTLA4, and 4-1BB. It was found that in exhausted CD8+ T cells, expression of TNFR2 was aligned with the expression of these immune checkpoint genes (FIG. 5, right panel), suggesting that combination therapy using anti-TNFR2 antibodies and inhibitors for these immune checkpoint genes would be therapeutically beneficial.

Example 3 Binding of Anti-TNFR2 Monoclonal Antibodies to Primary Treg, CD8 and CD4 Tconv Cells Given the expression pattern of TNFR2 on T cell subtypes (see Example 2), this experiment demonstrates that the subject anti-TNFR2 monoclonal antibodies can bind to primary T cell subtypes, preferentially to activated T cells.

Briefly, flat bottom 96-well plates were coated overnight at 4° C. by 10 nM of anti-CD3 antibody. Meanwhile, T cell subtypes including Tregs, CD8 or CD4 conventional T cells (Tconv) were isolated from human PBMC. Isolated T cell subtypes were deeded at a density of about 50,000 cells/well, in the presence of 6.6 nM of anti-CD28 antibody to co-stimulate primary T cells for about 3 days. The stimulated primary T cells were then treated with various concentrations of 1:3 serial dilution of anti-TNFR2 human-mouse chimeric monoclonal antibodies of the invention for 1 hour on ice, with the highest concentration being 66 nM. Bound chimeric antibodies were detected by adding 17 nM of anti-hFc antibody labeled by AF647 dye for 1 hour incubation on ice, followed by FACS analysis to detect AF647 signals.

Figure 6:
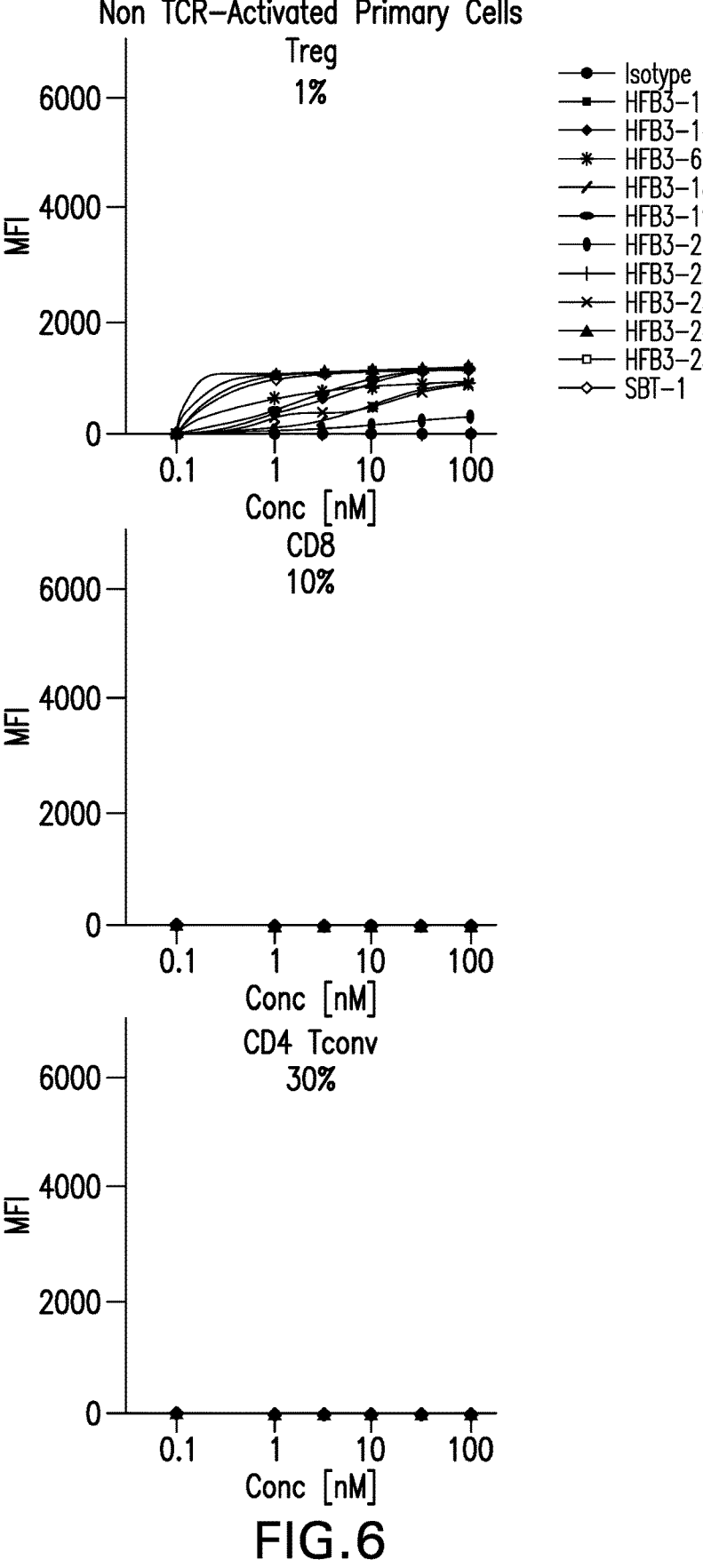
FIG. 6 shows cellular binding of anti-TNFR2 chimeric monoclonal antibodies on TCR-activated (bottom panel) and non-TCR-activated (top panel) primary Tregs, CD8, and CD4 Tconv. Primary T cells activated by CD3/CD28 co-stimulation (TCR activation) can be preferentially recognized by HFB3 antibodies.
Figure 6:
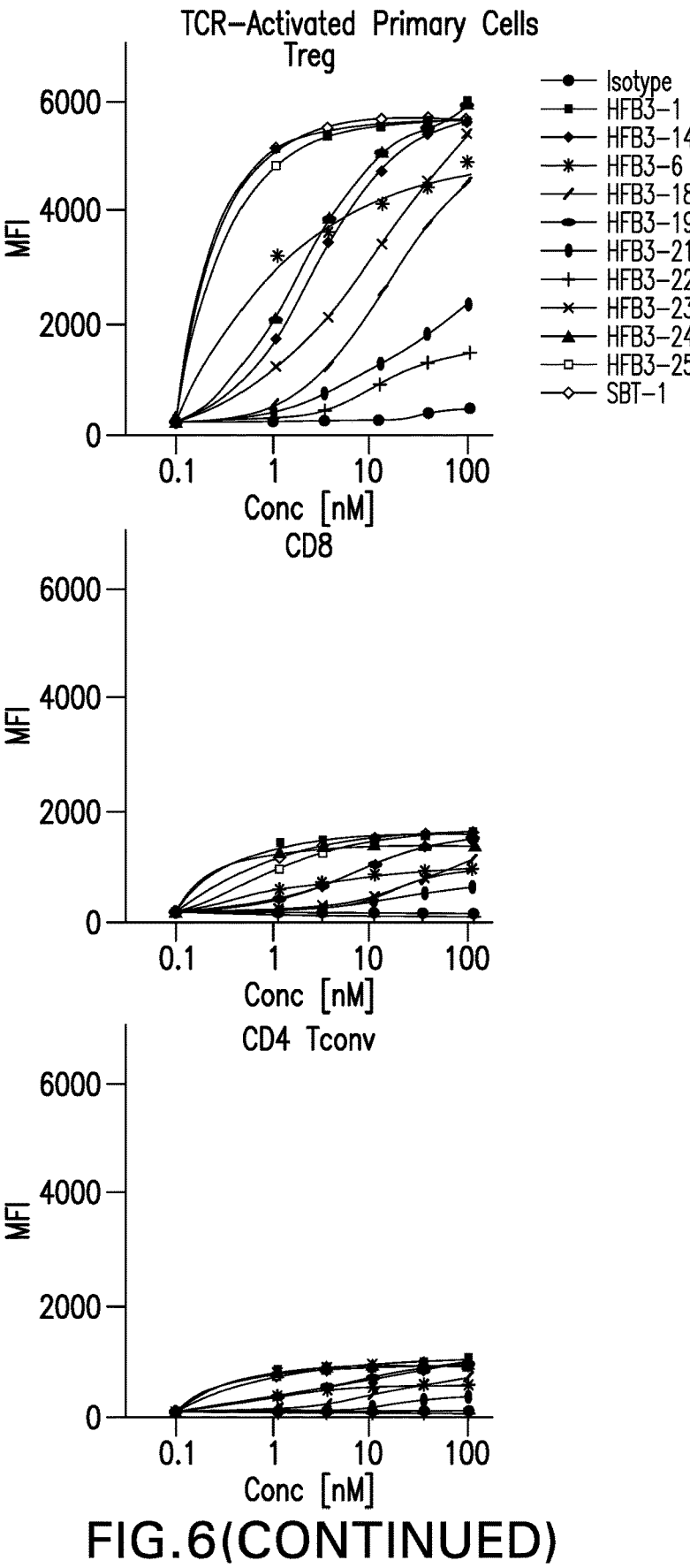

FIG. 6, top panel shows that the CD4 Tconv was the most abundant T cell subtype at about 30% of total hPBMC, followed by 10% CD8 T cell and about 1% Treg. However, non-TCR-activated primary T cells did not detectably bind the subject anti-TNFR2 antibodies, except that relatively low levels of binding occurred in primary Tregs. Overall, receptor occupancy Emax was the highest in Tregs, followed by CD8 then CD4 Tconv. Given the relatively low abundancy of the Tregs compared to the CD8 and CD4 Tconv, the expression of TNFR2 on Tregs was much higher than that on CD8 and CD4 T cells on per cell basis.

In TCR-activated T cells, however, a dramatic 5-6 fold increased binding was observed in Tregs for some anti-TNFR2 antibodies, while substantially higher binding in CD8 and CD4 Tconv were also observed (FIG. 6, lower panel).

Among the tested antibodies, HFB3-1, -6, -24, -25 and SBT1 (positive control) exhibited sub-nM level high affinity, while HFB3-14 and -19 exhibited single digit nM affinity. HFB3-18, -21, and -22 had double digit nM affinity.

Example 4 Binding of Certain Anti-TNFR2 Monoclonal Antibodies to Primary CD8 and CD4 Tconv Cells Co-Stimulated NFκB Signaling This experiment demonstrates that the anti-TNFR2 monoclonal antibodies of the invention co-stimulate TNFα-mediated NFκB signaling, as evidenced by QPCR quantitation of NFκB signaling pathway genes.

Figure 7:
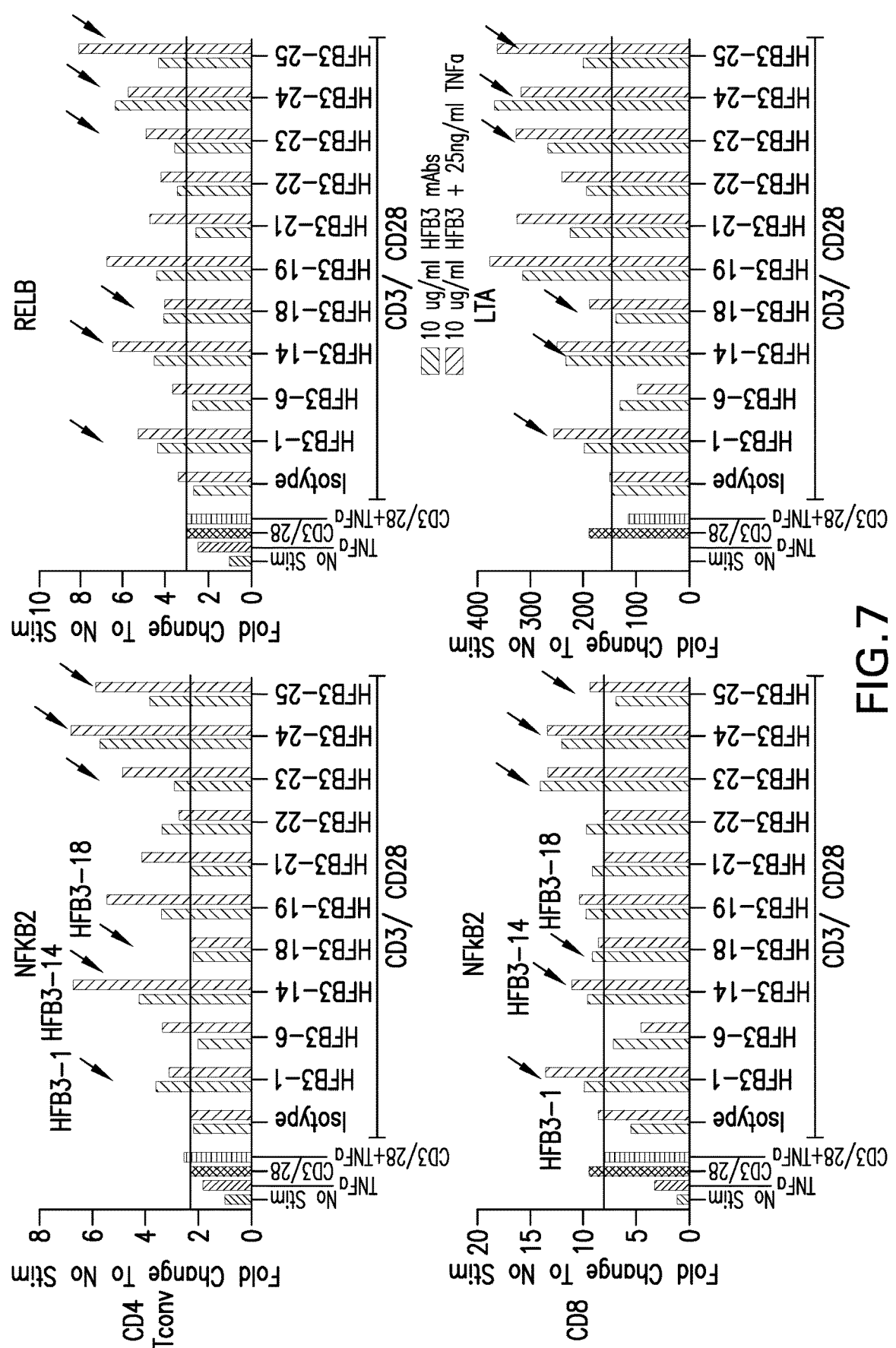
FIG. 7 shows that certain HFB3 antibodies of the invention, including HFB3-1, -14, -18, -23, -24, and -25, trigger NFκB signaling, and the effect can be enhanced in the presence of TNFα ligand.

Briefly, CD4 Tconv (CD4$^+$CD25$^-$) or CD8$^+$ T cells were isolated from hPBMC using standard techniques and commercially available kits. Isolated T cells were incubated with 10 Ng/mL (66 nM) of the various test monoclonal antibodies of the invention or proper positive or negative controls, together with 25 ng/mL (1.5 nM) of TNFα, for about 24 hours. The stimulated T cells were then harvested, and their mRNA was isolated, reverse transcribed, and subjected to QPCR analysis on selected NFκB signaling pathway genes such as CD25, Foxp3, NFκB2, RelB, and LTA. The expression levels of these genes in the presence and absence of co-stimulation by the subject antibodies were compared in the bar graph in FIG. 7. The results were presented as fold change compared to no stimulation control (1×).

The results showed that certain subject antibodies, including HFB3-1, -14, -23, -24, and -25 induced NFκB signaling. Of note, HFB3-1 and -14, but not HFB3-18, induced NFκB signaling from time to time, particularly in NFκB2, RelB and LTA.

Example 5 Co-Stimulatory Effect of Anti-TNFR2 Monoclonal Antibodies is Associated with Proliferation of Isolated Primary CD8 and CD4 Tconv Cells In this experiment, flat bottom 96-well plates were coated overnight at 4° C. by 10 nM anti-CD3 monoclonal antibody, as well as 20 or 100 nM of a subject anti-TNFR2 antibody. Meanwhile, CD8 and CD4 Tconv cells were isolated from hPBMC as described, and were labeled with 2 μM of CTV (CELLTRACE™ Violet Cell Proliferation Kit from Invitrogen) to track T cell proliferation. The CELLTRACE™ Violet dye easily diffuses into cells where it is cleaved by intracellular esterases to yield a highly fluorescent compound, which then covalently binds to intracellular amines, resulting in stable, well-retained fluorescent staining that can be fixed with aldehyde fixatives. Excess unconjugated reagent passively diffuses to the extracellular medium, where it can be quenched with complete media and washed away.

Labeled T cells were then seeded at a density of about 50,000 cells/well in the coated 96-well plates, in the presence of 6.6 nM of anti-CD28 antibody for co-stimulation for about 3 days. The cells were then fixed for FACS analysis of the fluorescent signals.

Figure 8:
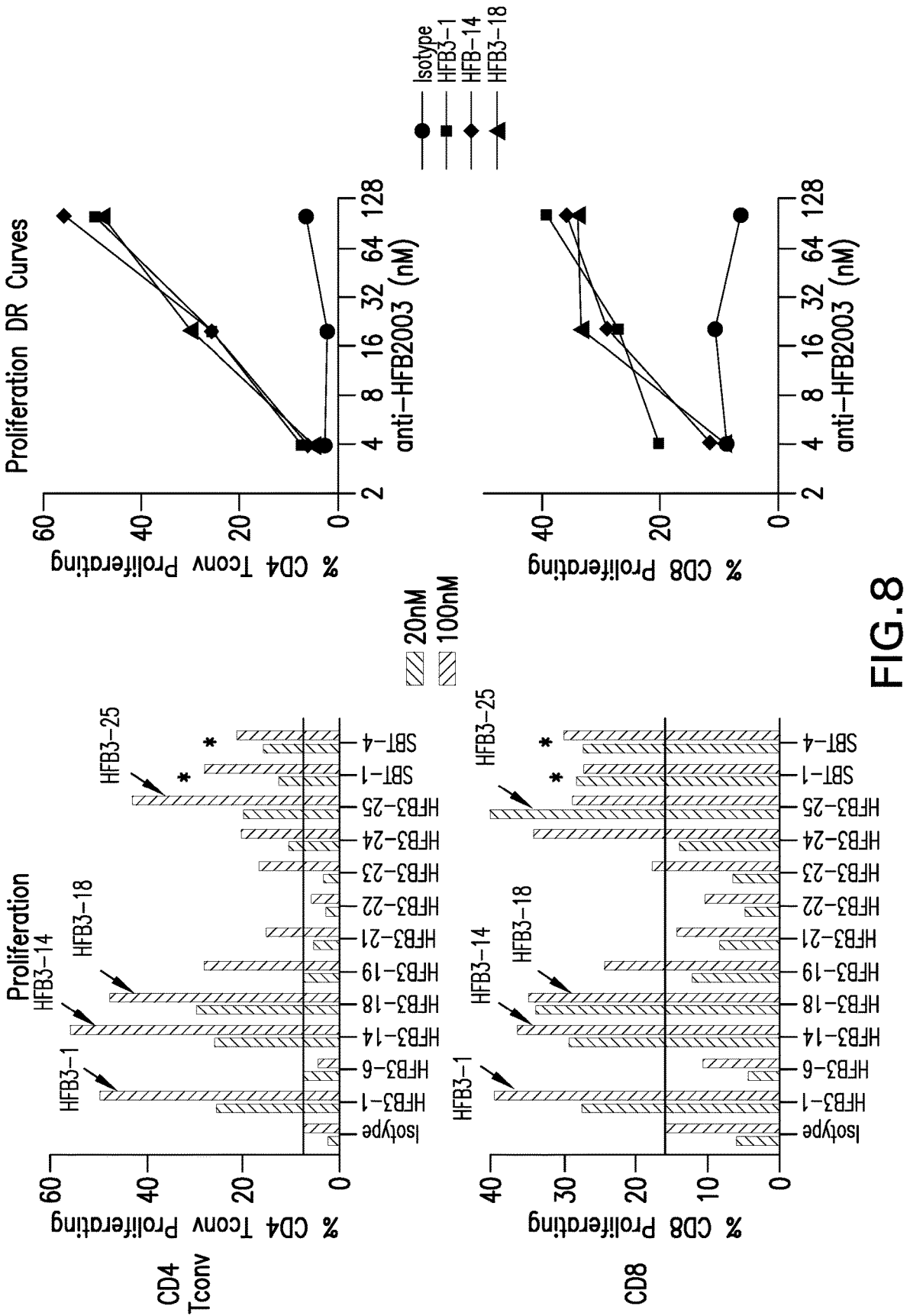
FIG. 8 shows that the co-stimulation by certain subject monoclonal antibodies, including HFB3-1, -14, -18 and -25, and CD3/CD28 led to proliferation of CD8 and CD4 Tconv in a dose-dependent manner.

The data in FIG. 8 shows that certain of the subject anti-TNFR2 antibodies co-stimulated CD8 and CD4 Tconv proliferation, even at the lower 20 nM concentration. The benchmark positive control antibodies SBT-1 and -4 also co-stimulated T cell proliferation under the same conditions, but did so to a lesser extent that the HFB3-1, -14, -18, and -25.

Additional experiment showed that such co-stimulation of primary T cell proliferation may depend on FcγR crosslinking for certain monoclonal antibodies such as HFB3-18, while there is no discernible crosslinking dependency for other antibodies such as HFB3-1 and -14.

Specifically, CD8 and CD4 Tconv were isolated from donor KP59095, and the isolated primary T cells were stimulated by CD3/CD28 TCR activation, as well as the subject anti-TNFR2 monoclonal antibodies HFB3-1, -14, or -18, in the presence of absence of 25 ng/mL recombinant human TNFα (rhTNFα). The anti-TNFR2 antibodies were either plate bound, or were supplied as soluble antibody present in the binding mixture.

Figure 19:
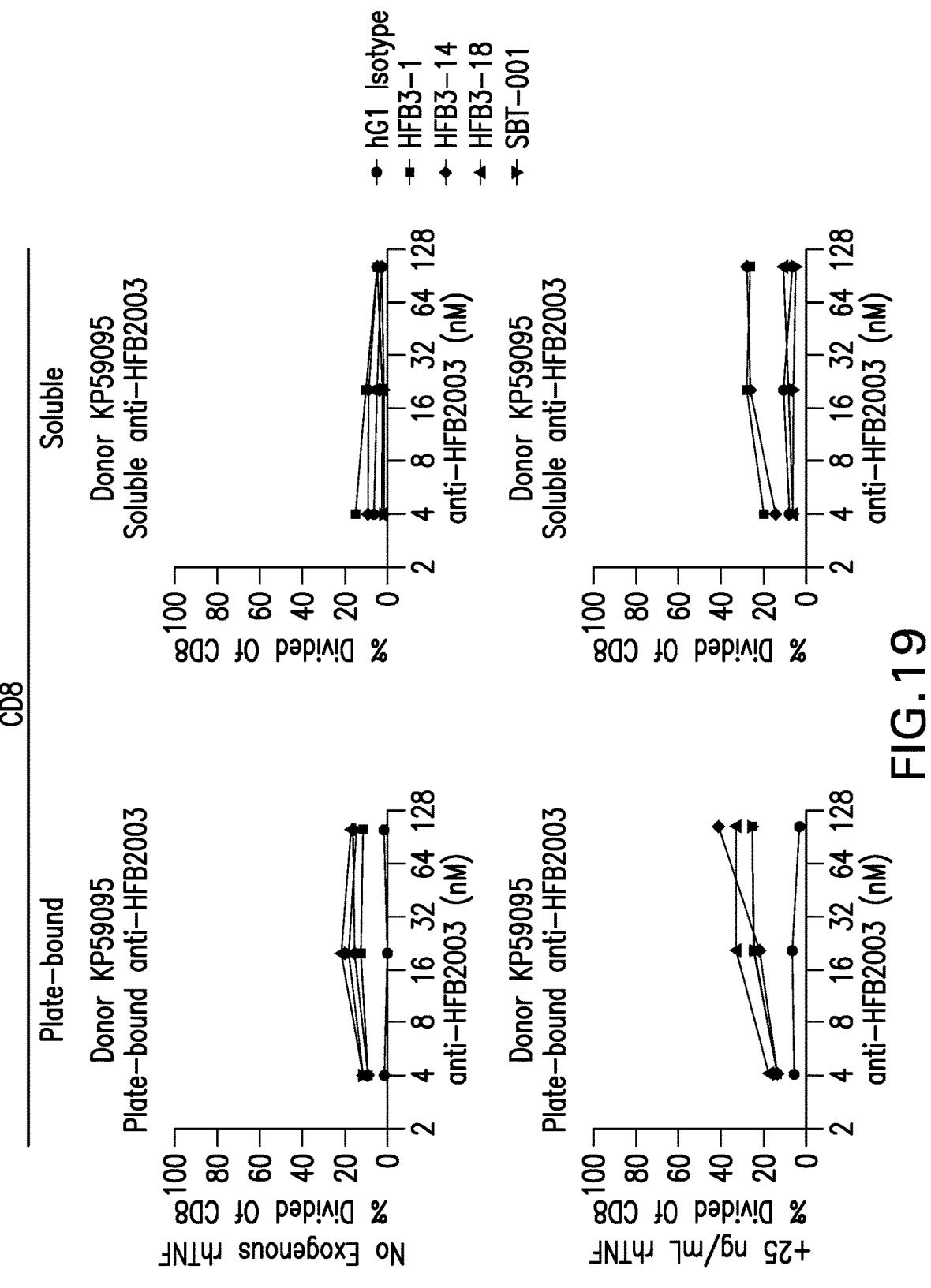
FIG. 19 shows FcγR crosslinking dependency for anti-TNFR2 monoclonal antibody HFB3-18 (but not HFB3-1 and -14) on co-stimulating primary T cells.

In the presence of 25 ng/mL rhTNFα, all three plate-bound anti-TNFR2 antibodies (HFB3-1, -14 and -18) stimulated CD8 T cell proliferation (see FIG. 19, lower left corner panel). However, only soluble HFB3-1 and HFB3-14 (but not soluble HFB3-18) were able to stimulate CD8 T cell proliferation (FIG. 19, lower right corner panel), suggesting that FcγR crosslinking may be required for HFB3-18-mediated CD8 T cell proliferation, but may not be required (i.e., crosslinking independent) for HFB3-1 and HFB3-14-mediated CD8 T cell proliferation.

Similar results were also obtained for CD4 Tconv proliferation under similar conditions (data not shown).

Example 6 Anti-TNFR2 Monoclonal Antibodies Favors Cell Proliferation on Teff Cell End (CD8 and CD4 Tconv) in the Presence of Tregs This experiment demonstrates that the subject anti-TNFR2 monoclonal antibodies can co-stimulate Teff cell (CD8 and CD4 Tconv) proliferation with CD3/CD28-mediated TCR activation, in the presence of Tregs.

Briefly, CD3$^+$ T cells, including CD8 and CD4 Tconv effector T cells, as well as Tregs, were isolated from human PBMC, and were co-stimulated by CD3/CD28-mediated TCR activation and the subject anti-TNFR2 monoclonal antibody, substantially as described above, for about 4 days. Proliferation of total CD4+ T cells and CD8$^+$ T cells, in the presence of the Tregs, were determined using the CELL-TRACE™ Violet Cell Proliferation Kit from Invitrogen (CTV). Activation of CD4$^+$ T cells CD8$^+$ T cells was also determined by measuring the percentage of CD25$^+$ T cells in the respective T cell populations.

Figure 9:
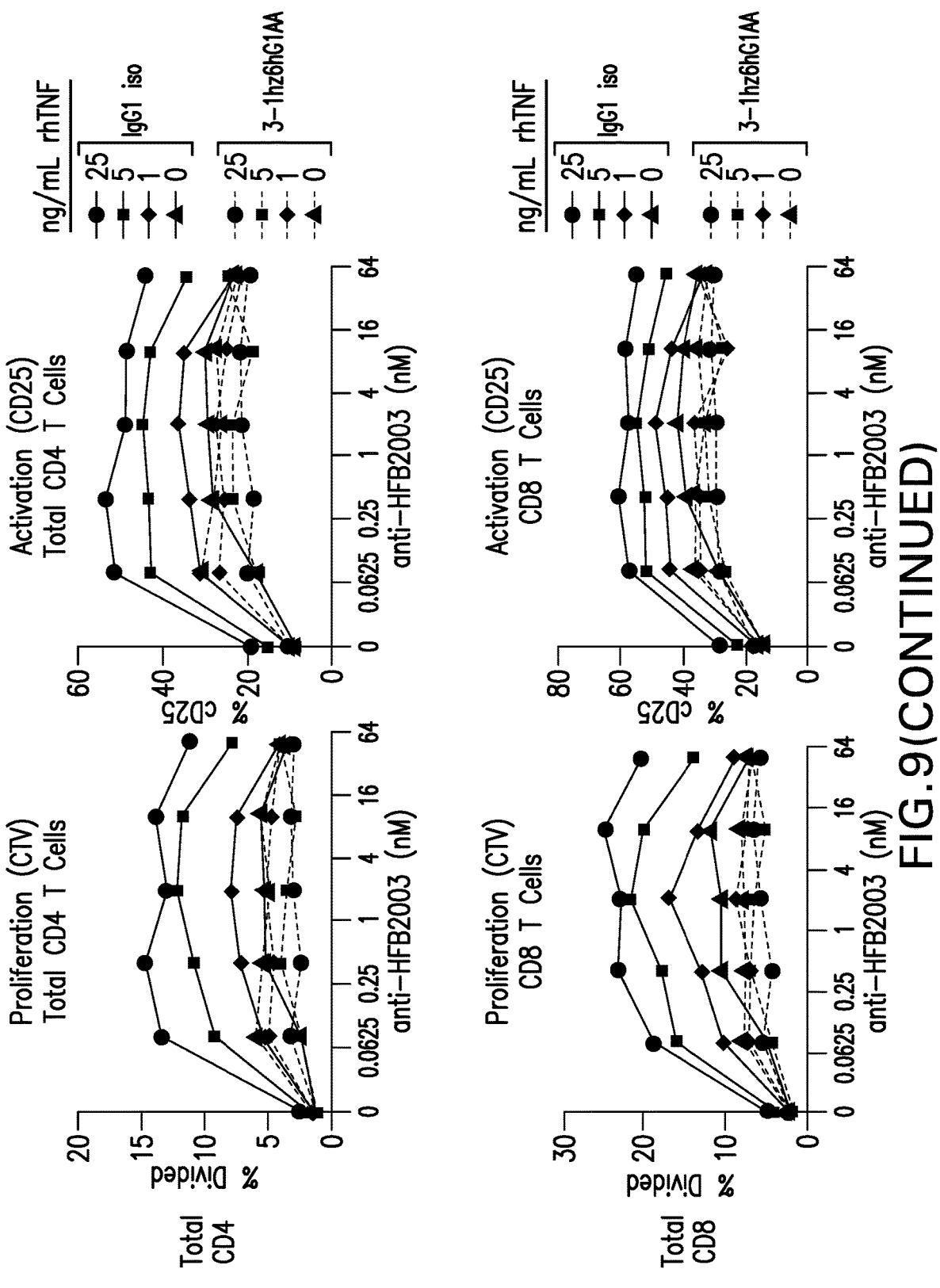
FIG. 9 shows that the anti-TNFR2 monoclonal antibody of the invention (e.g., HFB3-1hz6-hG1AA, a humanized version of HFB3-1) dose-dependently favored cell proliferation on effector T cells (CD8 and CD4 Tconv) in the presence of Tregs.

The results in FIG. 9 showed that the anti-TNFR2 monoclonal antibody of the invention (e.g., HFB3-1hz6-hG1AA, a humanized version of HFB3-1, see below) favored cell proliferation on effector T cells (CD8 and CD4 Tconv) even in the presence of Tregs.

Example 7 Anti-TNFR2 Monoclonal Antibodies had Negligible ADCC Effect on HH Lymphoma Cells This experiment demonstrates that the subject anti-TNFR2 monoclonal antibodies have negligible ADCC effect on T cell lymphoma, suggesting such antibodies are suitable for use as T cell co-stimulatory agents.

The antibody-dependent cellular cytotoxicity (ADCC) is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. ADCC requires an effector cell which classically is known to be natural killer (NK) cells that typically interact with IgG antibodies.

In this experiment, Jurkat.CD16V/NFAT/luc cells were used as effector cells, while HH lymphoma cells were target cells. The effector to target cell ratio was about 6:1. Co-cultured effector and target cells were incubated overnight in the presence of a subject anti-TNFR2 monoclonal antibody (e.g., HFB3-1, -14, or -18), or an isotype matched control (hIgG1), at a concentration of 0, 0.0066, 0.66, or 66 nM. The moganulizumab antibody was used as a positive control for ADCC.

Figure 10:
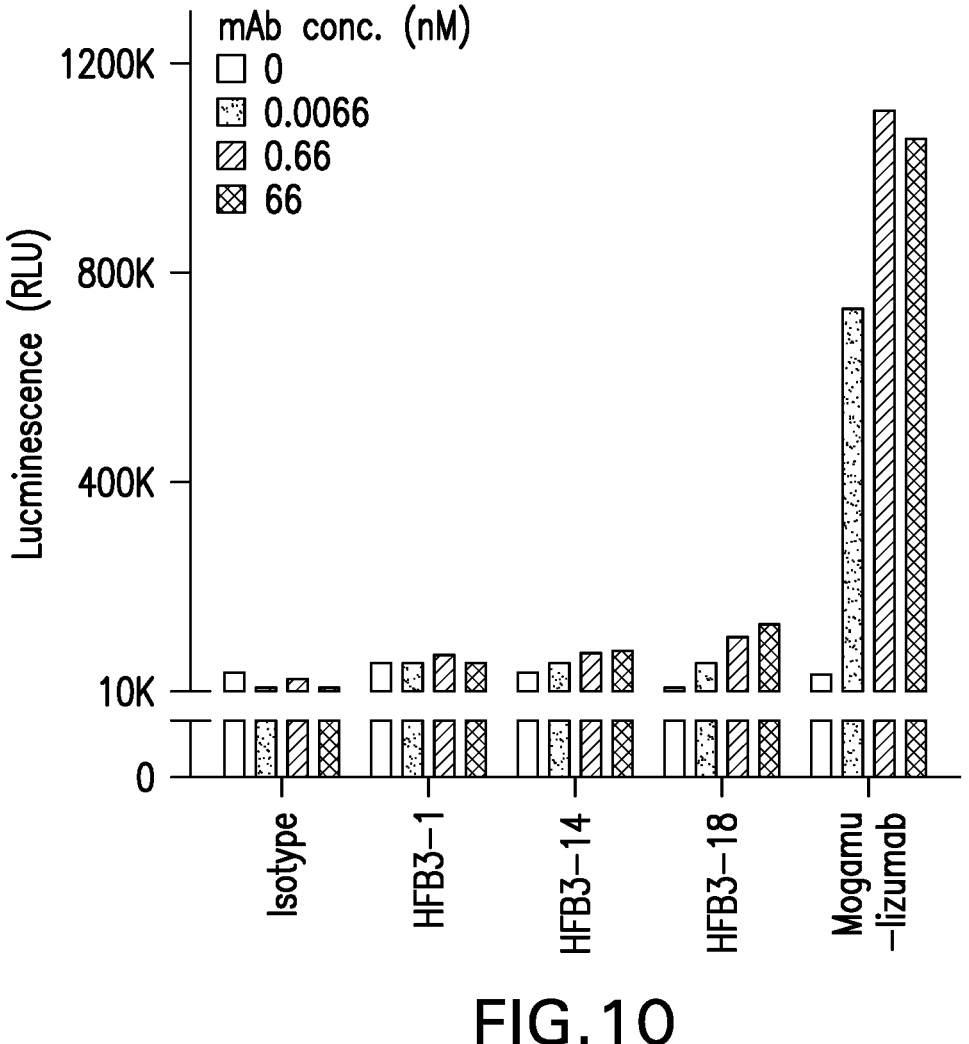
FIG. 10 shows the lack of ADCC effect for the subject anti-TNFR2 antibodies.

The results in FIG. 10 showed that the positive control antibody moganulizumab had at least 120-fold stronger ADCC effect on the target cells than any of the tested anti-TNFR2 monoclonal antibodies. The data demonstrated that the subject anti-TNFR2 antibodies are suitable for use as T cell co-stimulatory agents due to their low/absent ADCC effect on T cells.

Example 8 Binding of Humanized Anti-TNFR2
Monoclonal Antibodies to TNFR2

Multiple humanized monoclonal antibodies for HFB3-1, -14 and -18 were generated, including at least 20 for HFB3-1, 16 for HFB3-14, and one for HFB3-18 (due to the selected human germline being highly similar to the parental HFB3-18 monoclonal antibody coding sequence). The abilities of these humanized monoclonal antibodies to bind human TNFR2 expressed on CHO cells were determined substantially as described in Example 1.

Figure 12A:
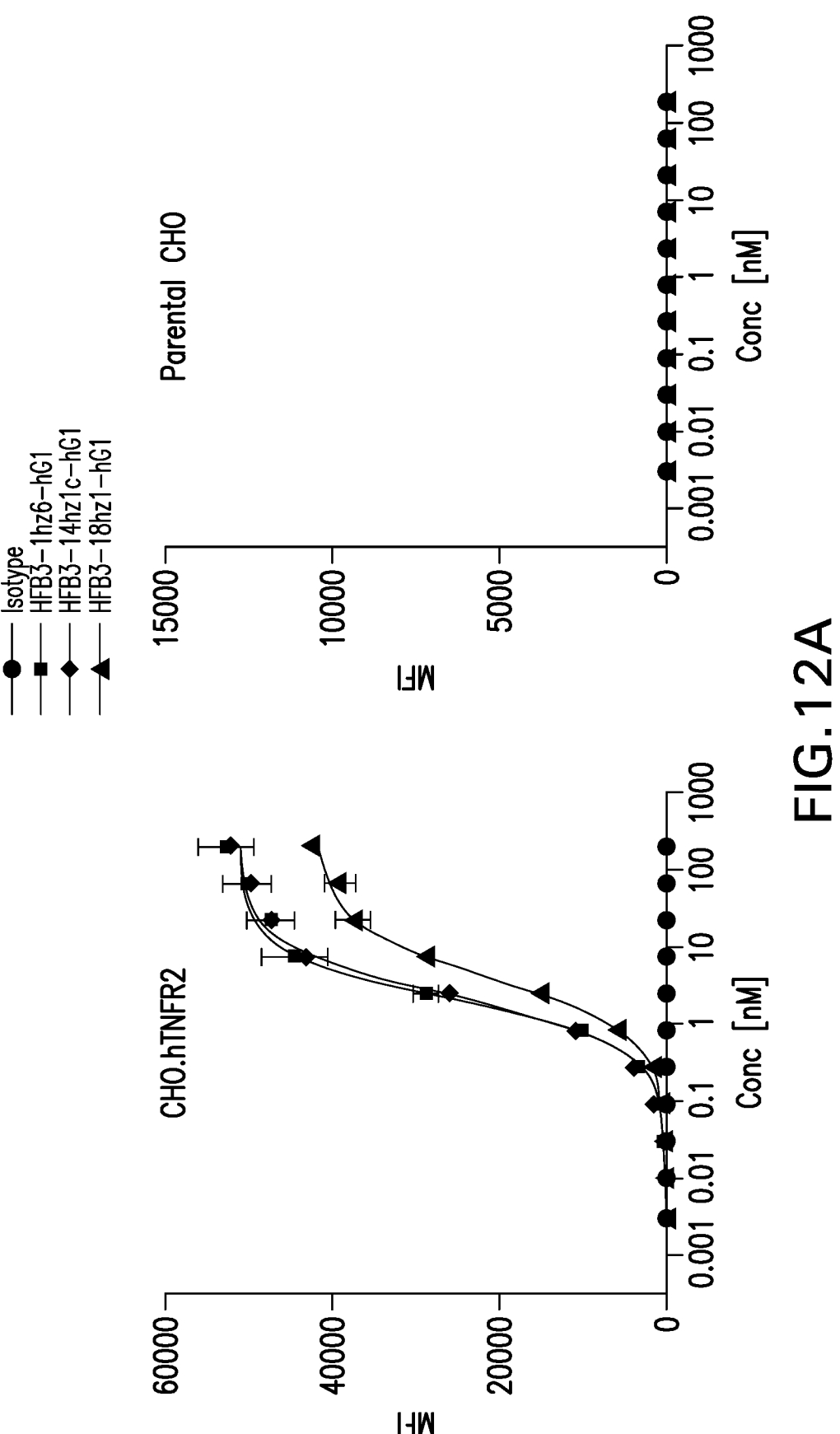
FIG. 12A shows binding of humanized variants of the chimeric monoclonal antibodies HFB3-1, -14 and -18 to CHO cells expressing human TNFR2 (CHO.hTNFR2) but not to parental CHO cells.
Figure 12B:
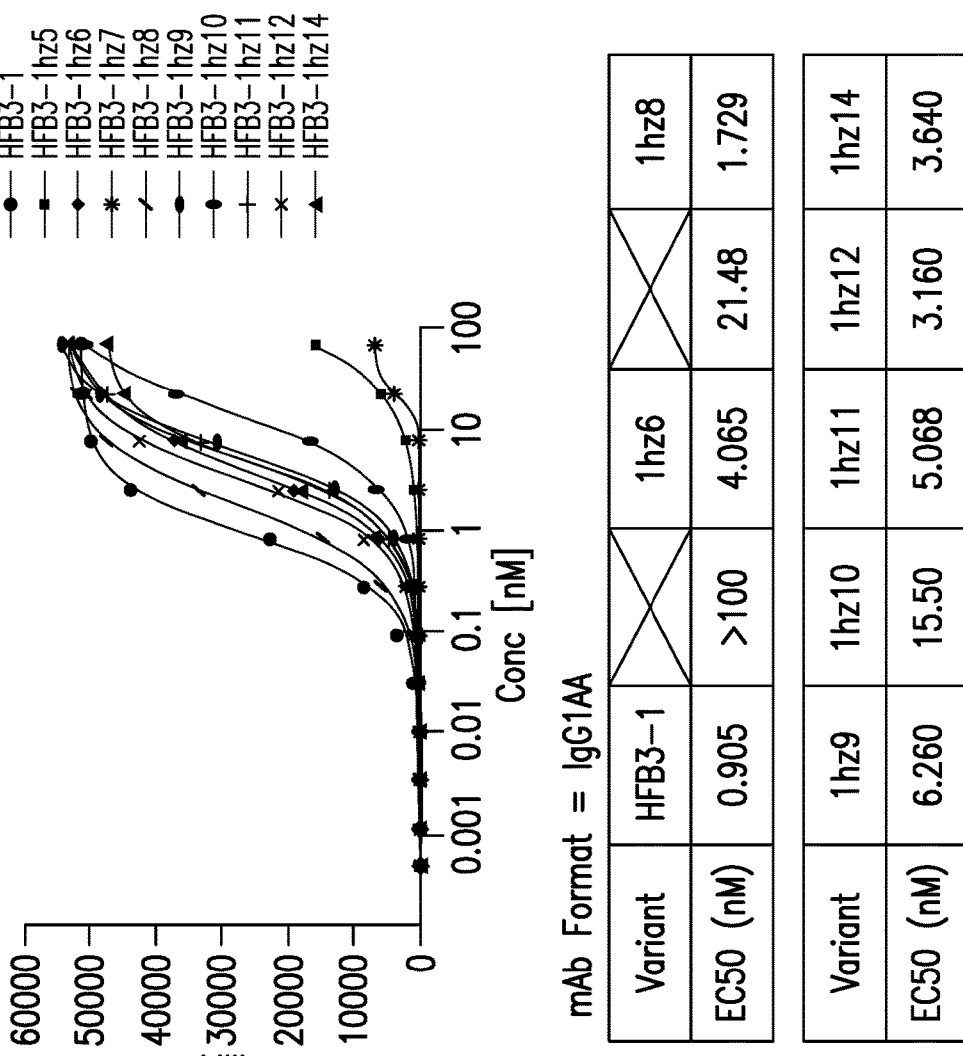
FIG. 12B shows binding affinity of selected humanized anti-TNFR2 monoclonal antibodies. $EC_{50}$ values for the test humanized antibodies and the parental chimeric antibodies were measured against CHO cells expressing human TNFR2 (CHO.hHFB3).
Figure 12B:
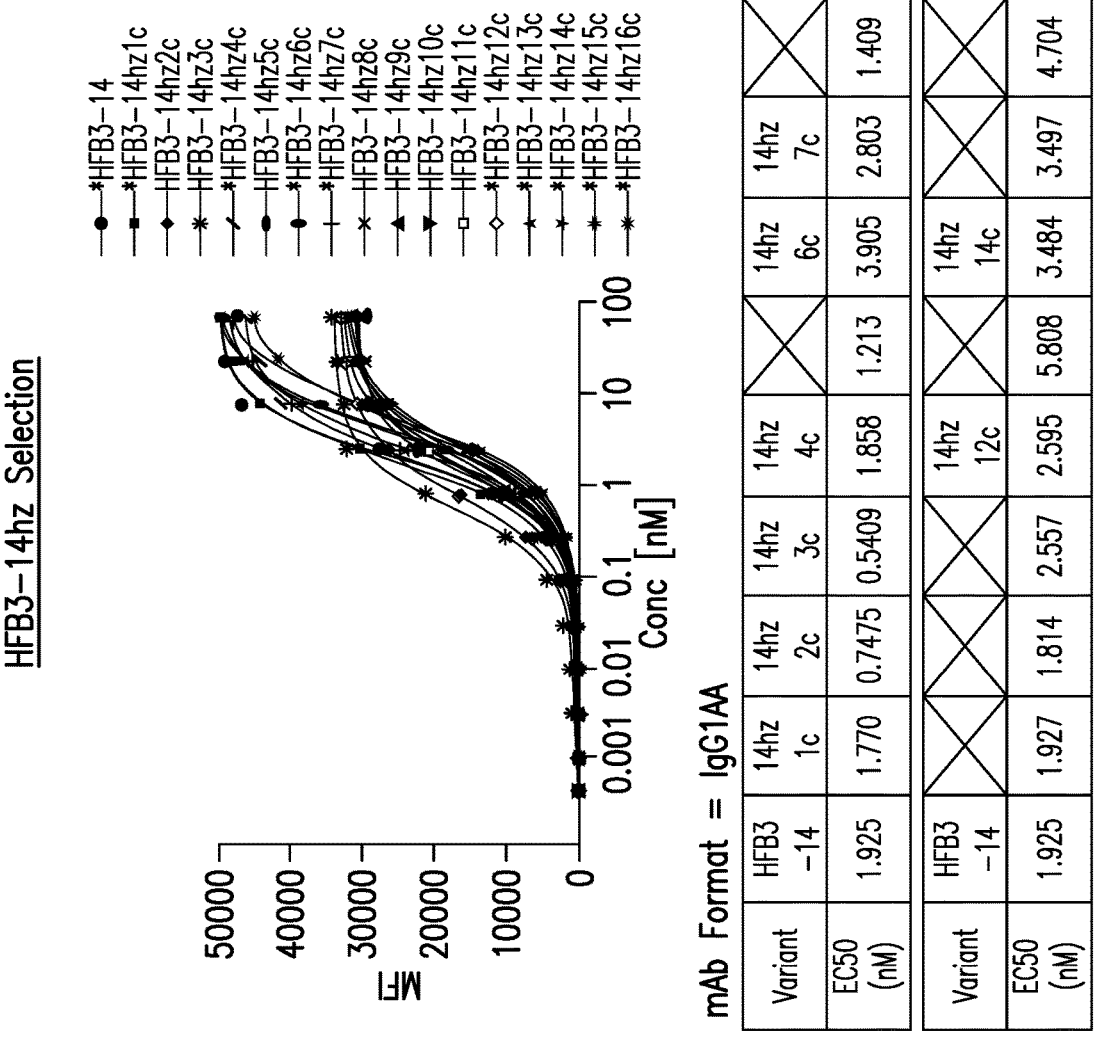

FIG. 12A shows that the humanized HFB3-1hz6, HFB3-14hz1c and HFB3-18hz1 bound to CHO cells expression human TNFR2 (CHO.hTNFR) but did not bind to the parental CHO cells. FIG. 12B shows that at least 7 humanized HFB3-1 antibodies, namely HFB3-1hz6, -1hz8, -1hz9, -1hz10, -1hz11, -1hz12, and -1hz14, and at least 8 humanized HFB3-14 antibodies, namely HFB3-14hz1c, -14hz2c, -14hz3c, -14hz4c, -14hz6c, -14hz7c, -14hz12c, and -14hz14c, retained roughly the same (if not better) level of binding affinity by the respective parental chimeric antibodies towards CHO cell-expressed TNFR2 (CHO.hHFB3).

Figure 13:
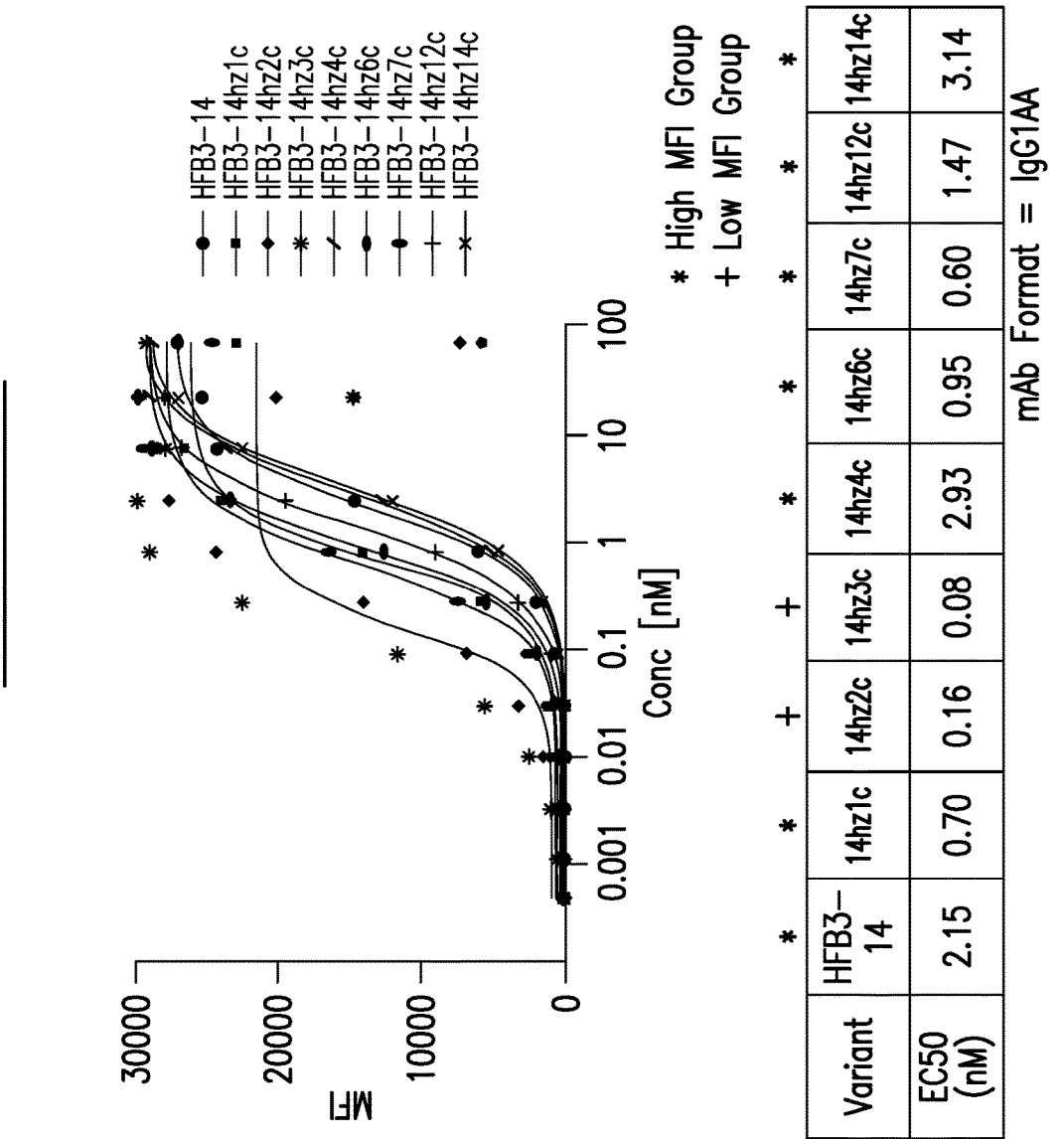
FIG. 13 shows binding affinity of selected humanized anti-TNFR2 monoclonal antibodies. $EC_{50}$ values for the test humanized antibodies and the parental chimeric antibodies were measured against CHO cells expressing rhesus monkey TNFR2 (CHO.mkHFB3).

Similar experiments were repeated using instead CHO cells expressing rhesus monkey ortholog of TNFR2 (CHO.mkHFB3). FIG. 13 shows that the general trend of binding towards CHO cells expressing monkey TNFR2 matched that for CHO.hTNFR2. However, somewhat unstable binding was observed for two of the humanized variants based on HFB3-14, namely HFB3-14hz2c and -14hz3c.

Figure 14A:
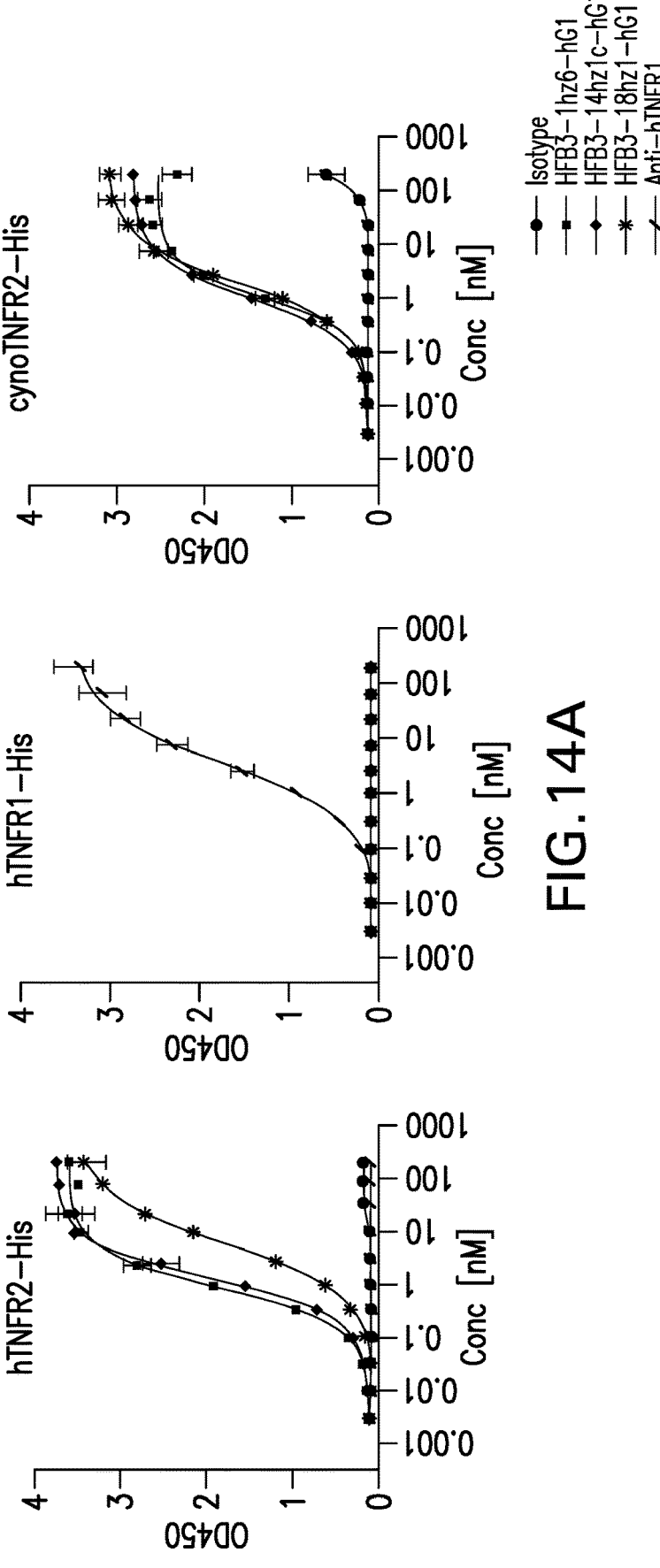
FIG. 14A shows binding of humanized anti-TNFR2 antibodies to recombinant human and cynomolgus TNFR2 but not to recombinant human TNFR1 in ELISA assay.

Binding of the humanized anti-TNFR2 antibodies is specific for TNFR2 and not to TNFR1. The ELISA assay in FIG. 14A demonstrated that humanized monoclonal antibodies HFB3-1hz6, HFB3-14hz1c and HFB3-18hz1 bound to recombinant human and cynomolgus TNFR2 (hTNFR2-His and cynoTNFR2-His, respectively) without recognizing recombinant human TNFR1 (hTNFR1-His). Additionally, binding EC50 of these humanized anti-TNFR2 antibodies to recombinant human and cynomolgus TNFR2 ranged from a sub- to single digit-nM.

Binding affinity for the humanized variants towards human TNFR2 was also verified using recombinant human TNFR2 protein and AHC biosensor. Anti-Human IgG Fc Capture (AHC) biosensors enable kinetic characterization of macromolecular interactions between human Fc-containing proteins (e.g., the subject antibodies) and target analytes (e.g., recombinant human TNFR2). Immobilization of human Fc-containing proteins is achieved through a factory immobilized anti-human Fc-specific antibody whose high-affinity for the human Fc domain provides the stable baseline required for demanding kinetics applications. In this specific experiment, the test antibodies (humanized vs. the parental chimeric antibody) were loaded at a concentration of 20 µg/mL in assay buffer (PBS, pH 7.4, 0.1% BSA, 0.1% Tween20). The analyte was His-tagged recombinant human TNFR2 at 500, 167, or 55.7 nM. The capture assay was run at 25° C.

As shown in FIG. 14B, there was no major difference to distinguish the humanized variants from their respective chimeric parental antibodies in terms of affinity towards recombinant human TNFR2.

Example 3 shows that the chimeric anti-TNFR2 antibodies bind to TCR-activated T cells. Substantially the same experiment was run for the humanized variants, and the results were shown in FIG. 15.

Specifically, in terms of binding to TCR-activated CD8 cells, most humanized HFB3-1 antibodies exhibited sub nM level affinity, except for two variants (HFB3-1hz5 and -1hz7) that did not appear to bind TCR-activated CD8 cells. Meanwhile, all humanized HFB3-14 variants exhibited single digit nM affinity towards TCR-activated CD8 T cells. There is no major difference to distinguish different variants. Of note, the positive control antibodies SBT-2 and -3 were not good binders to primary CD8 cells.

Example 9 Co-Stimulatory Effect of Humanized
Anti-TNFR2 Monoclonal Antibodies to Proliferate
TCR-Activated CD4 and CD8 T Cells Example 5 showed that co-stimulatory effect of chimeric anti-TNFR2 monoclonal antibodies proliferates isolated human primary CD8 and CD4 Tconv cells. This experiment demonstrates the same in TCR-activated CD4 T cells using the humanized variants of HFB3-1 and HFB3-14.

Figure 16:
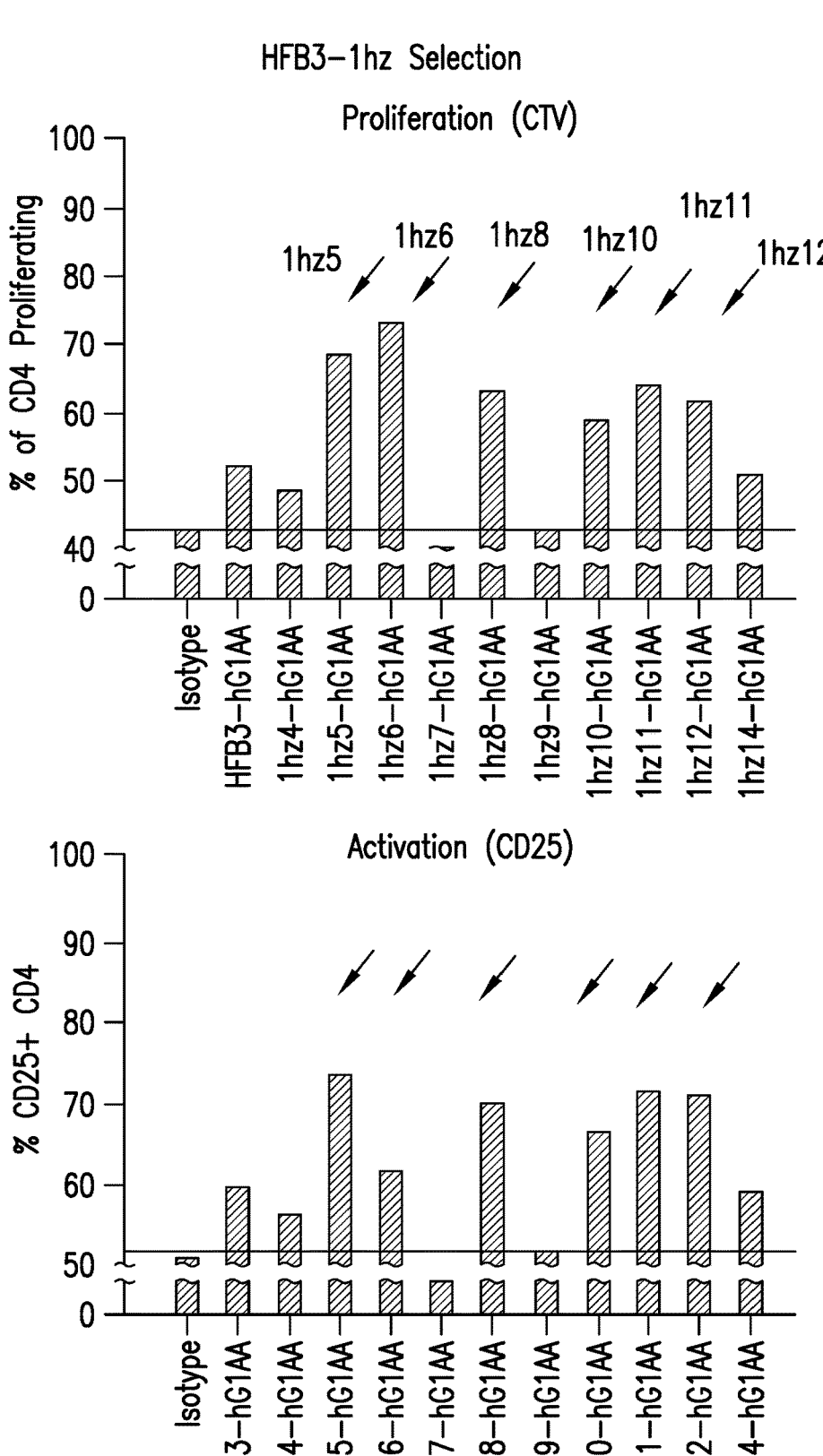
FIG. 16 shows co-stimulatory effect of humanized anti-TNFR2 monoclonal antibodies to proliferate TCR-activated CD4 T cells.
Figure 16:
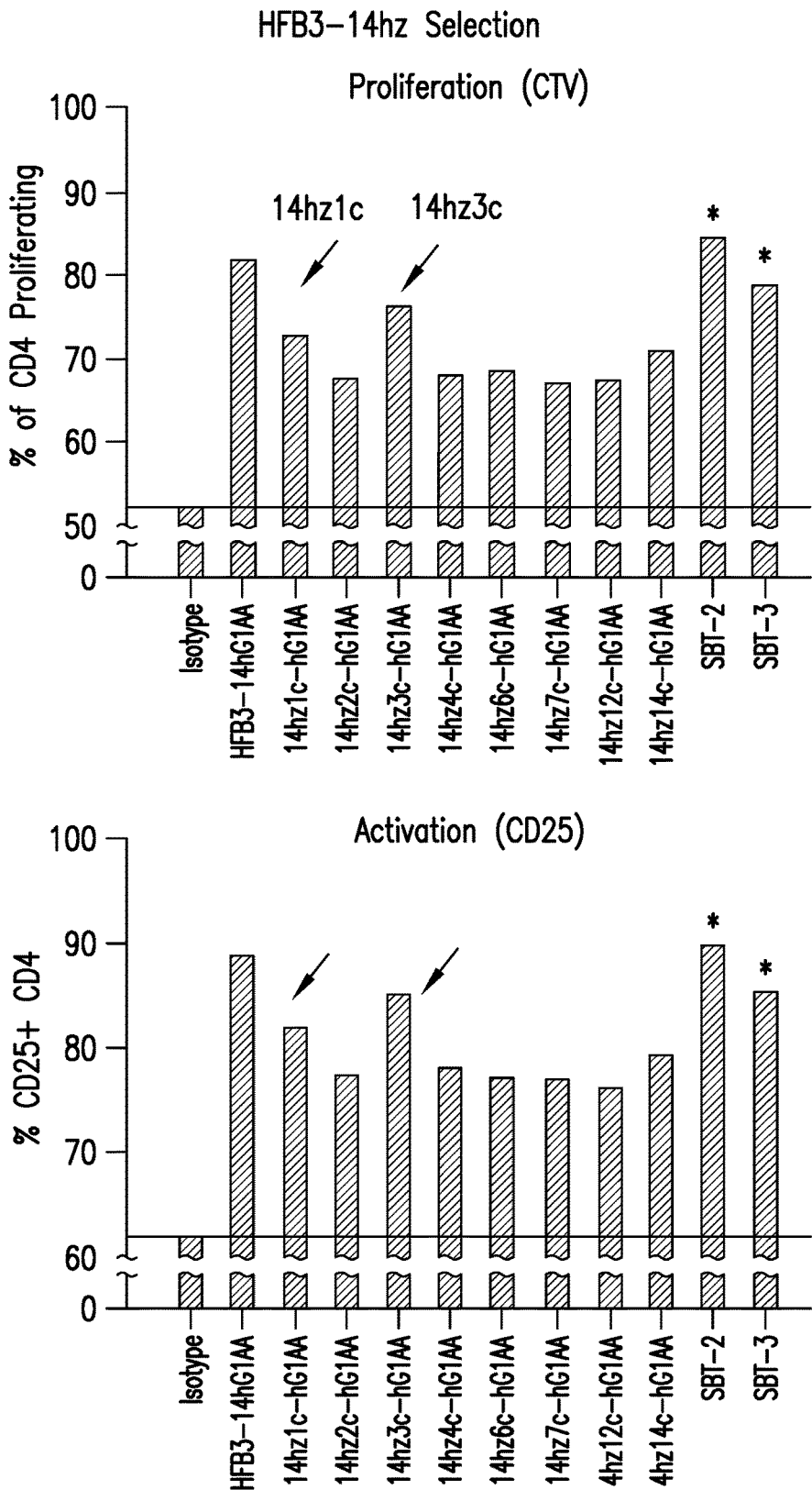

Specifically, FIG. 16 shows that humanized variants HFB3-1hz5, -1hz6, -1hz8, -1hz10, -1hz11, and -1hz12 strongly stimulated TCR-activated CD4 T cells based on the CTV proliferation assay (see above), each to a larger extent compared to the parental HFB3-1 chimeric antibody. The same was repeated for the HFB3-14hz1c and -14hz3c variants.

Likewise, T cell activation based on the percentage of CD25⁺ T cell populations was also confirmed for the above variants.

Figure 20:
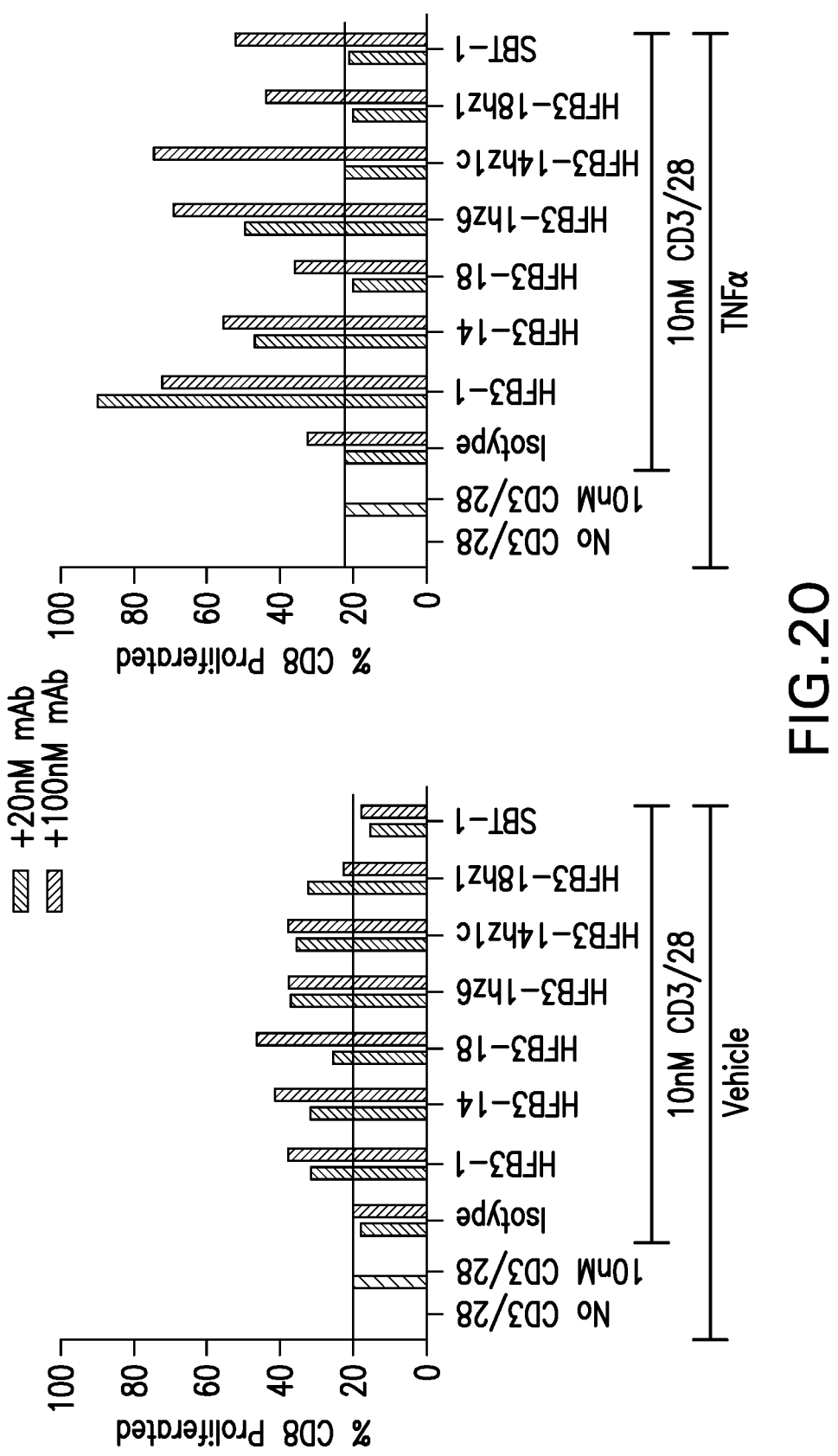
FIG. 20 shows confirmatory co-stimulation effect of selected humanized anti-TNFR2 antibodies to proliferate CD8 T cells, either in the presence or absence of TNFα.

Confirmatory co-stimulatory data for HFB3-1hz6-hG1, -14hz1c-hG1 and -18hz1-hG1 were also obtained to show that these variants had co-stimulatory effect to proliferate TCR-activated CD8 T cells (activated by CD3/CD28 stimulation). Specifically, both the parental chimeric antibodies and selected humanized variants enhanced CD8 T cell proliferation stimulated by CD3/CD28 TCR activation. Further, cooperation of TNFα (right panel) further enhanced anti-TNFR2 antibody-mediated CD8 proliferation. See FIG. 20.

Example 10 Certain Humanized Anti-TNFR2
Monoclonal Antibodies Induced NFκB Signaling in
Tregs Example 4 showed that binding of certain chimeric anti-TNFR2 monoclonal antibodies to primary CD8 and CD4 Tconv cells co-stimulated NFκB signaling. Similar experiment here demonstrates that certain humanized variant anti-TNFR2 antibodies induced NFκB signaling in Tregs.

Figure 17:
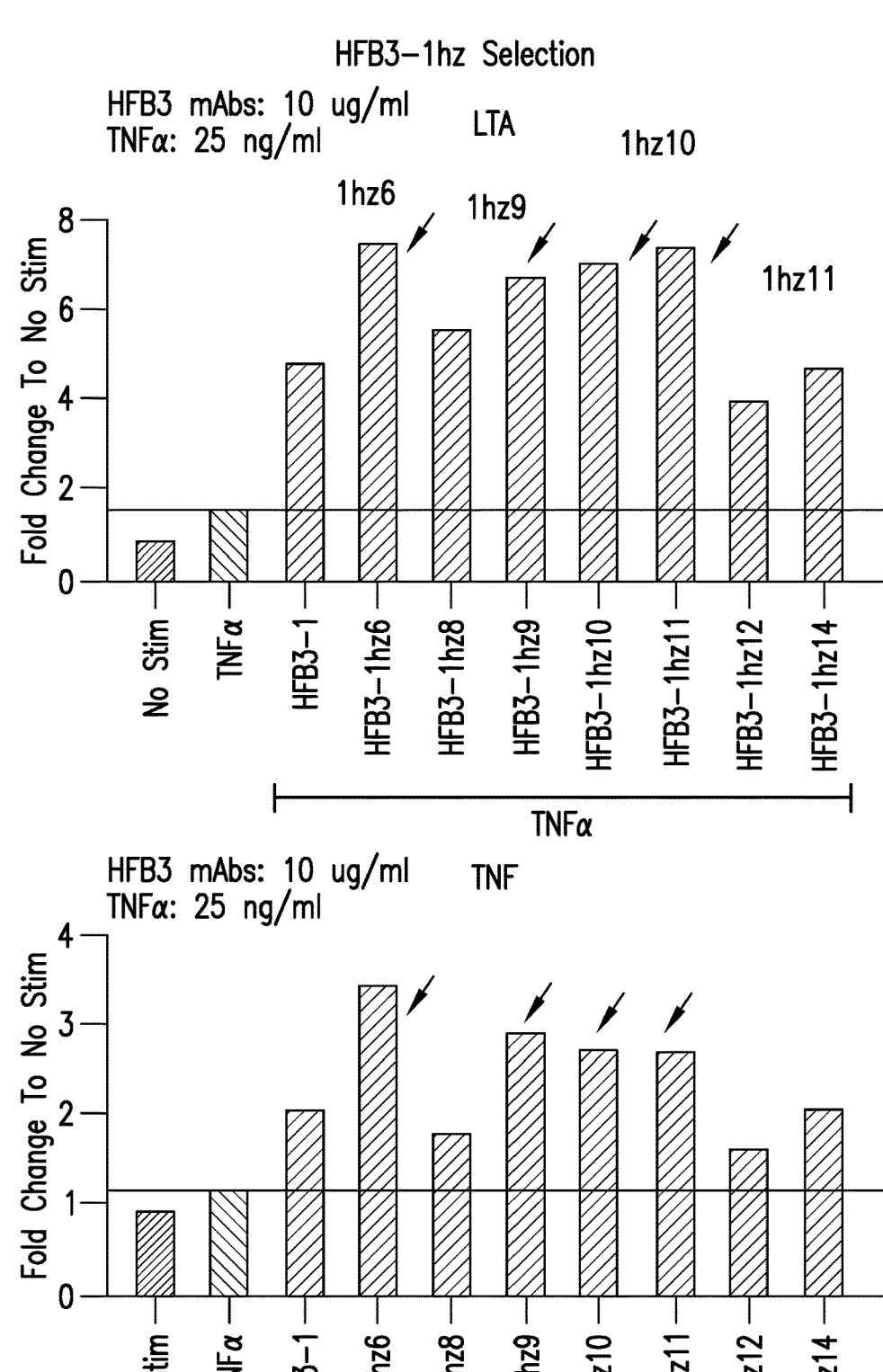
FIG. 17 shows that co-stimulation of Tregs using certain humanized variant anti-TNFR2 antibodies and TNFα led to NFκB downstream signaling.
Figure 17:
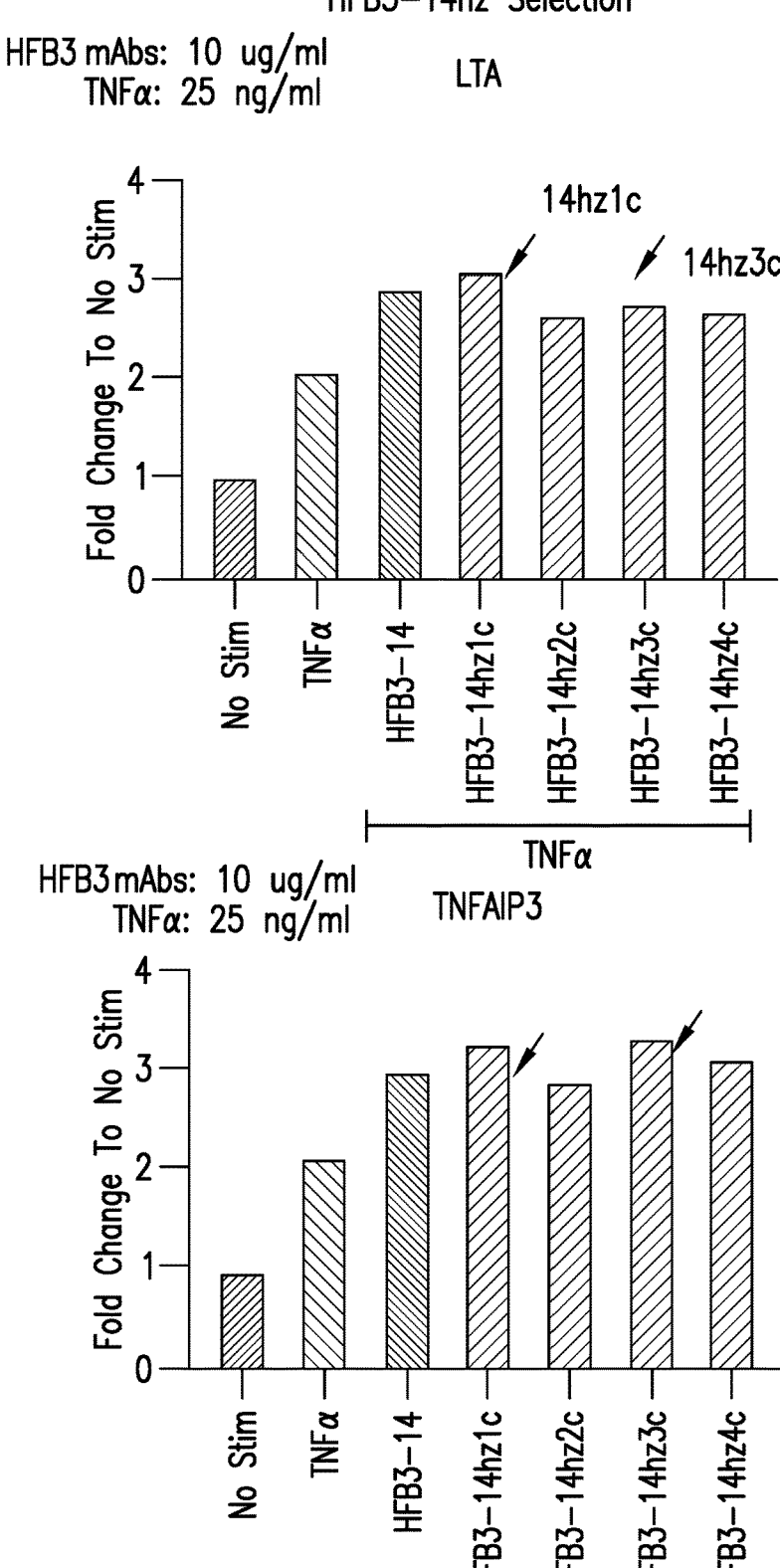

Specifically, FIG. 17 shows that co-stimulation of Tregs using certain humanized variant anti-TNFR2 antibodies and TNFα led to NFκB downstream signaling in LTA, TNF, and TNF AIP3. Variants HFB3-1hz6, -1hz9, -1hz10, and -1hz11 promoted NFκB signaling to a larger extent than the parental chimeric antibody HFB3-1. Meanwhile, variants HFB3-14hz1c, -14hz2c, -14hz3c, and -14hz4c (particularly HFB3-14 hz1c and -14hz3c) also promoted NFκB signaling to a larger extent than the parental chimeric antibody HFB3-14.

Example 11 Anti-TNFR2 Antibodies are Stable

In order to confirm that the subject humanized anti-TNFR2 antibodies are stable in storage, thus suitable for further development as a therapeutic agent, a variety of developability assays were run for selected humanized antibodies.

In the first experiment, selected subject humanized antibodies were stored at 25 or 40° C. in PBS (pH7.4), and the stability of the various antibodies were determined on Days 7 and 14. The results in FIG. 18 demonstrated that all tested antibodies, except for 1 variant HFB3-14hz4c-hG1AA, were stable at the conditions tested.

In the second experiment, the same antibodies were tested for stability under low pH conditions (100 mM AcH, pH3.5, 25° C.), for 0, 3, and 6 hours. The results in FIG. 18 again demonstrated that all tested antibodies, except for 1 variant HFB3-14hz4c-hG1AA, were stable at the conditions tested.

In the third experiment, the same antibodies were subject to 1, 2, or 3 freeze-thaw cycles. The results in FIG. 18 again demonstrated that all tested antibodies, except for 2 variants (HFB3-1hz6-hG1AA and HFB3-1hz10-hG1AA), were stable at the conditions tested.

Similar experiments were repeated for HFB3-1hz6-hG1, -14hz1c-hG1, and -18hz1-hG1. All three variants were generally stable under the three tests outlined above, except that HFB3-1hz6-hG1 and -18hz1-hG1 began to degrade after 14 days.

Collectively, the data suggests that these subject variant humanized anti-TNFR2 monoclonal antibodies have no major developability issues, and are suitable for use as therapeutic antibodies.

Example 12 Anti-TNFR2 Antibodies in Humanized TNFR2 Knock-In (KI) Mouse and their Effects on T Cells In order to better demonstrate the therapeutic efficacy of the subject anti-TNFR2 antibodies, a humanized TNFR2 knock-in (KI) mouse was generated in the C57BL/6 mouse background through commercial service (Biocytogen, Wakefield, MA).

In the first series of experiments, ex vivo binding between selected humanized anti-TNFR2 antibodies and CD3 T cells from the KI mice (TNFR2 KI CD3 T cells) were analyzed, under co-stimulation by 1 μg/mL CD28 and either 0.2 or 1 μg/mL CD3. The results showed that 1 μg/mL CD3 activated spleen cells from the KI mice better than 0.2 μg/mL CD3. Expression of human TNFR2 can be detected on KI CD3$^+$ T cells, which expression/detection can be enhanced by TNFα and under mild (0.2 μg/mL) CD3 stimulation. Furthermore, a single dose of 200 nM of each of the 6 anti-TNFR2 antibodies (i.e., HFB3-1, -14, and -18, as well as their humanized variants -1hz6, -14hz1c, and -18hz1) did not show discernible difference on TNFR2 binding, possibly due to saturation level of binding. Data not shown.

The same ex vivo binding experiments were also repeated for CD8 T cells isolated from the TNFR2 KI mouse. Here, binding of anti-TNFR2 monoclonal antibodies (chimeric and humanized versions thereof) to TNFR2 can be observed under strong CD3 (1 μg/mL) stimulation. Meanwhile, TNFα enhanced TNFR2 binding under mild CD3 (0.2 μg/mL) stimulation. Data not shown.

Next, the abilities of the subject anti-TNFR2 antibodies (chimeric and humanized) to co-stimulate downstream NFκB signaling in TNFR2 KI CD8 and CD4 Tconc cells ex vivo, in the presence of TCR activation via CD3/CD28, and in the presence of TNFα, were examined.

Figure 21:
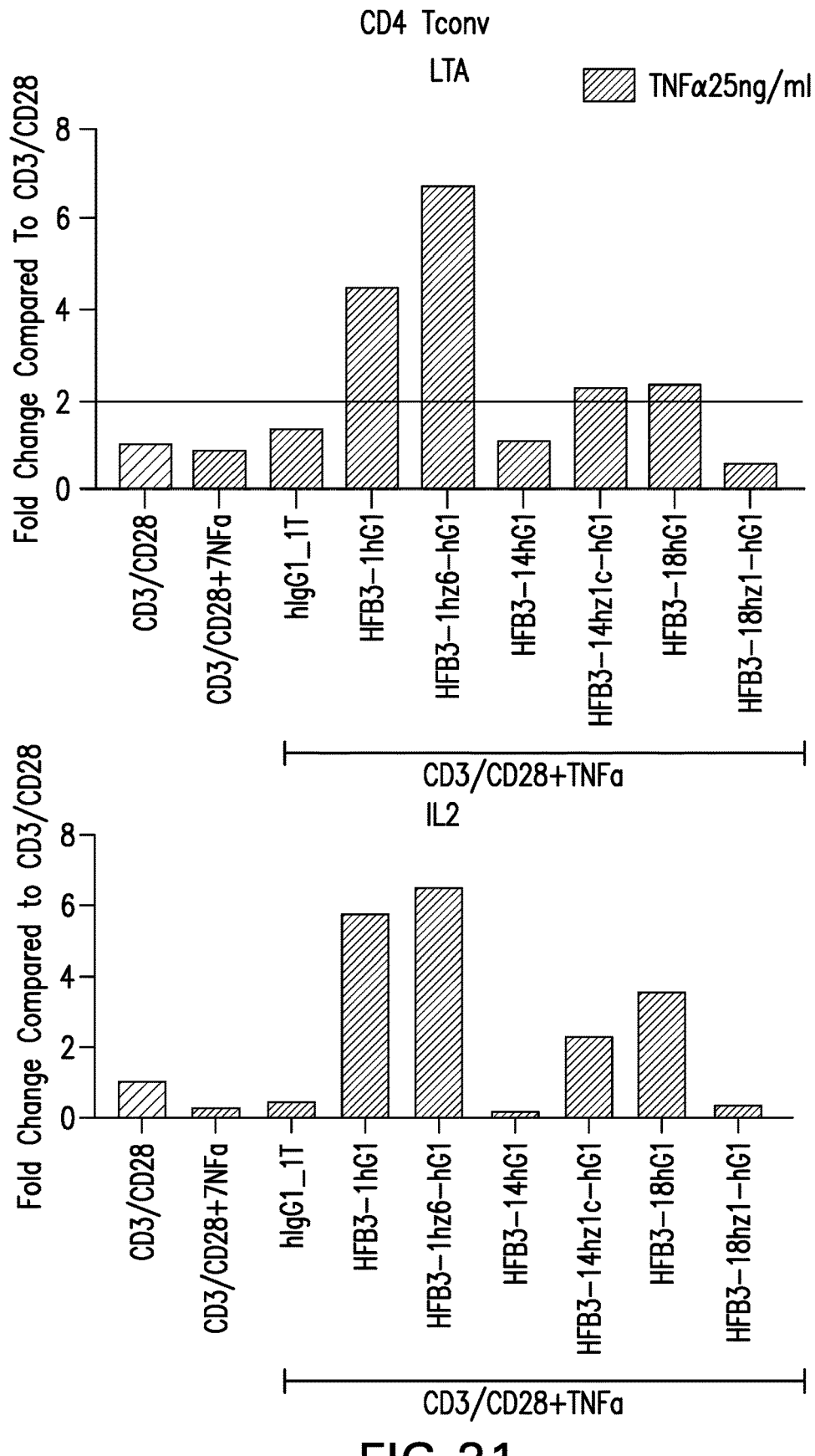
FIG. 21 shows that the subject anti-TNFR2 monoclonal antibodies co-stimulate downstream NFκB signaling ex vivo in humanized TNFR2 knock-in CD8 and CD4 Tconv cells, in the presence of CD3/CD28-mediated TCR activation and 25 ng/mL TNFα.
Figure 21:
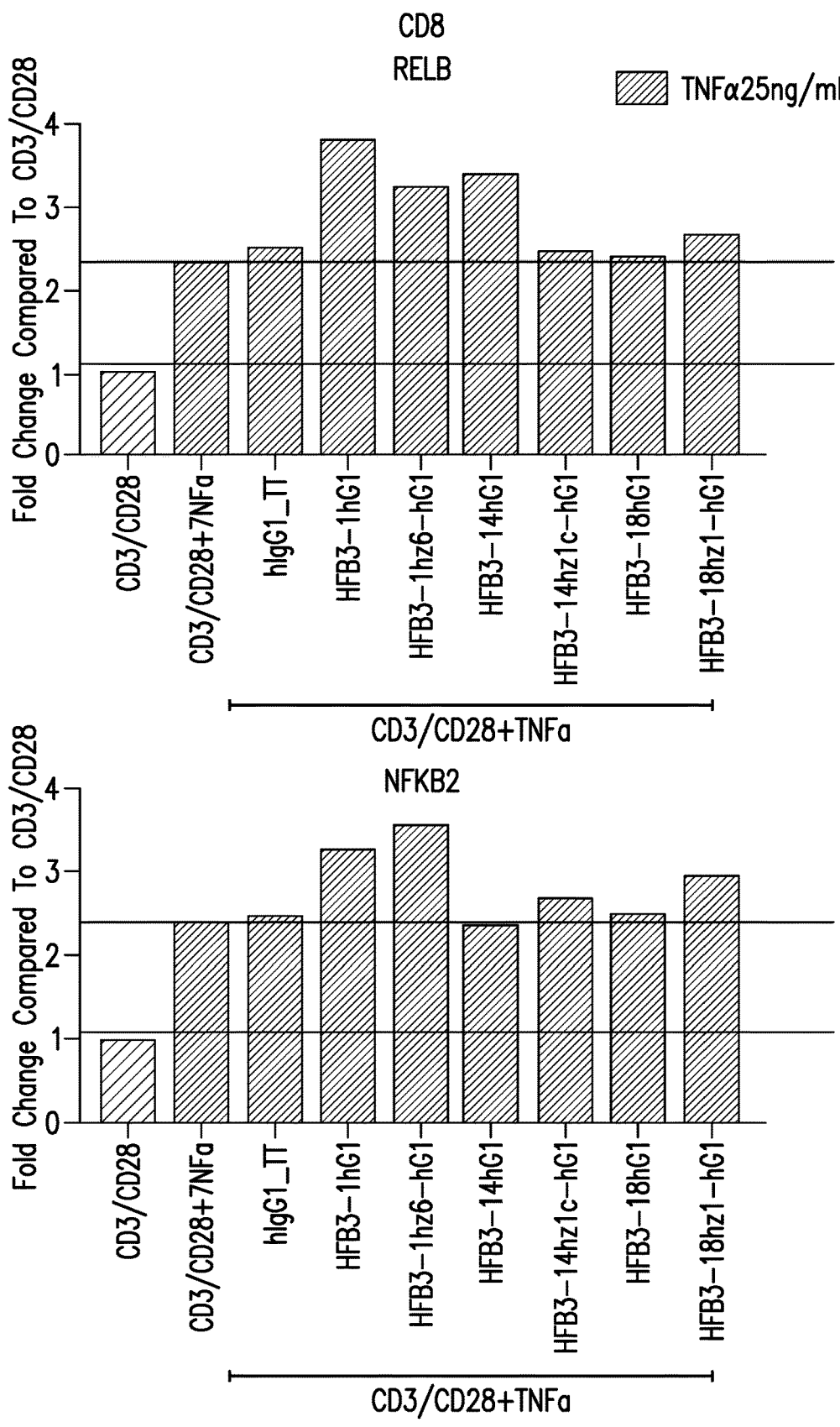
Figure 22:
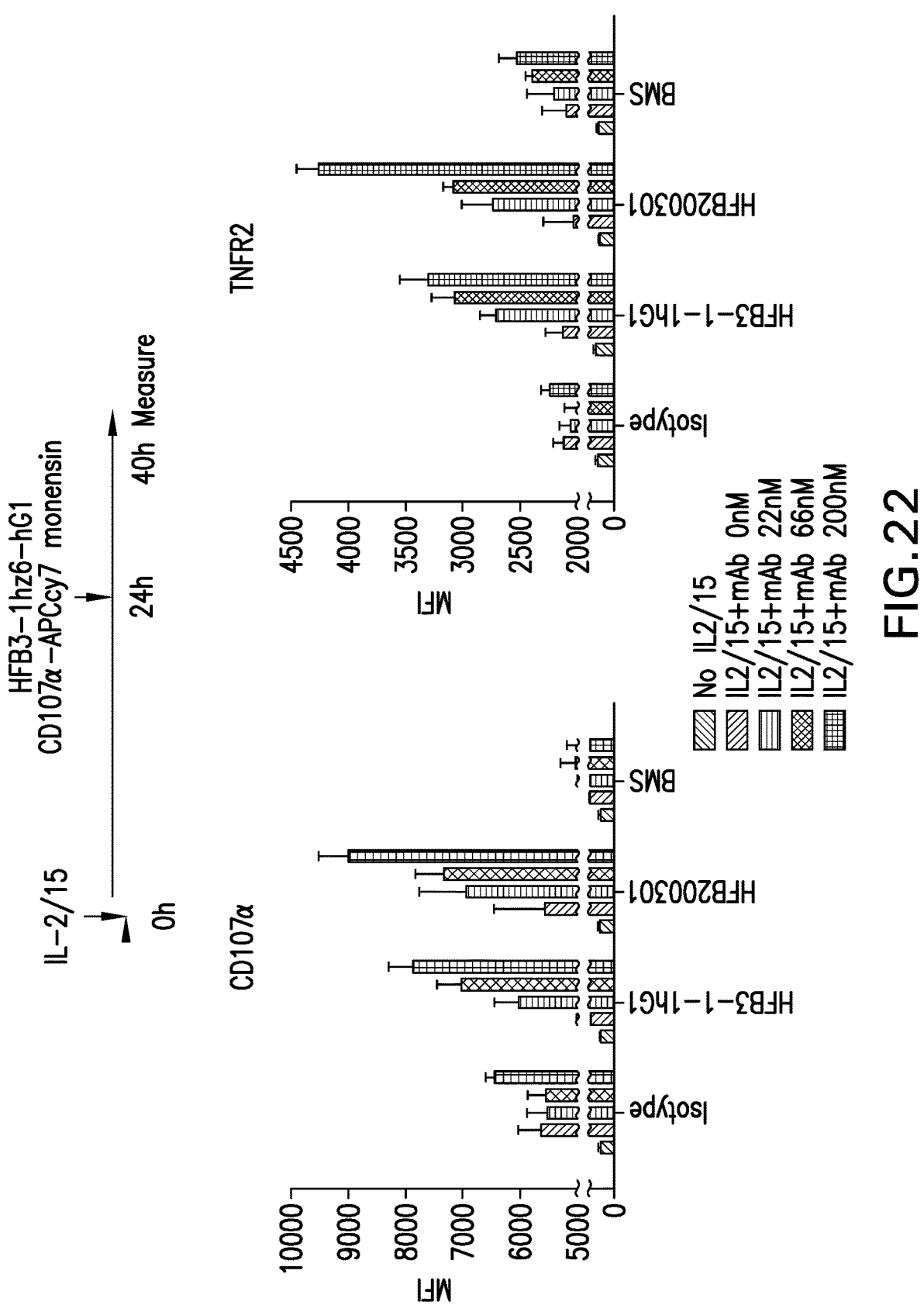
FIG. 22 shows ex vivo activation of isolated natural killer (NK) cells by humanized HFB3-1hz6-hG1 antibody and the parental HFB3-1-hG1 antibody after stimulation with soluble IL-2 (10 ng/mL) and IL-15 (10 ng/mL). Timeline of the experiment is shown in the top panel. CD107a and TNFR2 expression were up-regulated by HFB3-1hz6-hG1 and HFB3-1-hG1 in a dose-dependent manner, but isotype control and anti-OX40 antibody (BMS) were unable to trigger short-term NK activation.

Although signal response from hTNFR2 Knock-in (KI) mouse T cells was not as significant as that from human T cells, HFB3-1-hG1 and its humanized variant HFB3-1hz6-hG1 did induce more response (see FIG. 21), compared to the other antibodies. Of note, the lack of signal induction from the HFB3-18 series is expected.

Pharmacokinetic (PK) profiles of the subject humanized anti-TNFR2 monoclonal antibodies (HFB3-1hz6-hG1, HFB3-141c-hG1, and HFB3-18hz1-hG1) in C57BL/6 mice were examined. All three humanized monoclonal antibodies exhibited $T_{1/2}$ consistent with expectation for well-behaved antibodies. See below.

| | $T^{1/2}$ | Elimination Phase |
|---|---|---|
| HFB3-1hz6-hG1 | 4.9 days | 6.1 days to infinity |
| HFB3-141c-hG1 | 13.0 days | 5.7 days to infinity |
| HFB3-18hz1-hG1 | 10.6 days | 3.5 days to 8.6 days |

Example 13 Effects of Humanized HFB3-1hz6-hG1 on Activation of Natural Killer (NK) Cells Ex Vivo This experiment demonstrates that the subject humanized HFB3-1hz6-hG1 antibody co-stimulates natural killer (NK) cells in the presence of NK cell activation by IL-2/IL-15 or via CD3/CD28.

In one experiment, NK cells were isolated from peripheral blood mononuclear cells (PBMC) donated by two human patients using NK Cell Isolation Kit (Miltenyi Biotec). NK cells were first stimulated by soluble IL-2 (10 ng/mL) and IL-15 (10 ng/mL) for 24 hours, and then treated with isotype control antibody, mouse HFB3-1-hG1, humanized HFB3-1-hz6-hG1, or anti-OX40 control antibody (BMS) at 22 nM, 66 nM or 200 nM, respectively, for 16 hours. At the end of the experiment, CD107a expression on NK cell surface, which represents degranulation and activation of NK cells, as well as TNFR2 expression were measured by FACS.

Both mouse HFB3-1-hG1 and humanized HFB3-1-hz6-hG1 significantly increased NK cell activation in a dose dependent manner. Anti-OX40 antibody was unable to promote NK short term activation (40 hours since IL-2/IL-15 stimulation), likely due to insufficient OX40 expression.

In another experiment, whole PBMC donated by two human patients were co-stimulated by plate-bound anti-CD3 (1 μg/mL) and soluble anti-CD28 (1 μg/mL) for 48 hours, and then treated with isotype control antibody, mouse HFB3-1-hG1, humanized HFB3-1-hz6-hG1 or anti-OX40 antibody (BMS) at 22 nM, 66 nM or 200 nM, respectively, for 16 hours. CD107a expression was determined for CD3-negative/CD56-positive (i.e. NK cells). See FIG. 23.

Similarly, HFB3-1-hG1 and HFB3-1-hz6-hG1 significantly increased CD107a expression in a dose dependent manner, indicating that these antibodies can promote NK cell activation in whole PBMC. Under long-term activation (64 hours since anti-CD3/CD28 stimulation), anti-OX40 antibody was able to activate NK cells.

These data show that both humanized HFB3-1-hz6-hG1 and parental mouse HFB3-1-hG1 can promote NK cells activation.

Example 14 Pharmacodynamics of Humanized HFB3-1hz6-hG1 in MC38 Tumor Model

Figure 24A:
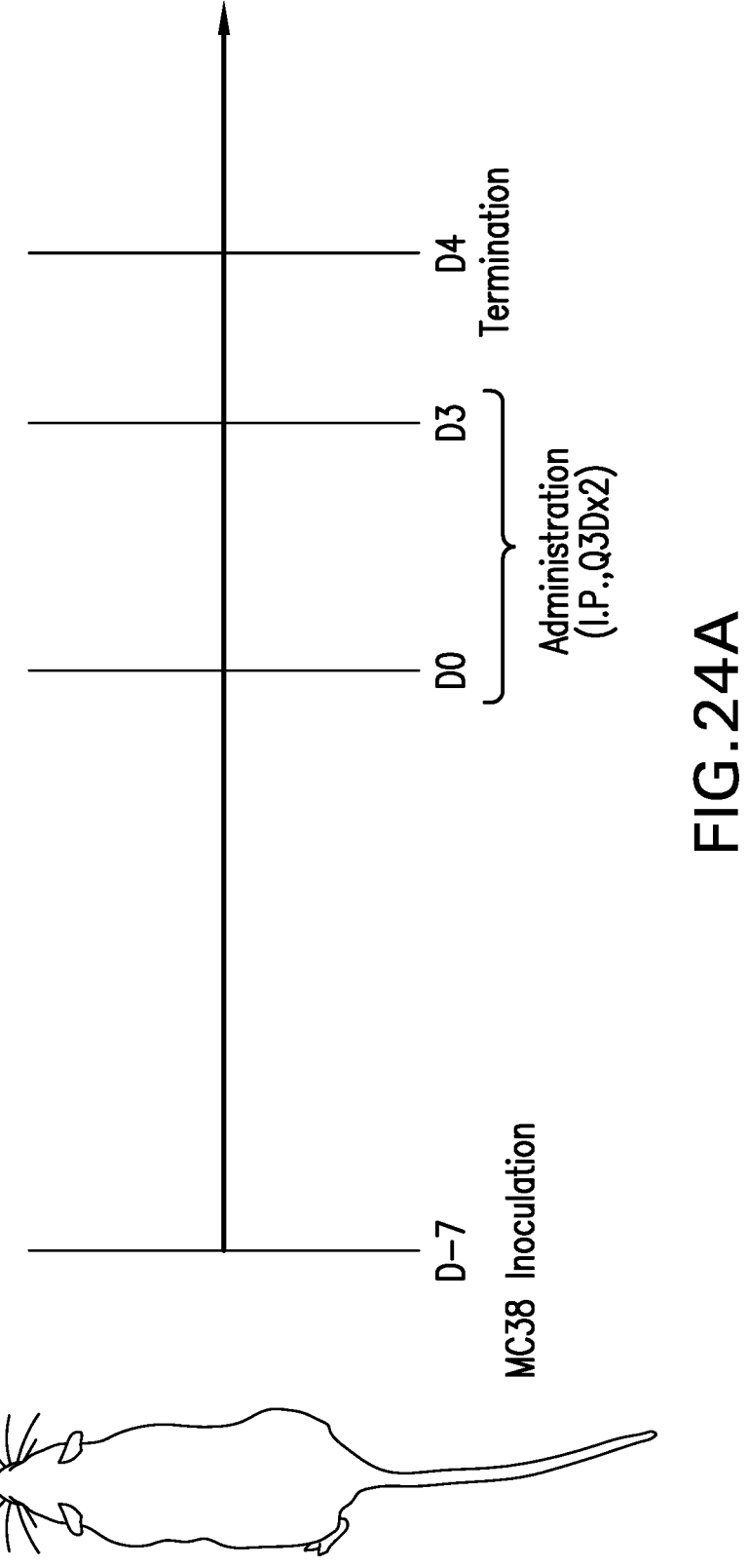
FIG. 24A shows timeline of pharmacodynamic experiment in mouse MC38 tumor model. 2 doses of HFB3-1-hG1 at 0.1 mg/kg, 1 mg/kg and 10 mg/kg dosage or isotype-matched control antibody (TT) at 10 mg/kg were administered intraperionatally 3 days apart.

Pharmacodynamics of HFB-1-hG1 were examined using MC38 colorectal cancer tumor model in the humanized TNFR2-KI mice (see FIG. 24A). Briefly, 8-week old humanized TNFR2 KI mice were inoculated into the right front flank with about 5×105 MC38 tumor cells per mouse. The mice were randomized and 7 days later, on Day 0, the mice (n=5 for each group) were injected intraperitoneally with HFB3-1-hG1 at 10 mg/kg, 1 mg/kg or 0.1 mg/kg, or with isotype control antibody at 10 mg/kg. The same treatment was administered again on D3. On Day 4, the mice were euthanized and pharmacodynamics readouts were carried out for tumor and blood samples. FACS was used to sort tumor-infiltrating leukocytes and peripheral leukocytes, as well as to determine receptor occupancy by antibody.

Figure 24B:
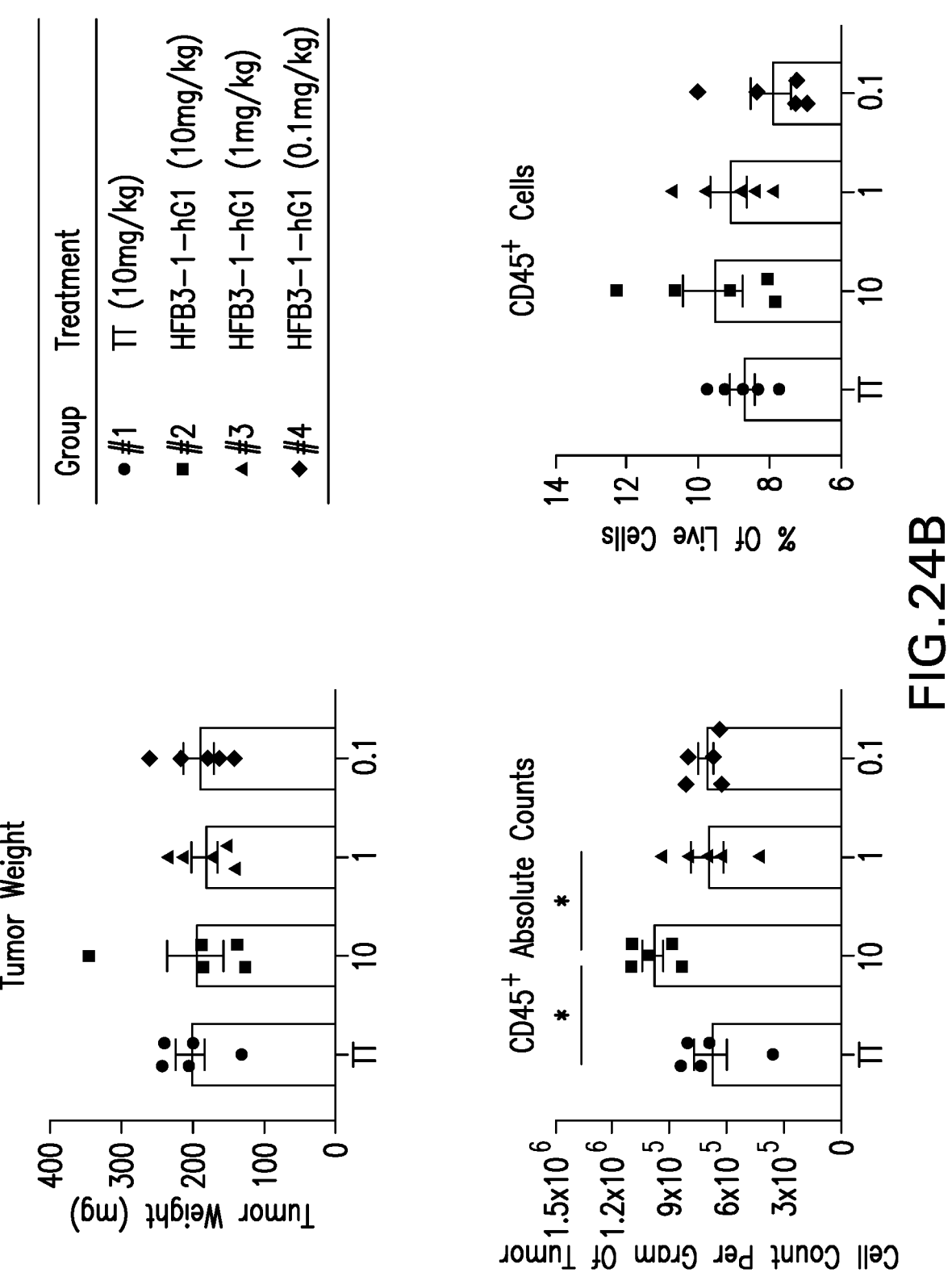
FIG. 24B shows in vivo effects of the antibody administration on total immune cell counts in MC38 tumor. Administration of HFB3-1-hG1 at 10 mg/kg increased absolute cell numbers of $CD45^+$ cells. p-value<0.05 (*) based on one-way ANOVA test.
Figure 24C:
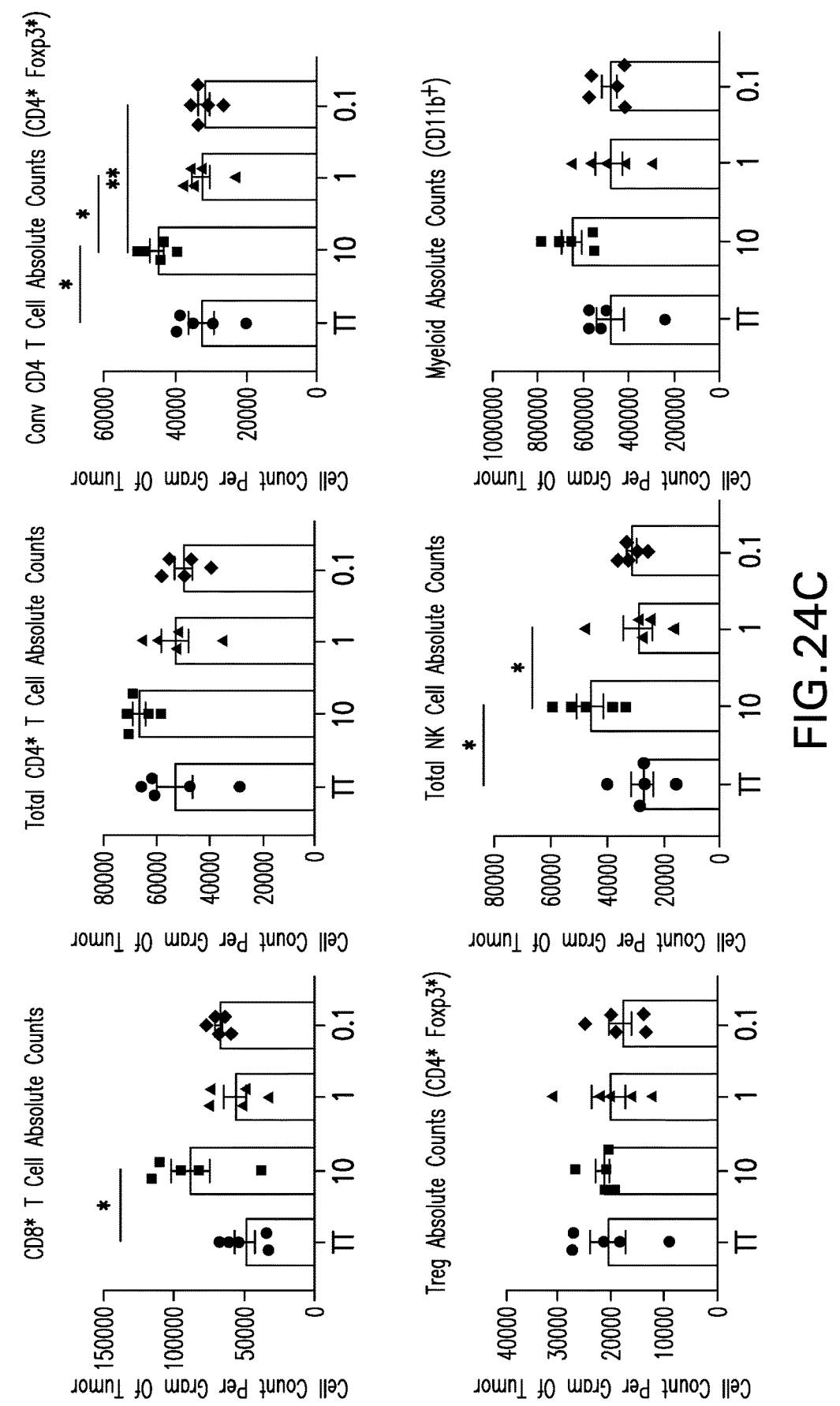
FIG. 24C shows in vivo effects on cell counts of different immune cells in MC38 tumor. Adminstration of HFB3-1-hG1 at 10 mg/kg increased absolute cell numbers of $CD8^+$, conventional $CD4^+$ T and NK cells in tumor microenvironment, but did not change the number of T-regulatory cells. *p-value<0.05 based on one-way ANOVA test.

After only 2 doses of treatment on Day 0 and Day 3, there was no significant difference in tumor weight among treatments yet (FIG. 24B, top left panel). Administration of HFB3-1-hG1 at 10 mg/kg increased absolute number of CD45+ cells present in the tumor (FIG. 24B, bottom left panel) but percentage of CD45+ among live cells of tumors was not significantly elevated (FIG. 24B, bottom right panel). Treatment of HFB3-1-hG1 at 10 mg/kg also increased absolute cell numbers of CD8+, conventional CD4+T and NK cells in tumor microenvironment, but did not change the number of T-regulatory cells (FIG. 24C). Administration of HFB3-1-hG1 at other lower doses did not result in any observable effects.

Figure 25A:
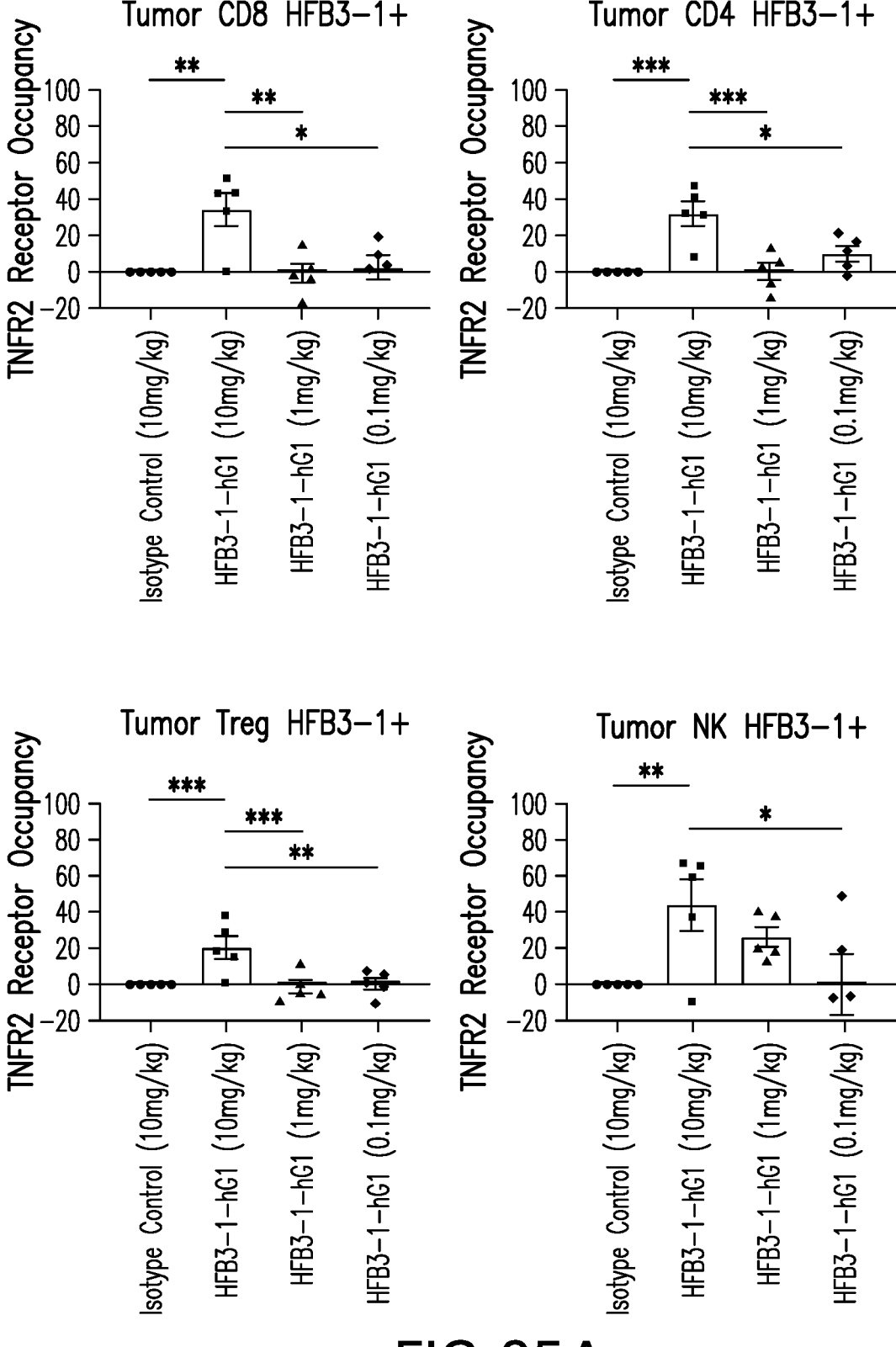
FIG. 25A shows percentage of TNFR2 receptor occupied by the injected antibody, HFB3-1-hG1 at 0.1 mg/kg, 1 mg/kg and 10 mg/kg dosage or control antibody at 10 mg/kg, on tumor-infiltrating leukocytes. Only HFB3-1-hG1 at 10 mg/kg dose resulted in drug receptor occupancy. p-value<0.05 (*), 0.01 () or 0.001 (*) based on one-way ANOVA test.
Figure 25B:
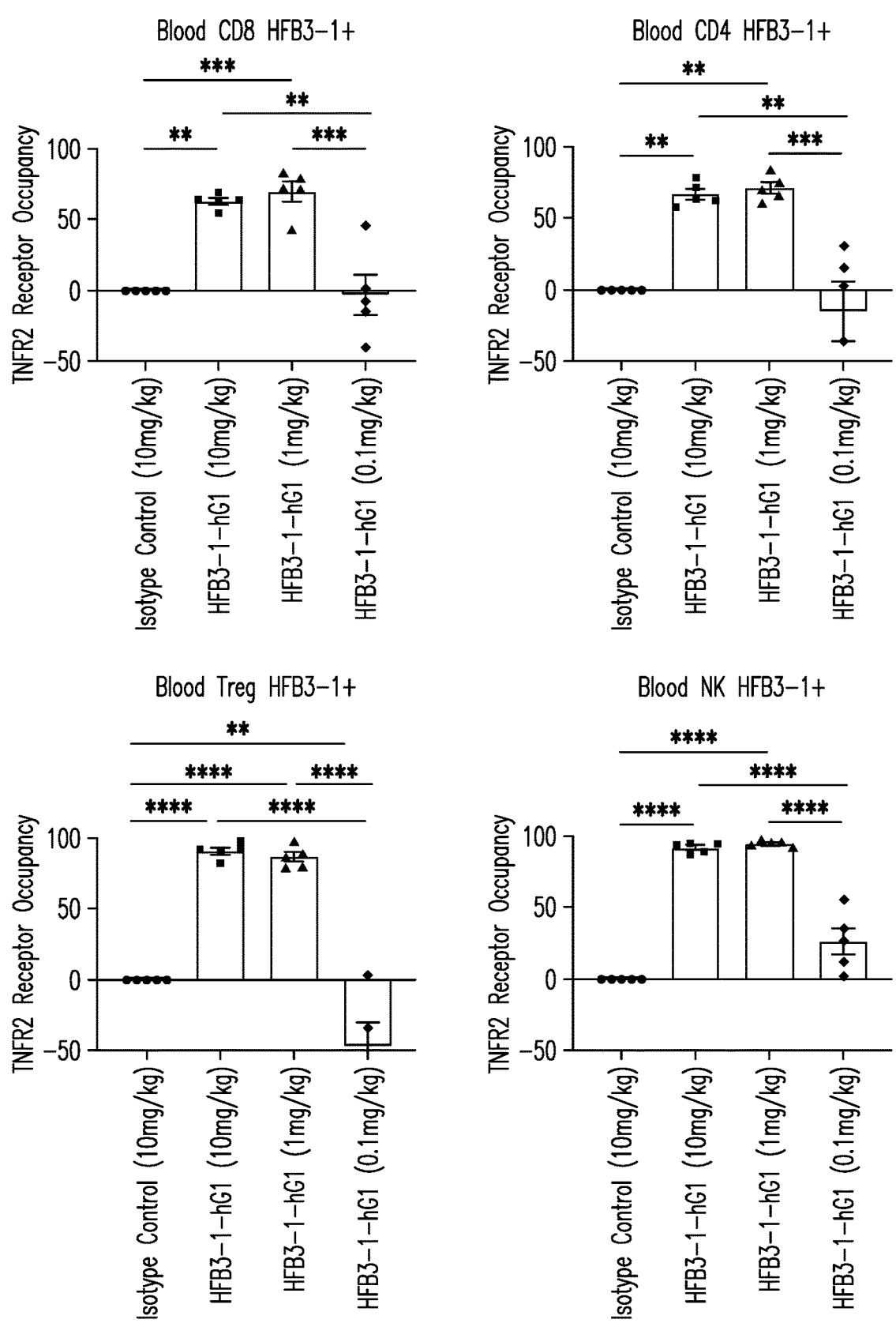
FIG. 25B shows percentage of TNFR2 receptor occupied by the injected antibody, HFB3-1-hG1 at 0.1 mg/kg, 1 mg/kg and 10 mg/kg dosage or control antibody at 10 mg/kg, on selected peripheral blood cells. HFB3-1-hG1 at 10 mg/kg and 1 mg/kg doses resulted in comparable drug receptor occupancy. p-value<0.05 (*), 0.01 () or 0.001 (*) based on one-way ANOVA test.

TNFR2 receptor occupancy was determined for CD8 T cells, conventional CD4 T cells, T-regulatory cells and NK cells in tumor and in peripheral blood. In tumor, only HFB3-1-hG1 at 10 mg/kg dose resulted in drug receptor occupancy on T cells in tumor; no occupancy was observed for the 1 and 0.1 mg/kg doses (see FIG. 25A). However, at 1 mg/kg and 10 mg/kg, receptor occupancy was observed in tumor NK cells. In peripheral blood, HFB3-1-hG1 at 10 mg/kg and 1 mg/kg doses resulted in comparable drug receptor occupancy and no significant occupancy was observed at the 0.1 mg/kg dose.

Figure 26A:
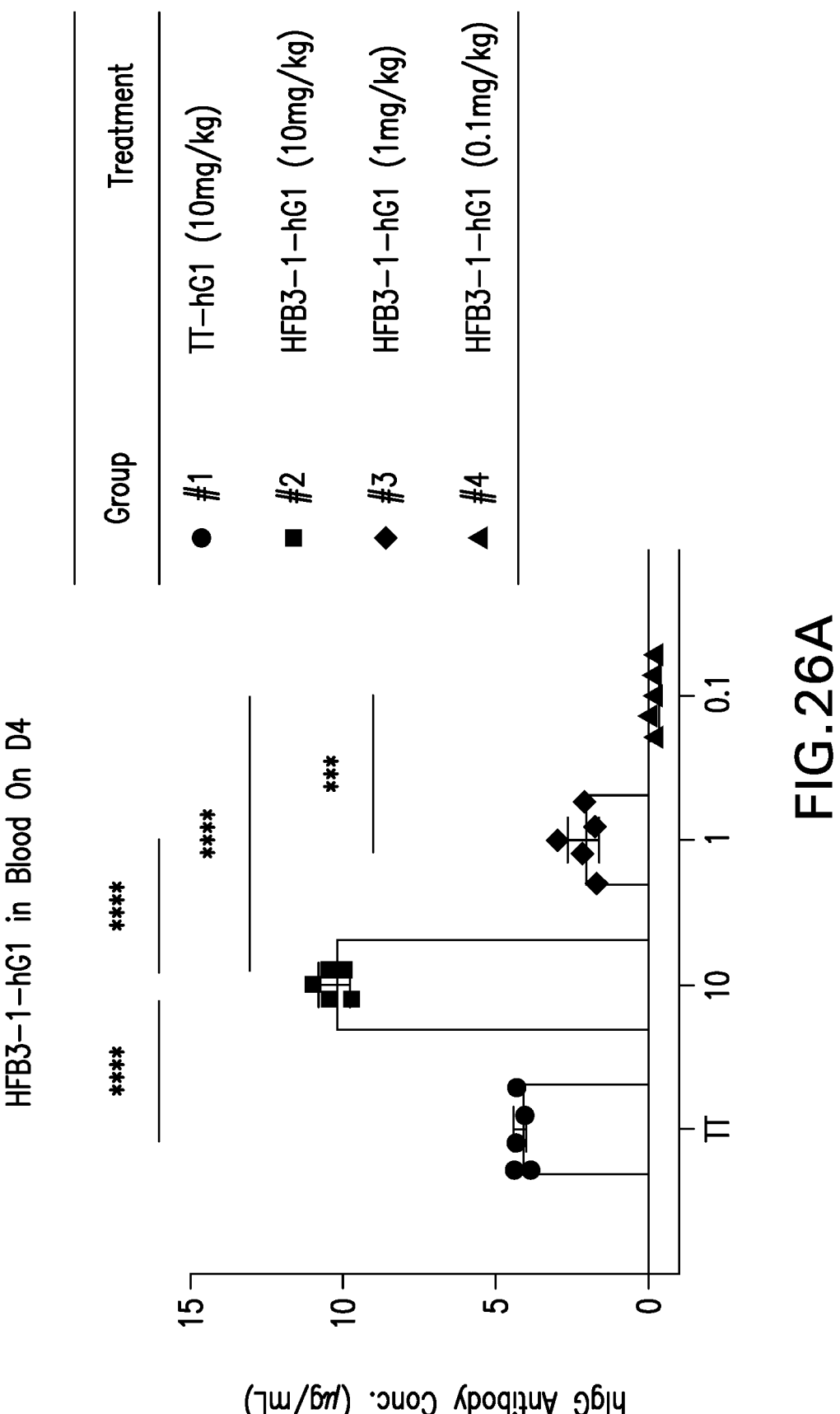
FIG. 26A shows antibody concentrations in blood on Day 4 of the experiment in FIG. 24A. HFB3-1-hG1 at 10 mg/kg and 1 mg/kg doses was detectable in blood. p-value<0.001 (*) or 0.0001 (**) based on one-way ANOVA test.
Figure 26B:
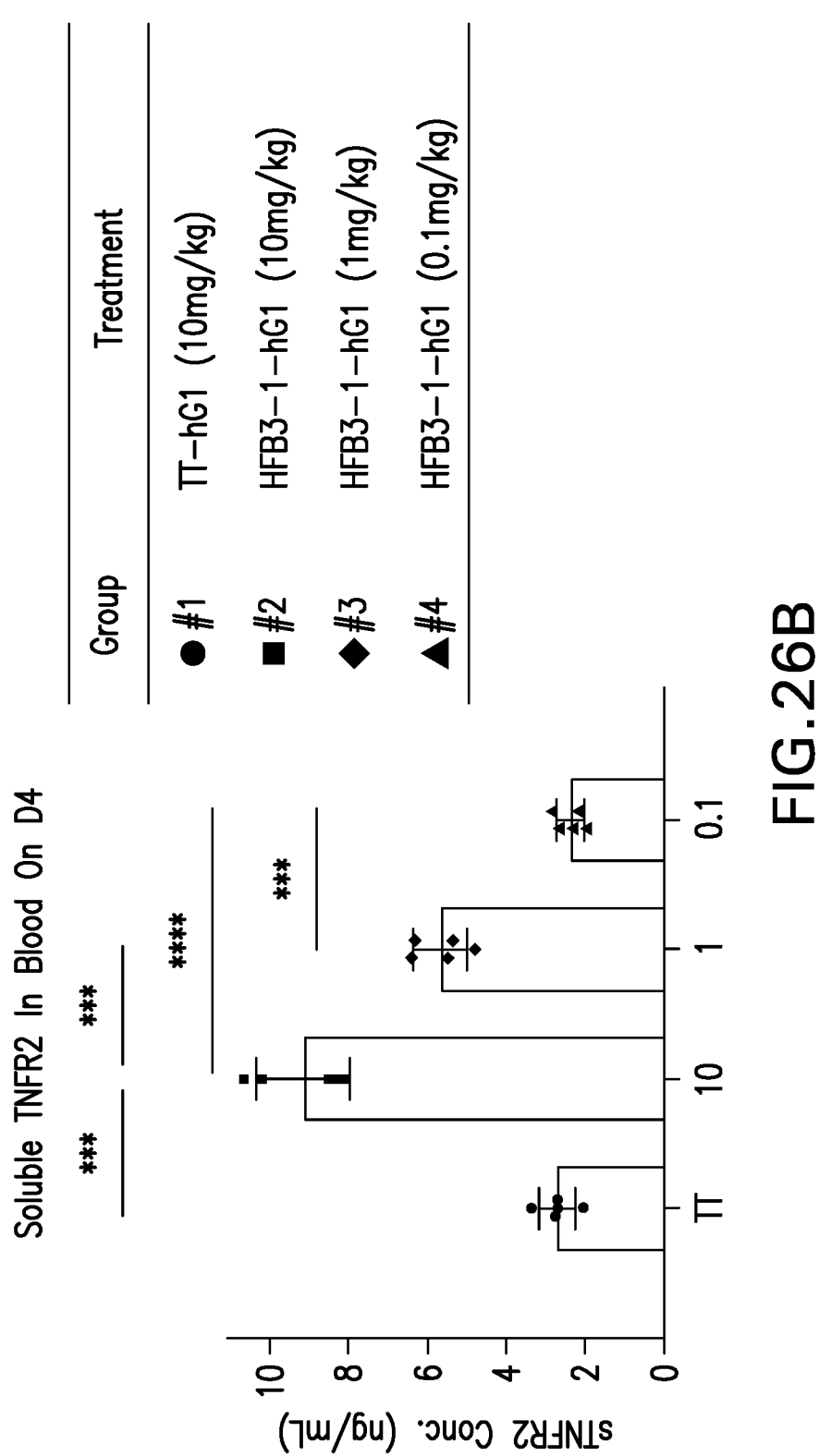
FIG. 26B shows soluble TNFR2 in blood on Day 4 of the experiment in FIG. 24A. 10 mg/kg and 1 mg/kg administrations of HFB3-1-hG1 increased the amount of TNFR2 detectable in blood. p-value<0.001 (*) or 0.0001 (**) based on one-way ANOVA test.

Pharmacokinetics of HFB3-1-hG1 was determined at the termination of the experiment. HFB3-1-hG1 administration at 1 and 10 mg/kg doses were detectable on Day 4 in blood. Remarkably, HFB3-1-hG1 at 10 mg/kg dose was retained at a much higher level than the isotype control at the same dose (see FIG. 26A). Interestingly, 10 mg/kg and 1 mg/kg administrations of HFB3-1-hG1 also increased the amount of TNFR2 detectable in blood (see FIG. 26B). TNFR2 in blood was presumably due to receptor shedding.

Overall, the data on short-term treatment of mice with HFB3-1-hG1 highly suggest that HFB3-1-hG1 has the potential to stimulate activation and proliferation of immune cells, effectively bind to TNFR2 receptors on immune cells and have good retention in blood in vivo.

Example 15 Synergistic Anti-Tumor Efficacy with Anti-PD-1 Antibody

Anti-tumor efficacy for the subject humanized anti-TNFR2 monoclonal antibodies were demonstrated in a widely-used mouse colorectal cancer model in the humanized TNFR2 KI mice background.

Figure 27B:
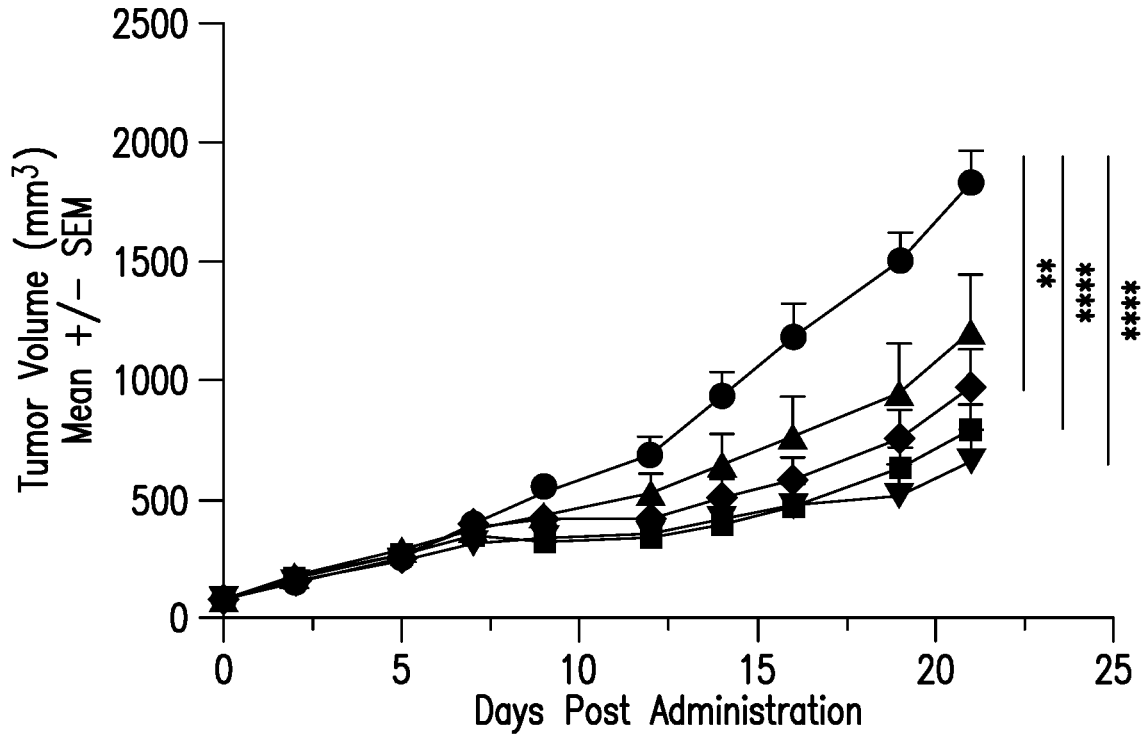

Specifically, 8-week old humanized TNFR2 KI mice were inoculated with about $5\times10^5$ MC38 tumor cells (which were derived from C57BL6 murine colon adenocarcinoma) per mouse. About 7 days later, at Day 0, the average tumor size in the mice reached about 89 mm$^3$ (between 74-98 mm$^3$). The mice were then randomized into 5 experimental groups (n=8 per group), for administering one of the following: (1) isotype-matched control (TT-hG1AA); (2) anti-mPD-1 (RMP-1-14); (3) HFB3-1hz6-hG1; (4) HFB3-14hz1c-hG1; and (5) HFB3-18hz1-hG1. The antibodies were injected intraperitoneally (i.p.) at a dose of about 10 mg/kg, on Days 0, 3, 6, 9, 12, 15, and 18, for a total of 7 doses (Q3D, ×7). Tumor volume was measured for the experimental groups over the course of the study. On or about Day 21, the average tumor volume reached >2000 mm$^3$ for the isotype control group, and the experiment was terminated and all mice were sacrificed. Tumor volume over time was plotted for the various groups in FIG. 27A and FIG. 27B. By day 21, statistical significance of tumor growth inhibition (TGI) is achieved in the groups of mice receiving HFB3-1hz6, HFB3-18hz1 and anti-PD-1 (RMP-14) (FIG. 27B).

The results showed that the humanized antibody HFB3-1hz6 and -hG1, and HFB3-18 hz1-hG1 inhibited tumor growth as potent as (if not better than) the anti-mPD-1 antibody, while the other humanized antibody was similarly effective, though to a slightly less degree. No apparent body weight difference was observed among the different groups of experimental mice.

Similar results were also obtained in another experiment using only anti-mPD-1 and HFB3-1hz6-hG1 and isotype control (4 mice per group), Q3d×3 (once every three days, for a total of three doses, of 10 mg/kg injected i.p.). At Day 6 (last dose of antibodies), tumor volumes were statistically significantly different between the isotype control group, and the anti-mPD-1 group and the HFB3-1hz6-hG1 group (based on 2-way ANOVA test). See FIG. 28.

Figure 29:
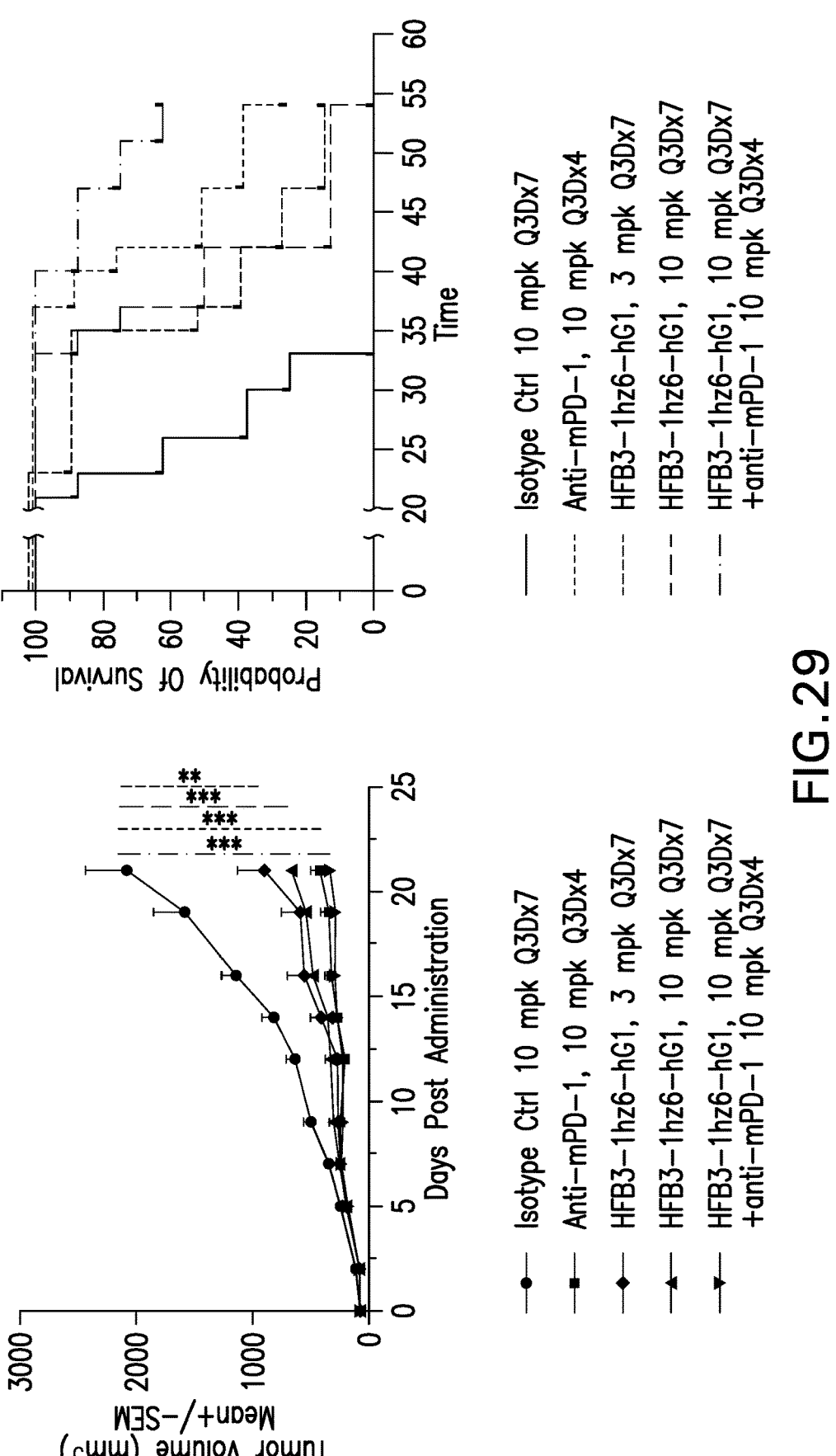
FIG. 29 shows that the humanized HFB3-1hz6 monoclonal antibody inhibits tumor growth and increases life span of tumor bearing mice at two different doses, 3 mg/kg and 10 mg/kg, and combination treatment with HFB3-1hz6 and anti-mPD-1 antibody extends survival better than treatment with anti-mPD-1 alone.

Moreover, the HFB3-1hz6-hG1 and anti-PD-1 antibody synergistically suppressed tumor growth and increased lifespan of mice in MC38 tumor model. Specifically, humanized TNRF2 KI mice were inoculated with MC38 cancer cells on day −7. From day 0, mice were injected intraperitoneally with isotype control, HFB3-1hz6-hG1 or anti-mPD-1 antibody singly or in combination every 3 days (n=8 per group). Treatment with 3 and 10 mg/kg HFB3-1hz6-hG1 every 3 days for a total of 7 doses (Q3d×7) and treatment with 10 mg/kg anti-PD-1 (RMP-14) every 3 days for a total of 4 doses (Q3d×4) significantly inhibited tumor growth and extended life span of mice in comparison to treatment with isotype control. Furthermore, combination treatment of both HFB3-1hz6-hG1 (10 mg/kg, Q3d×7) and anti-PD-1 antibody (10 mg/kg, Q3d×4) resulted in better survival than treatment with anti-PD-1 antibody alone. See FIG. 29. Data are analyzed using ANOVA comparing treatment groups to isotype control.

Example 14 Toxicological Evaluation of Anti-TNFR2 Antibodies in Non-Human Primates Toxicology of the humanized anti-TNFR2 antibodies were examined using a non-human primate model. Two cynomolgus monkeys per group were injected with a single dose of 15 mg/kg (low), 50 mg/kg (medium) and 150 mg/kg (high) of the humanized HFB3-1hz6-hG1 monoclonal antibody, after which plasma was collected at different time points until 336 hrs (day 14).

Figure 30:
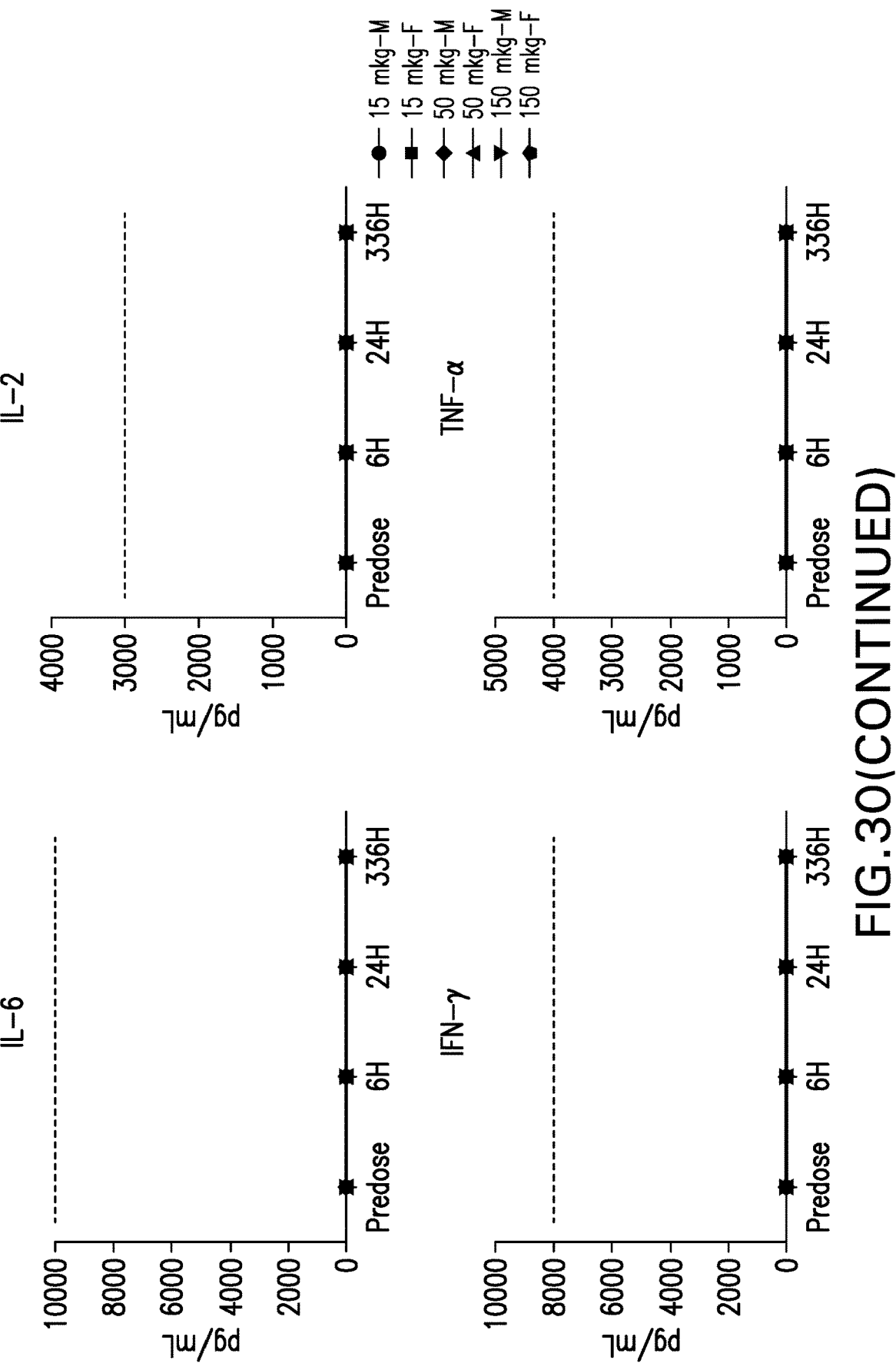
FIG. 30 shows that the humanized HFB3-1hz6 monoclonal antibody was eliminated from the body of cynomolgus monkeys over time, and no elevation of cytokines was observed after injecting 15, 50 or 150 mg/kg of HFB3-1hz6-hG1 in comparison to reported data (dotted lines) from CD3×CD20 bispecific IgG at <3 mg/kg.

Toxicokinetic analysis of HFB3-1hz6-hG1 showed that the antibody was eliminated over time. No elevation of cytokines IL-6, IL-2, IFN-γ and TNF-α was observed after the injection of 15, 50 or 150 mg/kg of HFB3-1hz6-hG1 in comparison to reported data (dotted lines) from CD3×CD20 bispecific IgG at <3 mg/kg (FIG. 30).

Figure 31:
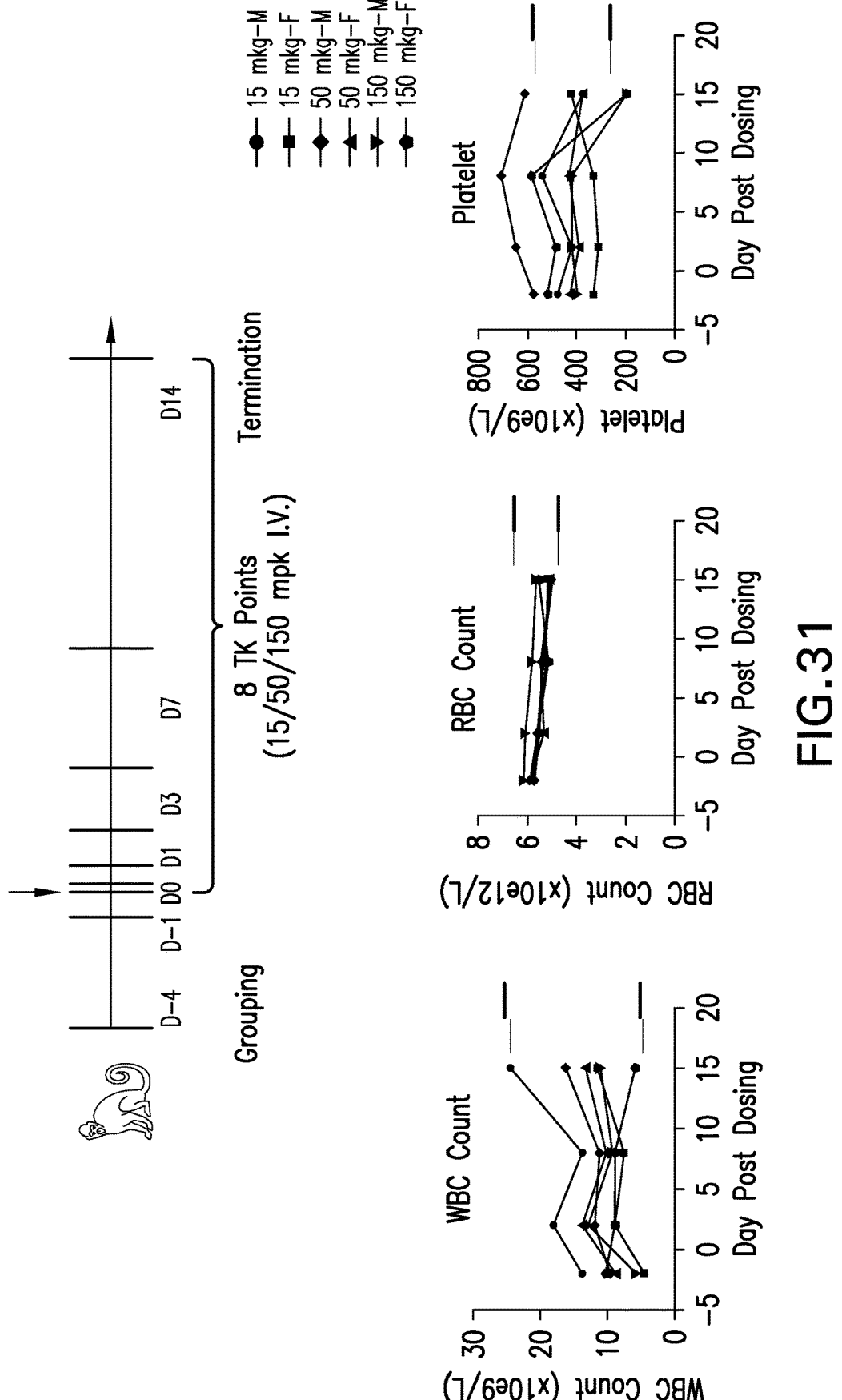
FIG. 31 shows cell count analysis after injection of 15, 50 or 150 mg/kg of HFB3-1hz6-hG1 compared to historical data range from normal monkeys (left and right lines in each panel).
Figure 31:
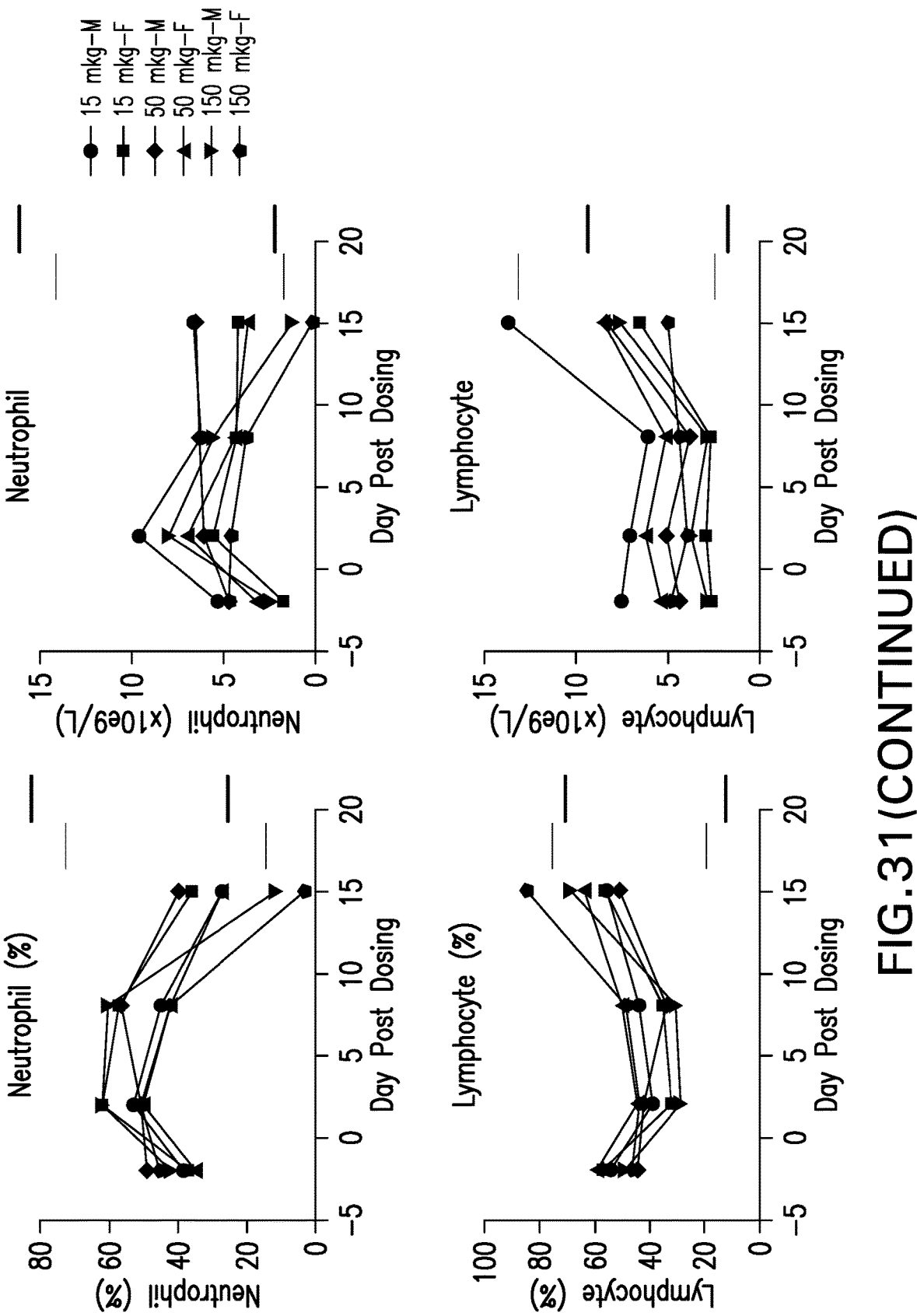

No abnormality was found in the numbers of white blood cells, red blood cells, platelets, neutrophils and lymphocytes after injection of 15, 50 or 150 mg/kg of HFB3-1hz6-hG1 compared to historical data range from normal monkeys (FIG. 31).

Toxicological evaluation so far showed no discernable toxic effects from treating the non-human primate subjects with HFB3-1hz6-hG1 with a dose up to 150 mg/kg.

The invention claimed is:

1. An isolated monoclonal antibody, or an antigen-binding fragment thereof, wherein said monoclonal antibody or antigen-binding fragment thereof is specific for human TNFR2, and wherein said monoclonal antibody comprises:

(3a) a heavy chain variable region (HCVR), comprising a HCVR CDR1 sequence of SEQ ID NO: 26, a HCVR CDR2 sequence of SEQ ID NO: 27, and a HCVR CDR3 sequence of SEQ ID NO: 28; and, (3b) a light chain variable region (LCVR), comprising a LCVR CDR1 sequence of SEQ ID NO: 29, a LCVR CDR2 sequence of SEQ ID NO: 30, and a LCVR CDR3 sequence of SEQ ID NO: 31; or (4a) a heavy chain variable region (HCVR), comprising a HCVR CDR1 sequence of SEQ ID NO: 39, a HCVR CDR2 sequence of SEQ ID NO: 40, and a HCVR CDR3 sequence of SEQ ID NO: 41; and, (4b) a light chain variable region (LCVR), comprising a LCVR CDR1 sequence of SEQ ID NO: 42, a LCVR CDR2 sequence of SEQ ID NO: 43, and a LCVR CDR3 sequence of SEQ ID NO: 44; or (5a) a heavy chain variable region (HCVR), comprising a HCVR CDR1 sequence of SEQ ID NO: 51, a HCVR CDR2 sequence of SEQ ID NO: 52, and a HCVR CDR3 sequence of SEQ ID NO: 53; and, (5b) a light chain variable region (LCVR), comprising a LCVR CDR1 sequence of SEQ ID NO: 54, a LCVR CDR2 sequence of SEQ ID NO: 55, and a LCVR CDR3 sequence of SEQ ID NO: 56; or (6a) a heavy chain variable region (HCVR), comprising a HCVR CDR1 sequence of SEQ ID NO: 63, a HCVR CDR2 sequence of SEQ ID NO: 64, and a HCVR CDR3 sequence of SEQ ID NO: 65; and, (6b) a light chain variable region (LCVR), comprising a LCVR CDR1 sequence of SEQ ID NO: 66, a LCVR CDR2 sequence of SEQ ID NO: 67, and a LCVR CDR3 sequence of SEQ ID NO: 68, wherein said isolated monoclonal antibody or antigen-binding fragment thereof is a human-mouse chimeric antibody, a humanized antibody, a CDR-grafted antibody, or a resurfaced antibody.

2. The isolated monoclonal antibody or antigen-binding fragment thereof of claim 1, wherein:

(3A) the HCVR sequence is the HCVR sequence of a monoclonal antibody having the heavy chain sequence of SEQ ID NO: 34; and/or, (3B) the LCVR sequence is the LCVR sequence of a monoclonal antibody having the heavy chain sequence of SEQ ID NO: 35, or, (4A) the HCVR sequence is the HCVR sequence of a monoclonal antibody having the heavy chain sequence of SEQ ID NO: 47; and/or, (4B) the LCVR sequence is the LCVR sequence of a monoclonal antibody having the heavy chain sequence of SEQ ID NO:48, or, (5A) the HCVR sequence is the HCVR sequence of a monoclonal antibody having the heavy chain sequence of SEQ ID NO: 59; and/or, (5B) the LCVR sequence is the LCVR sequence of a monoclonal antibody having the heavy chain sequence of SEQ ID NO:60, or, (6A) the HCVR sequence is the HCVR sequence of a monoclonal antibody having the heavy chain sequence of SEQ ID NO: 71; and/or, (6B) the LCVR sequence is the LCVR sequence of a monoclonal antibody having the heavy chain sequence of SEQ ID NO: 72.

3. The isolated monoclonal antibody or antigen-binding fragment thereof according to claim 1, wherein said monoclonal antibody has:

(3a) a heavy chain sequence of SEQ ID NO: 34; and/or, (3b) a light chain sequence of SEQ ID NO: 35, or, (4a) a heavy chain sequence of SEQ ID NO: 47; and/or, (4b) a light chain sequence of SEQ ID NO: 48, or, (5a) a heavy chain sequence of SEQ ID NO: 59; and/or, (5b) a light chain sequence of SEQ ID NO: 60, or, (6a) a heavy chain sequence of SEQ ID NO: 71; and/or, (6b) a light chain sequence of SEQ ID NO: 72.

4. The isolated monoclonal antibody or antigen-binding fragment thereof according to claim 1, which is a human-mouse chimeric antibody, a humanized antibody, a CDR-grafted antibody, or a resurfaced antibody.

5. The isolated monoclonal antibody or antigen-binding fragment thereof according to claim 1, wherein said antigen-binding fragment thereof is an Fab, Fab', F(ab')2, single chain Fv or scFv, disulfide linked Fv, IgGΔCH2, minibody, F(ab')3, tetrabody, triabody, diabody, DVD-Ig, mAb2, (scFv)2, or scFv-Fc.

6. The isolated monoclonal antibody or antigen-binding fragment thereof of claim 1, wherein said monoclonal antibody or antigen-binding fragment thereof does not substantially cross-react with TNFR1.

7. The isolated monoclonal antibody or antigen-binding fragment thereof of claim 1, wherein said monoclonal antibody or antigen-binding fragment thereof binds TNFR2 with a $K_d$ of less than about 25 nM, 20 nM, 15 nM, 10 nM, 5 nM, 2 nM, or 1 nM.

8. The isolated monoclonal antibody or antigen-binding fragment thereof of claim 1, which enhances binding between TNFα and TNFR2; enhances TNFα-mediated or -co-stimulated NFκB signaling and/or promotes TCR-activated effector T cell proliferation in the presence of Treg.

9. A method of treating cancer in a patient in need thereof, the method comprising administering to the patient an effective amount of the isolated monoclonal antibody or antigen-binding fragment thereof of claim 1.

10. The method of claim 9, which is for treating cancer, wherein the method further comprises administering an antagonist of an immune checkpoint.

11. The method of claim 10, wherein the immune checkpoint is PD-1/PD-L1 immune checkpoint.

12. The method of claim 10, wherein the antagonist of the immune checkpoint is:

(a) an antibody or antigen-binding fragment thereof specific for PD-1 or PD-L1, such as cemiplimab, nivolumab, pembrolizumab, avelumab, durvalumab, atezolizumab, KN035, or CK-301;

(b) a (non-antibody) peptide inhibitor of PD-1/PD-L1, such as AUNP12;

(c) a small molecule inhibitor of PD-L1 such as CA-170; or (d) a macrocyclic peptide such as BMS-986189.

13. The method of claim 10, wherein the cancer is melanoma, breast cancer, colon cancer, cervical cancer, renal cancer, liver cancer (e.g., heptocellular carcinoma), lung cancer (NSCLC), ovarian cancer, skin cancer (e.g., squamous cell carcinoma or basal cell carcinoma), lymphoma, or leukemia.

14. The method of claim 10, further comprising administering to the patient a chemotherapeutic agent, an anti-angiogenesis agent, a growth inhibitory agent, an immune-oncology agent, and/or an anti-neoplastic composition.

15. A polynucleotide encoding the heavy chain or the light chain or the antigen-binding portion thereof of claim 1.

16. The polynucleotide of claim 15, which is codon optimized for expression in a human cell.

17. A vector comprising the polynucleotide of claim 15.

* * * * *

SEQUENCE LISTING

<160> NUMBER OF SEQ ID NOS: 100

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 1

Ser Tyr Ser Phe Thr Asp Tyr Asn
1               5

<210> SEQ ID NO 2
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 2

Ile Phe Pro Lys Tyr Gly Thr Thr Ser Tyr Asn Gln Lys Phe Lys Gly
1               5                   10                  15

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 3

Ala Thr Asp Gly Gly Thr Trp Tyr Phe Asp Val
1               5                   10

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 4

Ser Ser Val Thr Tyr
1               5

<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 5

Leu Thr Ser Asn Leu Ala Ser Gly Val Pro Ala
1               5                   10

<210> SEQ ID NO 6

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gln Trp Ser Ser Asn Pro Pro Thr
1               5

<210> SEQ ID NO 7

<400> SEQUENCE: 7

000

<210> SEQ ID NO 8

<400> SEQUENCE: 8

000

<210> SEQ ID NO 9
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Phe Gln Leu Gln Gln Ser Gly Pro Glu Leu Val Lys Pro Gly Ala
1               5                   10                  15

Ser Val Lys Ile Ser Cys Lys Ala Ser Ser Tyr Ser Phe Thr Asp Tyr
            20                  25                  30

Asn Met Asn Trp Val Lys Gln Ser Asn Gly Lys Ser Leu Glu Trp Ile
        35                  40                  45

Gly Ile Ile Phe Pro Lys Tyr Gly Thr Thr Ser Tyr Asn Gln Lys Phe
    50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Thr Asp Gly Gly Thr Trp Tyr Phe Asp Val Trp Gly Thr Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

```
            210                 215                 220
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

```
<210> SEQ ID NO 10
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Ile Val Leu Thr Gln Ser Pro Ala Leu Met Ser Ala Ser Pro Gly
1                   5                   10                  15

Glu Lys Val Thr Met Thr Cys Ser Ala Ser Ser Ser Val Thr Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
gaatttcagc tgcagcagtc tggccccgag ctggttaagc ctggcgcctc tgtgaagatc      60
agctgcaagg ccagcagcta cagcttcacc gactacaaca tgaactgggt caagcagagc     120
aacggcaaga gcctggaatg gatcggcatc atcttccctca agtacggcac caccagctac     180
aaccagaagt tcaagggcaa agccacactg accgtggacc agagcagcag cacagcctac     240
atgcagctca acagcctgac cagcgaggac agcgccgtgt actactgtgc tacagatggc     300
ggcacctggt acttcgatgt gtggggcact ggcaccaccg tgacagttag ttctgcgtcg     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca gaaagttga gcccaaatct      660 tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtccccggg taaatga                                        1347

<210> SEQ ID NO 12
```

-continued

```
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
cagattgtgc tgacacagtc tcccgctctg atgagcgcta gccctggcga gaaagtgacc       60
atgacatgta gcgccagcag cagcgtgacc tacatgtact ggtatcagca gaagcccaga      120
agcagcccca agccttggat ctacctgacc agcaatctgg ccagcggagt gcctgccaga      180
ttttctggct ctggcagcgg cacaagctac agcctgacaa tcagcagcat ggaagccgag      240
gatgccgcca cctactactg ccagcagtgg tccagcaatc ctcctacatt tggctccggc      300
accaagctgg aaatcaagcg tacggtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                        642

<210> SEQ ID NO 13
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Cys Glu Asp Ser Thr Tyr Thr Gln Leu Trp Asn Trp Val Pro Glu
1               5                   10                  15

Cys Leu Ser

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Tyr Ser Phe Thr Asp Tyr Asn
1               5

<210> SEQ ID NO 15
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ile Phe Pro Lys Tyr Gly Thr Thr Ser Tyr Ala Gln Lys Leu Gln Gly
1               5                   10                  15
```

```
<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ala Thr Asp Gly Gly Thr Trp Tyr Phe Asp Val
1               5                   10

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Ser Val Thr Tyr
1               5

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Leu Thr Ser Asn Leu Ala Ser Gly Val Pro Ser
1               5                   10

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gln Gln Trp Ser Ser Asn Pro Pro Thr
1               5

<210> SEQ ID NO 20

<400> SEQUENCE: 20

000

<210> SEQ ID NO 21

<400> SEQUENCE: 21

000

<210> SEQ ID NO 22
<211> LENGTH: 448
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Val Gln Ser Gly Ala Glu Leu Lys Lys Pro Gly Ala
1               5                   10                  15

Ser Val Lys Val Ser Cys Lys Ala Ser Ser Tyr Ser Phe Thr Asp Tyr
                20                  25                  30

Asn Met Asn Trp Val Arg Gln Ala Pro Gly Gln Ser Leu Glu Trp Met
            35                  40                  45

Gly Ile Ile Phe Pro Lys Tyr Gly Thr Thr Ser Tyr Ala Gln Lys Leu
        50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Asp Gly Gly Thr Trp Tyr Phe Asp Val Trp Gly Thr Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

-continued

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 23
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Tyr Met
                20                  25                  30

Tyr Trp Tyr Gln Gln Lys Pro Gly Lys Ala Pro Lys Pro Trp Ile Tyr
            35                  40                  45

Leu Thr Ser Asn Leu Ala Ser Gly Val Pro Ser Arg Phe Ser Gly Ser
        50                  55                  60

Gly Ser Gly Thr Glu Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 24
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
caggttcagc tggttcagtc tggcgccgag ctgaaaaaac ctggcgcctc tgtgaaggtg      60
```

-continued

```
tcctgcaagg ccagcagcta cagcttcacc gactacaaca tgaactgggt ccgacaggcc      120
cctggccagt ctcttgagtg gatgggcatc atcttcccta agtacggcac caccagctac      180
gcccagaaac tgcagggaag agtgaccctg accaccgaca ccagcacaag caccgcctac      240
atggaactgc ggagcctgag atccgatgac accgccgtgt actactgtgc cacagatggc      300
ggcacctggt acttcgatgt gtggggcact ggcaccaccg tgacagtctc ttctgcgtcg      360
accaagggcc catcggtctt ccccctggca ccctcctcca agagcacctc tgggggcaca      420
gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct tgggcaccca gacctacatc      600
tgcaacgtga atcacaagcc cagcaacacc aaggtggaca gaaagttga gcccaaatct      660 tgtgacaaaa ctcacacatg cccaccgtgc ccagcacctg aactcctggg gggaccgtca      720
gtcttcctct tccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca aagccgcggg aggagcagta caacagcacg      900
taccgtgtgg tcagcgtcct caccgtcctg caccaggact ggctgaatgg caaggagtac      960
aagtgcaagg tctccaacaa agccctccca gccccatcg agaaaaccat ctccaaagcc     1020
aaagggcagc cccgagaacc acaggtgtac accctgcccc catcccggga ggagatgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctatagcaag ctcaccgtgg acaagagcag gtggcagcag     1260
gggaacgtct tctcatgctc cgtgatgcat gaggctctgc acaaccacta cacgcagaag     1320
agcctctccc tgtccccggg taaatga                                        1347
```

```
<210> SEQ ID NO 25
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gacatccagc tgacccagtc tccaagcttt ctgagcgcca gcgtgggcga cagagtgacc       60
attacatgta gagccagcag cagcgtgacc tatatgtact ggtatcagca gaagcccggc      120
aaggccccta gccttggat ctacctgacc agcaatctgg ccagcggcgt gccaagcaga      180
ttttctggct ctggcagcgg caccgagtac accctgacca tatctagcct gcagcctgag      240
gatgccgcca cctactattg ccagcagtgg tccagcaatc ctcctacctt tggctccggc      300
accaagctgg aaatcaagcg tacggtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                        642
```

```
<210> SEQ ID NO 26
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Tyr Thr Phe Thr Asp Tyr Tyr
1               5

<210> SEQ ID NO 27
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ile Asn Pro Asn Asp Gly Gly Thr Thr Tyr Ser Gln Lys Phe Lys Gly
1               5                   10                  15

<210> SEQ ID NO 28
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Arg Glu Gly Asn Tyr Tyr Ala Tyr Asp Val Arg Val Trp Tyr Phe
1               5                   10                  15

Asp Val

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gln Asp Ile Ile Thr Tyr
1               5

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ser Thr Ser Ser Leu Asn Ser Gly Val Pro Ser
1               5                   10

<210> SEQ ID NO 31
```

-continued

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 31

Gln Gln Tyr Ser Glu Leu Pro Tyr Thr
1               5

<210> SEQ ID NO 32

<400> SEQUENCE: 32

000

<210> SEQ ID NO 33

<400> SEQUENCE: 33

000

<210> SEQ ID NO 34
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 34

Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asp Gly Gly Thr Thr Tyr Ser Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Glu Gly Asn Tyr Tyr Ala Tyr Asp Val Arg Val Trp Tyr Phe
            100                 105                 110

Asp Val Trp Gly Thr Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
```

-continued

```
        210              215              220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
                355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 35
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asp Ile Gln Met Thr Gln Ser Pro Ala Ser Leu Ser Val Ser Val Gly
1               5                   10                  15

Glu Thr Val Thr Ile Thr Cys Arg Ser Ser Glu Asn Ile Tyr Ser Asn
                20                  25                  30

Leu Ala Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys Arg Thr Val Ala Ala
                100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 36
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
gaagttcagc tgcagcagtc tggacccgag ctggttaagc ctggcgcctc tgtcagaatc       60
agctgcaagg ccagcggcta caccttcacc gactactaca tgaactgggt caagcagagc      120
cacggcaaga gcctggaatg gatcggcgac atcaacccca tgatggcggg caccacctac      180
agccagaagt tcaagggcaa agccacactg accgtggaca gagcagcag caccgcctac      240 atggaactga agagcctgac cagcgaggac agcgccgtgt actttgtgc cagagagggc      300 aactactacg cctacgacgt ccgcgtgtgg tacttcgatg tgtggggcac aggcaccacc      360
gtgacagtta gttctgcgtc gaccaagggc ccatcggtct tccccctggc accctcctcc      420
aagagcacct ctgggggcac agcggccctg ggctgcctgg tcaaggacta cttccccgaa      480
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcaccc agacctacat ctgcaacgtg aatcacaagc ccagcaacac caaggtggac      660
aagaaagttg agcccaaatc ttgtgacaaa actcacacat gcccaccgtg cccagcacct      720
gaactcctgg gggaccgtc agtcttcctc ttccccccaa aacccaagga caccctcatg      780
atctcccgga cccctgaggt cacatgcgtg gtggtggacg tgagccacga agaccctgag      840
gtcaagttca actggtacgt ggacggcgtg gaggtgcata atgccaagac aaagccgcgg      900
gaggagcagt acaacagcac gtaccgtgtg gtcagcgtcc tcaccgtcct gcaccaggac      960
tggctgaatg gcaaggagta caagtgcaag gtctccaaca aagccctccc agcccccatc     1020
gagaaaacca tctccaaagc caaagggcag ccccgagaac cacaggtgta caccctgccc     1080
ccatcccggg aggagatgac caagaaccag gtcagcctga cctgcctggt caaaggcttc     1140
tatcccagcg acatcgccgt ggagtgggag agcaatgggc agccggagaa caactacaag     1200
accacgcctc ccgtgctgga ctccgacggc tccttcttcc tctatagcaa gctcaccgtg     1260
gacaagagca ggtggcagca ggggaacgtc ttctcatgct ccgtgatgca tgaggctctg     1320
cacaaccact acacgcagaa gagcctctcc ctgtccccgg gtaaatga                   1368
```

```
<210> SEQ ID NO 37
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
gacatccaga tgacacagtc tccagccagc ctgtccgtgt ctgtgggaga gacagtgacc        60
atcacctgtc ggagcagcga gaacatctac agcaacctgg cctggtatca gcagaagcag       120
ggcaagtctc ctcagctgct ggtgtacgcc gccaccaatc ttgctgatgg cgtgcccagc       180 agatttccg gctctggctc tggcacacag tacagcctga agatcaacag cctgcagagc        240
gaggacttcg gcagctacta ctgccagcac ttttggggca ccccttggac atttggcgga       300
ggcaccaagc tggaaatcaa gcgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gttag                       645

<210> SEQ ID NO 38
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Cys Ala Pro Leu Arg Lys Cys Arg Pro Gly Phe Gly Val Ala Arg Pro
1               5                   10                  15

Gly Thr Glu Thr Ser Asp
            20

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Tyr Thr Phe Thr Asp Tyr Tyr
1               5

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40
```

```
Ile Asn Pro Asn Asp Gly Gly Thr Thr Tyr Ala Gln Lys Phe Gln Gly
1               5                   10                  15
```

```
<210> SEQ ID NO 41
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 41
```

```
Ala Arg Glu Gly Asn Tyr Tyr Ala Tyr Asp Val Arg Val Trp Tyr Phe
1               5                   10                  15
```

```
Asp Val
```

```
<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 42
```

```
Gln Asp Ile Ile Thr Tyr
1               5
```

```
<210> SEQ ID NO 43
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 43
```

```
Ser Thr Ser Ser Leu Asn Ser Gly Val Pro Ser
1               5                   10
```

```
<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 44
```

```
Gln Gln Tyr Ser Glu Leu Pro Tyr Thr
1               5
```

```
<210> SEQ ID NO 45
```

```
<400> SEQUENCE: 45
```

```
000
```

```
<210> SEQ ID NO 46
```

```
<400> SEQUENCE: 46
```

```
000
```

<210> SEQ ID NO 47
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Asp Ile Asn Pro Asn Asp Gly Gly Thr Thr Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Gly Asn Tyr Tyr Ala Tyr Asp Val Arg Val Trp Tyr Phe
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

```
Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 48
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asp Ile Ile Thr Tyr
            20                  25                  30

Leu Asn Trp Tyr Gln Gln Lys Pro Gly Lys Ala Val Lys Leu Leu Ile
        35                  40                  45

Tyr Ser Thr Ser Ser Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Glu Leu Pro Tyr
                85                  90                  95

Thr Phe Gly Gly Gly Thr Lys Val Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 1368
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49

```
caggttcagc tggttcagtc tggcgccgaa gtgaagaaac ctggcagcag cgtgaaggtg       60
tcctgcaagg ccagcggcta cacctttacc gactactaca tgaactgggt ccgacaggcc      120
cctggacagg gacttgaatg gatgggcgac atcaaccoca cgacggcgg cacaacatac       180 gcccagaaat tccagggcag agtgaccatc accgccgacg agtctacaag caccgcctac      240
atggaactga gcagcctgag aagcgaggat accgccgtgt acttctgtgc cagagagggc      300
aactactacg cctacgacgt ccgcgtgtgg tacttcgatg tttggggcca gggcaccacc      360
gtgacagtct cttctgcgtc gaccaagggc ccatcggtct tccccctggc acctcctcc      420 aagagcacct ctgggggcac agcggccctg ggctgcctgg tcaaggacta cttccccgaa      480
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcaccc agacctacat ctgcaacgtg aatcacaagc ccagcaacac caaggtggac      660
aagaaagttg agcccaaatc ttgtgacaaa actcacacat gcccaccgtg cccagcacct      720
gaactcctgg gggaccgtc agtcttcctc ttccccccaa aacccaagga cacctcatg       780 atctcccgga cccctgaggt cacatgcgtg gtggtggacg tgagccacga agaccctgag      840
gtcaagttca actggtacgt ggacggcgtg gaggtgcata atgccaagac aaagccgcgg      900
gaggagcagt acaacagcac gtaccgtgtg gtcagcgtcc tcaccgtcct gcaccaggac      960
tggctgaatg gcaaggagta caagtgcaag gtctccaaca aagccctccc agcccccatc     1020
gagaaaacca tctccaaagc caaagggcag ccccgagaac cacaggtgta caccctgccc     1080
ccatcccggg aggagatgac caagaaccag gtcagcctga cctgcctggt caaaggcttc     1140
tatcccagcg acatcgccgt ggagtgggag agcaatgggc agccggagaa caactacaag     1200
accacgcctc ccgtgctgga ctccgacggc tccttcttcc tctatagcaa gctcaccgtg     1260
gacaagagca ggtggcagca ggggaacgtc ttctcatgct ccgtgatgca tgaggctctg     1320
cacaaccact acacgcagaa gagcctctcc ctgtccccgg gtaaatga                  1368
```

<210> SEQ ID NO 50
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

```
gacatccaga tgacacagag ccctagcagc ctgtctgcca gcgtgggaga cagagtgacc       60
attacatgtg cgccagcca ggacatcatc acctacctga actggtatca gcagaaaccc      120
ggcaaggccg tgaagctgct gatctacagc accagcagcc tgaatagcgg cgtgcccagc      180
agattttctg gcagcggctc tggcaccgac ttcaccctga ccatatctag cctgcagcct      240
gaggacttcg ccacctacta ctgccagcag tacagcgagc tgccctacac atttggcgga      300
ggcaccaagg tggaactgaa gcgtacggtt gctgcccctt ccgtgttcat cttcccacct      360
tccgacgagc agctgaagtc tggcacagcc tctgtcgtgt gcctgctgaa caacttctac      420
```

-continued

```
cctcgggaag ccaaggtgca gtggaaggtg dacaatgccc tgcagtccgg caactcccaa        480
gagtctgtga ccgagcagga ctccaaggac agcacctaca gcctgtcctc cacactgacc        540
ctgtccaagg ccgactacga gaagcacaag gtgtacgcct gcgaagtgac ccatcagggc        600
ctgtctagcc ctgtgaccaa gtctttcaac cggggcgagt gttag                        645
```

<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gly Phe Thr Phe Ser Asp Ala Trp
1               5

<210> SEQ ID NO 52
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Val Arg Asn Lys Ala Asn Asn His Ala Thr Tyr Tyr Ala Glu Ser Val
1               5                   10                  15

Lys Gly

<210> SEQ ID NO 53
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Thr Arg Ser Val Gly Gly Tyr Gly Thr Thr Tyr Trp Tyr Phe Asp Val
1               5                   10                  15

<210> SEQ ID NO 54
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gln Asn Leu Leu Asn Ser Gly Asn Gln Lys Asn Tyr
1               5                   10

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

```
     Synthetic peptide"

<400> SEQUENCE: 55

Gly Ala Ser Thr Arg Glu Ser Gly Val Pro Asp
1               5                   10

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 56

Gln Ser Glu His Ser Tyr Pro Tyr Thr
1               5

<210> SEQ ID NO 57

<400> SEQUENCE: 57

000

<210> SEQ ID NO 58

<400> SEQUENCE: 58

000

<210> SEQ ID NO 59
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 59

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Val Arg Asn Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Ser Val Gly Gly Tyr Gly Thr Thr Tyr Trp Tyr Phe
            100                 105                 110

Asp Val Trp Gly Thr Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
```

```
                          165                     170                     175
Thr Phe Pro Ala Val Leu Gln Ser Ser Gly Leu Tyr Ser Leu Ser Ser
                180                     185                     190

Val Val Thr Val Pro Ser Ser Ser Leu Gly Thr Gln Thr Tyr Ile Cys
                195                     200                     205

Asn Val Asn His Lys Pro Ser Asn Thr Lys Val Asp Lys Lys Val Glu
        210                     215                     220

Pro Lys Ser Cys Asp Lys Thr His Thr Cys Pro Pro Cys Pro Ala Pro
225                     230                     235                     240

Glu Leu Leu Gly Gly Pro Ser Val Phe Leu Phe Pro Pro Lys Pro Lys
                245                     250                     255

Asp Thr Leu Met Ile Ser Arg Thr Pro Glu Val Thr Cys Val Val Val
                260                     265                     270

Asp Val Ser His Glu Asp Pro Glu Val Lys Phe Asn Trp Tyr Val Asp
                275                     280                     285

Gly Val Glu Val His Asn Ala Lys Thr Lys Pro Arg Glu Glu Gln Tyr
        290                     295                     300

Asn Ser Thr Tyr Arg Val Val Ser Val Leu Thr Val Leu His Gln Asp
305                     310                     315                     320

Trp Leu Asn Gly Lys Glu Tyr Lys Cys Lys Val Ser Asn Lys Ala Leu
                325                     330                     335

Pro Ala Pro Ile Glu Lys Thr Ile Ser Lys Ala Lys Gly Gln Pro Arg
                340                     345                     350

Glu Pro Gln Val Tyr Thr Leu Pro Pro Ser Arg Glu Glu Met Thr Lys
                355                     360                     365

Asn Gln Val Ser Leu Thr Cys Leu Val Lys Gly Phe Tyr Pro Ser Asp
        370                     375                     380

Ile Ala Val Glu Trp Glu Ser Asn Gly Gln Pro Glu Asn Asn Tyr Lys
385                     390                     395                     400

Thr Thr Pro Pro Val Leu Asp Ser Asp Gly Ser Phe Phe Leu Tyr Ser
                405                     410                     415

Lys Leu Thr Val Asp Lys Ser Arg Trp Gln Gln Gly Asn Val Phe Ser
                420                     425                     430

Cys Ser Val Met His Glu Ala Leu His Asn His Tyr Thr Gln Lys Ser
                435                     440                     445

Leu Ser Leu Ser Pro Gly Lys
        450                     455
```

<210> SEQ ID NO 60
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 60

```
Asp Ile Val Met Thr Gln Ser Pro Ser Ser Leu Ser Val Ser Ala Gly
1                       5                       10                      15

Glu Lys Val Thr Met Ser Cys Lys Ser Ser Gln Asn Leu Leu Asn Ser
                20                      25                      30

Gly Asn Gln Lys Asn Tyr Leu Ala Trp Tyr Gln Gln Lys Pro Gly Gln
        35                      40                      45

Pro Pro Lys Leu Leu Ile Phe Gly Ala Ser Thr Arg Glu Ser Gly Val
        50                      55                      60
```

```
Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Ser
                    85                  90                  95

Glu His Ser Tyr Pro Tyr Thr Phe Gly Gly Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220
```

<210> SEQ ID NO 61
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61

```
gaagtgaagc tggaagaatc tggcggcgga ctggttcagc ctggcggatc tatgaagctg     60
agctgtgccg ccagcggctt cacctttct gacgcctgga tggactgggt ccgacagtct    120
cctgagaaag gcctggaatg ggttgccgaa gtgcggaaca aggccaacaa ccacgccacc    180
tactacgccg agtctgtgaa gggcagattc accatcagcc gggacgacag caagagcagc    240
gtgtacctgc agatgaacag cctgagagcc gaggacaccg gcatctacta ctgcacaaga    300
agcgttggcg gctacggcac cacctactgg tactttgatg tgtggggcac cggcaccaca    360
gtgaccgtta gttctgcgtc gaccaagggc ccatcggtct tccccctggc accctcctcc    420
aagagcacct ctgggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagaaagttg agcccaaatc ttgtgacaaa actcacacat gcccaccgtg cccagcacct    720
gaactcctgg ggggaccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc   1020
gagaaaacca tctccaaagc caaagggcag ccccgagaac cacaggtgta caccctgccc   1080
```

```
ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctatagcaa gctcaccgtg    1260
gacaagagca ggtggcagca ggggaacgtc ttctcatgct ccgtgatgca tgaggctctg    1320
cacaaccact acacgcagaa gagcctctcc ctgtccccgg gtaaatga              1368
```

```
<210> SEQ ID NO 62
<211> LENGTH: 663
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
gacatcgtga tgacacagag ccctagcagc ctgtctgtgt ctgccggcga gaaagtgacc     60
atgagctgca agagcagcca gaacctgctg aacagcggca accagaagaa ctacctggcc    120
tggtatcagc agaagcccgg ccagcctcct aagctgctga tctttggagc cagcaccaga    180
gaaagcggcg tgcccgatag atttacaggc tctggcagcg gcaccgactt cacccctgaca   240 atcagttctg tgcaggccga ggacctggcc gtgtactact gtcagagcga gcacagctac    300
ccctacacct ttggcggcgg aacaaagctg gaaatcaagc gtacggtggc tgcaccatct    360
gtcttcatct cccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tag                                                               663
```

```
<210> SEQ ID NO 63
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Phe Thr Phe Ser Asp Ala Trp
1               5
```

```
<210> SEQ ID NO 64
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Val Arg Asn Lys Ala Asn Asn His Ala Thr Tyr Tyr Ala Ala Ser Val
1               5                   10                  15

Lys Gly
```

<210> SEQ ID NO 65
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Thr Arg Ser Val Gly Gly Tyr Gly Thr Thr Tyr Trp Tyr Phe Asp Val
1               5                   10                  15

<210> SEQ ID NO 66
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gln Asn Leu Leu Asn Ser Gly Asn Gln Lys Asn Tyr
1               5                   10

<210> SEQ ID NO 67
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gly Ala Ser Thr Arg Glu Ser Gly Val Pro Asp
1               5                   10

<210> SEQ ID NO 68
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Gln Ser Glu His Ser Tyr Pro Tyr Thr
1               5

<210> SEQ ID NO 69

<400> SEQUENCE: 69

000

<210> SEQ ID NO 70

<400> SEQUENCE: 70

000

<210> SEQ ID NO 71
<211> LENGTH: 455
<212> TYPE: PRT
<213> ORGANISM: Artificial Sequence
<220> FEATURE:

-continued

<221> NAME/KEY: source
<223> OTHER INFORMATION: /note="Description of Artificial Sequence:
      Synthetic polypeptide"

<400> SEQUENCE: 71

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Val
        35                  40                  45

Gly Glu Val Arg Asn Lys Ala Asn Asn His Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Ser Val Gly Gly Tyr Gly Thr Thr Tyr Trp Tyr Phe
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
```

-continued

```
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455
```

```
<210> SEQ ID NO 72
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Asn Leu Leu Asn Ser
            20                  25                  30

Gly Asn Gln Lys Asn Tyr Leu Ala Trp Tyr Gln Gln Lys Pro Gly Gln
            35                  40                  45

Pro Pro Lys Leu Leu Ile Phe Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                    85                  90                  95

Glu His Ser Tyr Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220
```

```
<210> SEQ ID NO 73
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
```

```
gaggtgcagc tggttgaatc tggcggagga ctggttcagc ctggcggatc tctgaagctg      60
tcttgtgccg ccagcggctt cacctttttcc gacgcttgga tggactgggt ccgacaggcc     120
tctggcaaag gccttgagtg ggttggagaa gtgcggaaca aggccaacaa ccacgccacc     180
tactatgccg cctctgtgaa gggcagattc accatcagcc gggacgacag caagaacacc     240
gcctacctgc agatgaacag cctgaaaacc gaggacaccg ccgtgtacta ctgcaccaga     300
tctgttggcg gctacggcac cacctactgg tactttgatg tgtggggcca gggcaccacc     360
gtgacagttt cttctgcgtc gaccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagggcag ccccgagaac cacaggtgta caccctgccc    1080
ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctatagcaa gctcaccgtg    1260
gacaagagca ggtggcagca ggggaacgtc ttctcatgct ccgtgatgca tgaggctctg    1320
cacaaccact acacgcagaa gagcctctcc ctgtccccgg gtaaatga                 1368
```

```
<210> SEQ ID NO 74
<211> LENGTH: 663
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
```

```
gacatcgtga tgacacagag ccctgatagc ctggccgtgt ctctgggaga gagagccacc      60
atcaactgca agagcagcca gaacctgctg aacagcggca accagaagaa ctacctggcc     120
tggtatcagc agaagcccgg ccagcctcct aagctgctga tctttggagc cagcaccaga     180
gaaagcggcg tgcccgatag attttctggc agcggctctg gcaccgactt caccctgaca     240
attagctccc tgcaggccga ggatgtggcc gtgtactact gtcagagcga gcacagctac     300
ccctacacct ttggccaggg caccaagctg gaaatcaagc gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
``` gaagtcacccc atcagggcct gagctcgccc gtcacaaaga gcttcaacag gggagagtgt          660
tag                                                                                        663

<210> SEQ ID NO 75
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Arg Pro Gly Trp Tyr Cys Ala Leu Ser Lys Gln Glu Gly Cys Arg Leu
1               5                   10                  15

Cys Ala Pro Leu Arg Lys Cys Arg Pro Gly Phe Gly Val Ala Arg Pro
            20                  25                  30

Gly Thr Glu Thr Ser Asp
        35

<210> SEQ ID NO 76
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Phe Gln Leu Gln Gln Ser Gly Pro Glu Leu Val Lys Pro Gly Ala
1               5                   10                  15

Ser Val Lys Ile Ser Cys Lys Ala Ser Ser Tyr Ser Phe Thr Asp Tyr
            20                  25                  30

Asn Met Asn Trp Val Lys Gln Ser Asn Gly Lys Ser Leu Glu Trp Ile
        35                  40                  45

Gly Ile Ile Phe Pro Lys Tyr Gly Thr Thr Ser Tyr Asn Gln Lys Phe
    50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Thr Asp Gly Gly Thr Trp Tyr Phe Asp Val Trp Gly Thr Gly Thr
            100                 105                 110

Thr Val Thr Val Ser Ser
        115

<210> SEQ ID NO 77
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Phe Gln Leu Gln Gln Ser Gly Pro Glu Leu Val Lys Pro Gly Ala
1               5                   10                  15

Ser Val Lys Ile Ser Cys Lys Ala Ser Gly Phe Ser Phe Thr Asp Tyr
            20                  25                  30

```
Asn Met Asn Trp Val Lys Gln Ile Asn Gly Lys Ser Leu Glu Trp Ile
        35                  40                  45

Gly Ile Ile Tyr Pro Ile Tyr Gly Thr Thr Ser Tyr Asn Gln Lys Phe
        50                  55                  60

Arg Gly Lys Ala Thr Leu Thr Val Asp Leu Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Arg Ser Trp Tyr Phe Asp Val Trp Gly Thr Gly Thr Thr
                100                 105                 110

Val Thr Val Ser Ser
        115

<210> SEQ ID NO 78
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Phe Gln Leu Gln Gln Ser Gly Pro Lys Leu Val Lys Pro Gly Ala
1                   5                   10                  15

Ser Val Lys Ile Ser Cys Lys Ala Ser Gly Tyr Ser Phe Thr Asp Tyr
                20                  25                  30

Ser Met Asn Trp Val Lys Gln Ser Asn Gly Lys Ser Leu Glu Trp Ile
        35                  40                  45

Gly Ile Ile Asn Pro Asn Tyr Gly Ser Thr Ser Tyr Asn Gln Lys Phe
        50                  55                  60

Lys Val Lys Ala Thr Leu Thr Val Asp His Ser Ser Ser Thr Ala Tyr
65                  70                  75                  80

Met Gln Val Asn Ser Leu Thr Ser Glu Asp Ser Ala Val Tyr Tyr Cys
                85                  90                  95

Ala Arg Ser Ser Thr Trp Tyr Phe Asp Val Trp Gly Thr Gly Thr Thr
                100                 105                 110

Val Thr Val Ser Ser
        115

<210> SEQ ID NO 79
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Val Gln Leu Gln Gln Ser Gly Pro Glu Leu Val Lys Pro Gly Ala
1                   5                   10                  15

Ser Val Arg Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
        35                  40                  45

Gly Asp Ile Asn Pro Asn Asp Gly Gly Thr Thr Tyr Ser Gln Lys Phe
        50                  55                  60

Lys Gly Lys Ala Thr Leu Thr Val Asp Lys Ser Ser Ser Thr Ala Tyr
```

-continued

```
65                  70                  75                  80

Met Glu Leu Arg Ser Leu Thr Ser Glu Asp Ser Ala Val Tyr Phe Cys
                85                  90                  95

Ala Arg Glu Gly Asn Tyr Tyr Ala Tyr Asp Val Arg Val Trp Tyr Phe
            100                 105                 110

Asp Val Trp Gly Thr Gly Thr Thr Val Thr Val Ser Ser
        115                 120                 125

<210> SEQ ID NO 80
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Ser
            20                  25                  30

Glu Met His Trp Val Lys Gln Thr Pro Val His Gly Leu Glu Trp Ile
        35                  40                  45

Gly Glu Ile Asp Pro Glu Ala Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Glu Asp Tyr Asp Trp Phe Thr Tyr Trp Gly Gln Gly Thr Leu
            100                 105                 110

Val Thr Val Ser Ala
        115

<210> SEQ ID NO 81
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Ile Lys Tyr Ser Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Tyr Glu Asp Ser Ala Val Tyr Tyr Cys
                85                  90                  95

Ala Arg Ser Tyr Tyr Asp Tyr Asp Gly Gly Phe Ala Tyr Trp Gly Gln
            100                 105                 110
```

```
Gly Thr Leu Val Thr Val Ser Ala
        115                 120

<210> SEQ ID NO 82
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asp Ile Lys Asp Asp
            20                  25                  30

Phe Ile His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ser Thr Leu Leu Arg Tyr Tyr Phe Asp Tyr Trp Gly Gln Gly Thr Thr
            100                 105                 110

Leu Thr Val Ser Ser
        115

<210> SEQ ID NO 83
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Ala
            20                  25                  30

Gly Met Gln Trp Val Gln Lys Met Pro Gly Lys Gly Phe Lys Trp Ile
        35                  40                  45

Gly Trp Ile Asn Thr His Ser Gly Glu Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Leu Tyr Ala Met Asp Tyr Trp Gly Gln Gly Thr Ser Val Thr Val
            100                 105                 110

Ser Ser

<210> SEQ ID NO 84
<211> LENGTH: 125
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
            35                  40                  45

Ala Glu Val Arg Asn Lys Ala Asn Asn His Ala Thr Tyr Tyr Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Ser Val Gly Gly Tyr Gly Thr Thr Tyr Trp Tyr Phe
                100                 105                 110

Asp Val Trp Gly Thr Gly Thr Thr Val Thr Val Ser Ser
            115                 120                 125

<210> SEQ ID NO 85
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ile Ser Tyr
            20                  25                  30

Ala Met Ser Trp Val Arg Gln Thr Pro Glu Lys Arg Leu Glu Trp Val
            35                  40                  45

Ala Thr Ile Ser Asp Gly Gly Ser Tyr Thr Tyr Tyr Pro Asp Asn Val
        50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Asp Tyr Asp Tyr Phe Asp Tyr Trp Gly Gln Gly Thr Thr Leu
                100                 105                 110

Thr Val Ser Ser
            115

<210> SEQ ID NO 86
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86
```

-continued

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Ile Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Val Arg Glu Tyr Phe Asp Val Trp Gly Thr Gly Thr Thr Val Thr Val
            100                 105                 110

Ser Ser
```

```
<210> SEQ ID NO 87
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87
```

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Ser Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ile Thr Thr Val Val Tyr Tyr Val Met Asp Asn Trp Gly
            100                 105                 110

Gln Gly Thr Ser Val Thr Val Ser Ser
        115                 120
```

```
<210> SEQ ID NO 88
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88
```

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Arg Ser Ser Pro Lys Pro Trp Ile Tyr
```

-continued

```
            35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                    85                  90                  95

Phe Gly Ser Gly Thr Lys Leu Glu Ile Lys
                100                  105
```

<210> SEQ ID NO 89
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

```
Gln Ile Val Leu Thr Gln Ser Pro Ala Leu Met Ser Ala Ser Pro Gly
1                   5                   10                  15

Glu Lys Val Thr Met Ile Cys Ser Ala Ser Ser Ser Val Arg Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                    85                  90                  95

Phe Gly Pro Gly Thr Lys Leu Glu Leu Lys
                100                  105
```

<210> SEQ ID NO 90
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

```
Gln Ile Val Leu Thr Gln Ser Pro Ala Leu Met Ser Ala Ser Pro Gly
1                   5                   10                  15

Glu Lys Val Thr Met Thr Cys Ser Ala Ser Ser Ser Val Ser Tyr Met
                20                  25                  30

Tyr Trp Tyr Gln Gln Lys Pro Arg Ser Ser Pro Lys Pro Trp Ile Tyr
            35                  40                  45

Leu Thr Ser Asp Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                    85                  90                  95

Phe Gly Gly Gly Thr Lys Leu Glu Ile
                100                  105
```

```
<210> SEQ ID NO 91
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105

<210> SEQ ID NO 92
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Gly Val Ser Ser Ser
            20                  25                  30

Tyr Leu Tyr Trp Tyr Gln Gln Lys Pro Gly Ser Ser Pro Lys Val Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Leu Thr Phe Gly Ala Gly Thr Lys Leu Glu Leu Lys
            100                 105

<210> SEQ ID NO 93
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93
```

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Ile Leu Gln Ser Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys
            100                 105
```

<210> SEQ ID NO 94
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

```
Asp Ile Gln Met Thr Gln Ser Pro Ala Ser Leu Ser Val Ser Val Gly
1               5                   10                  15

Glu Thr Val Thr Ile Thr Cys Arg Ser Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys
            100                 105
```

<210> SEQ ID NO 95
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Arg Gln Gly Arg Ser Pro Gln Leu Leu Val
        35                  40                  45

Tyr His Ala Lys Thr Leu Thr Glu Gly Val Pro Ser Arg Phe Ser Gly
    50                  55                  60

Ser Gly Ser Gly Thr Gln Phe Ser Leu Lys Ile Asn Ser Leu Gln Pro
```

```
65                  70                  75                  80

Glu Asp Phe Gly Thr Tyr Tyr Cys Gln His His Tyr Gly Thr Pro Trp
                85                  90                  95

Thr Phe Gly Gly Gly Thr Lys Leu Glu Ile Arg
            100                 105

<210> SEQ ID NO 96
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Asp Ile Val Met Thr Gln Ser Pro Ser Ser Leu Ser Val Ser Ala Gly
1               5                   10                  15

Glu Lys Val Thr Met Ser Cys Lys Ser Ser Gln Asn Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Phe Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Ser
                85                  90                  95

Glu His Ser Tyr Pro Tyr Thr Phe Gly Gly Gly Thr Lys Leu Glu Ile
            100                 105                 110

Lys

<210> SEQ ID NO 97
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Leu Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
            100                 105                 110

<210> SEQ ID NO 98
<211> LENGTH: 112
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 99
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Tyr Thr Phe Gly Gly Gly Thr Lys Leu Glu Ile Lys
            100                 105                 110
```

<210> SEQ ID NO 100
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
```

-continued

```
              20                 25                 30

Ser Lys Cys Ser Pro Gly Gln His Ala Lys Val Phe Cys Thr Lys Thr
        35                 40                 45

Ser Asp Thr Val Cys Asp Ser Cys Glu Asp Ser Thr Tyr Thr Gln Leu
    50                 55                 60

Trp Asn Trp Val Pro Glu Cys Leu Ser Cys Gly Ser Arg Cys Ser Ser
65                 70                 75                 80

Asp Gln Val Glu Thr Gln Ala Cys Thr Arg Glu Gln Asn Arg Ile Cys
                85                 90                 95

Thr Cys Arg Pro Gly Trp Tyr Cys Ala Leu Ser Lys Gln Glu Gly Cys
            100                105                110

Arg Leu Cys Ala Pro Leu Arg Lys Cys Arg Pro Gly Phe Gly Val Ala
        115                120                125

Arg Pro Gly Thr Glu Thr Ser Asp Val Val Cys Lys Pro Cys Ala Pro
    130                135                140

Gly Thr Phe Ser Asn Thr Thr Ser Ser Thr Asp Ile Cys Arg Pro His
145                150                155                160

Gln Ile Cys Asn Val Val Ala Ile Pro Gly Asn Ala Ser Met Asp Ala
            165                170                175

Val Cys Thr Ser Thr Ser Pro Thr Arg Ser Met Ala Pro Gly Ala Val
        180                185                190

His Leu Pro Gln Pro Val Ser Thr Arg Ser Gln His Thr Gln Pro Thr
    195                200                205

Pro Glu Pro Ser Thr Ala Pro Ser Thr Ser Phe Leu Leu Pro Met Gly
    210                215                220

Pro Ser Pro Pro Ala Glu Gly Ser Thr Gly Asp His His His His His
225                230                235                240

His
```